US008557828B2

(12) United States Patent
Liu et al.

(10) Patent No.: US 8,557,828 B2
(45) Date of Patent: Oct. 15, 2013

(54) INHIBITORS OF DIACYLGLYCEROL O-ACYLTRANSFERASE TYPE 1 ENZYME

(75) Inventors: Gang Liu, San Diego, CA (US); Zhili Xin, Lake Bluff, IL (US); Philip R. Kym, Libertyville, IL (US); Andrew J. Souers, Evanston, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/277,909

(22) Filed: Oct. 20, 2011

(65) Prior Publication Data

US 2012/0041003 A1 Feb. 16, 2012

Related U.S. Application Data

(62) Division of application No. 12/112,643, filed on Apr. 30, 2008, now Pat. No. 8,076,344.

(60) Provisional application No. 60/914,999, filed on Apr. 30, 2007.

(51) Int. Cl.
*A01N 43/90* (2006.01)
*A61K 31/519* (2006.01)

(52) U.S. Cl.
USPC .................................... 514/259.31

(58) Field of Classification Search
None
See application file for complete search history.

(56) References Cited

U.S. PATENT DOCUMENTS

| 2,779,799 | A | 1/1957 | Hamlin |
| 6,100,077 | A | 8/2000 | Sturley et al. |
| 7,091,228 | B2 | 8/2006 | Smith et al. |
| 2004/0224997 | A1 | 11/2004 | Smith et al. |

FOREIGN PATENT DOCUMENTS

| EP | 1149835 A1 | 10/2001 |
| WO | 0139773 A1 | 6/2001 |
| WO | 2006078676 A2 | 7/2006 |
| WO | 2006092414 A1 | 9/2006 |
| WO | 2006092428 A2 | 9/2006 |

OTHER PUBLICATIONS

Borisy, et. al., Proceedings of the National Academy of Sciences of the United States of America, 100(13) 7977-7982.*
Borisy, et. al., Proceedings of the National Academy of Sciences of the United States of America, (2003); 100(13) 7977-7982.*
Wolff et. al., "Burger's Medicinal Chemistry and Drug Discovery," 5th Ed. Part 1, pp. 975-977 (1995).
Banker, et. al,, Modern Pharmaceuticals, (1996), p. 596.
Dorwald F. A. Side Reactions in Organic Synthesis, 2005, Wiley: VCH, Weinheim p. IX of Preface.
Anh JH, Joung MJ, Yoon NM, "A New Method of Synthesis for Propargylic Amines and Ethers via Benzotriazole Derivatives Using Sodium Dialkynyldiethylaluminates", J Org Chem, 1999, 64, 488-492.
Belotti D. et al., "Synthesis of Bicyclic Cyclopentanols by Photoreductive Cyclization of 6,e-Unsaturated Ketones," J. Org. Chem., 1986, pp. 4196-4200, vol. 51.
Buhman KK, Smith SJ, Stone SJ, et al., "DGAT1 is not essential for intestinal triacylglycerol absorption or chylomicron synthesis", J Bioi Chem, 2002, 277/28, 25474-9.
Burgess Kevin et al,, "Chiral1 ,3-Cyclobutane Amino Adds: Syntheses and Extended Conformations," Tetrahedron Letters, 1997, pp. 1681-1684, vol. 38 (10), Elsevier Science.
Cases S, Smith SJ, Zheng YW, et al., "Identification of a gene encoding an acyl CoA:diacylglycerol acyltransferase, a key enzyme in triacylglycerol synthesis", Proc Natl Acad Sci, 1998, 95/22, 13018-13023.
Cases S, Stone SJ, Zhou P, et al., "Cloning of DGAT2, a second mammalian diacylglycerol acyltransferase, and related family members", J Bioi Chem, 2001, 276/42, 38870-6.
Chen HC, Farese RV Jr, "Inhibition of triglyceride synthesis as a treatment strategy for obesity: lessons from DGAT1-deficient mice", Arterioscler Thromb Vase Bioi, 2005, 25/3, 482-6.
Chen HC Farese RV Jr., "DGAT and triglyceride synthesis: a new target for obesity treatment?", Trends Cardiovasc Med, 2000, 10/5, 188-92.
Chen HC, Smith SJ, Ladha Z, et al., "Increased insulin and leptin sensitivity in mice lacking acyl CoA:diacylglycerol acyltransferase 1", J Clin Invest, 2002, 109/8, 1049-55.
Collins S, Martin TL, Surwit RS, Robidoux J, "Genetic vulnerability to diet-induced obesity in the C57BU6J mouse: physiological and molecular characteristics", Physiol Behav 2004 81/2 243-8.
Dufey Pierre "On the preparation of2-alkyl hexahydrochromanols," P. Bull. Soc. Chim. Fr., 1968, pp. 4653-4662.
Greene, T. W. et al., "Protective Groups in Organic Synthesis," 1999, 4 Pages, 3 rd Ed, John Wiley & Sons.
Grundy SM, "Metabolic complications of obesity", Endocrine, 2000, 13/2, 155-165.

(Continued)

*Primary Examiner* — Jeffrey Murray
(74) *Attorney, Agent, or Firm* — Lisa V. Mueller; Michael Best & Friedrich LLP

(57) ABSTRACT

The present invention relates to compounds of formula (I):

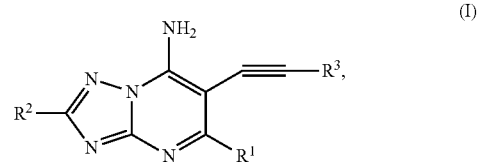

wherein $R^1$, $R^2$, and $R^3$, are defined herein. Pharmaceutical compositions and methods for treating DGAT-1 related diseases or conditions are also disclosed.

14 Claims, No Drawings

(56) References Cited

OTHER PUBLICATIONS

Harada H, Asano 0, Hoshino Y, et al., "2-Aiykynyl-8-aryl-9-methyladenines as Novel Adenosine Receptor Antagonists: Their Synthesis and Structure-Activity Relationships toward Hepatic Glucose Production Induced via Agonism of the A(2B) Receptor", J Med Chern, 2001, 44, 170-179.

Harfenist M, Thom E, "The Influence of Structure on the Rate of Thermal Rearrangement of Aryl Propargyl Ethers to the Chromenes. The gem-Dimethyl Effect", J Org Chem, 1972, 37/6, 841-48.

Hennion G. F. et al., "The Kinetics of the Hydrolysis of Acetylenic Chlorides and Their Reactions with Primary and Secondary Aliphatic Amines," Journal of the American Chemical Society, 1957, pp. 2142-2145 vol. 79 (9).

Higuchi T. and Stella V., "Pro-drugs as Novel Delivery Systems," Bioreversible Carriers in Drug Design, 1987, vol. 14, American Pharmaceutical Association and Pergamon Press.

Hiroshi Suemune et al., "Ring Cleavage and Reconstruction of Five and Six Membered Rina," Tetrahedron Letters, 1987, pp. 3373-3376, vol. 28 (29).

Kano H. Makisumi Y. "Synthesis of Potential Anticancer Agents. I. 5-Substituted 7-Methyl-s-triazolo[4,3-a] and -tetrazolo[1.5-a)-pyrimidines", Chem Pharm Bull, 1958, 6/6, 583-585.

Lee V. et al., "Novel Annulation Reactions: a Simple Preparation of Spirocycles and an Allylsilane Based Bifunctional Acceptor-Donor Annulating Reagent," Tetrahedron Letters, 1986, pp. 5021-5024, vol. 27 (41), Pergamon Journals Ltd.

Lewis GF, Carpenter A, Adeli K. "Disordered fat storage and mobilization in the pathoaenesis of insulin resistance and type 2 diabetes", Endocr Rev, 2002, 23/2, 201-29.

Ochiai M et al., "Synthesis of ethynyl(phenyl)iodonium tetrafluoroborate. A new reagent for ethynylation of 1,3-dicarbonyl compounds," J Chem Soc Chem Cornrnun, 1990, pp. 118-119.

Roche, E. B., "Bioreversible Carriers in Drug Design: Theory and Application," American Pharmaceutical Association, 1987, 13-21, PerQarnon Press.

Roger et al "Autocondensation de l'oxyde de mesityle sur magnesie a differentes oressions," Bulletin of Chemical Societv of France, 1967, pp. 3030-3037.

Rouzaud et al., "Transpositions d'hydroxy-1 cyaohexylcarbinols e t des cetones isomeres correspondantes (2e memoir®). Synthese des cetones" Bull Soc Chim Fr, 1965, pp. 2030-2037.

Smith SJ, Cases S, Jensen DR, et al., Obesity resistance and multiple mechanisms of triglyceride synthesis in mice lacking Ogaf, Nat Genet, 2000, 25/1, 87-90.

Tsuji Yutaka et al,, "Substituent Effects. 22. 1) The Solvolysis of a-t-Butylbenzyl Tosylates," Bull. Chem. Soc., 1990 pp. 856-866, vol. 63 (3).

Unger RH, "Mini review: weapons of lean body mass destruction: the role of ectopic lipids in the metabolic svndome" Endocrinology, 2003, 144/12, 5159-5165.

\* cited by examiner

INHIBITORS OF DIACYLGLYCEROL O-ACYLTRANSFERASE TYPE 1 ENZYME

CROSS-REFERENCE TO RELATED APPLICATIONS

This is a divisional of U.S. patent application Ser. No. 12/112,643, filed on Apr. 30, 2008, which claims priority to U.S. Provisional Patent Application No. 60/914,999, filed, Apr. 30, 2007, the contents of all of which are hereby incorporated by reference.

FIELD OF THE INVENTION

Compounds that are inhibitors of the diacylglycerol O-acyltransferase type 1 (DGAT-1) enzyme, are disclosed. Methods of using such compounds to inhibit the activity of diacylglycerol O-acyltransferase type 1 and pharmaceutical compositions including such compounds are also encompassed.

BACKGROUND OF THE INVENTION

Triacylglycerides represent the major form of energy storage in eukaryotes, and disorders or imbalance in triacylglycerides metabolism are implicated in the pathogenesis and increased risk, for obesity, insulin resistance, type II diabetes, nonalcoholic fatty liver disease and coronary heart disease (Lewis, et al., Endocrine Reviews 23:201, 2002). Storage of excess triacylglycerides in lean tissues, such as liver, muscle, and other peripheral tissues, leads to lipid-induced dysfunction in those tissues; thus, reducing fat accumulation in nonadipose sites appears to be of benefit in the treatment of lipotoxicity (Unger, R. H. Endocrinology, 144: 5159-5165, 2003). Accumulation of excess triacylglycerides in white adipose tissue (WAT) leads to obesity, a condition that is associated with decreased life span, type II diabetes, coronary artery disease, hypertension, stroke, and the development of some cancers (Grundy, S. M. Endocrine 13(2): 155-165, 2000). Obesity is a chronic disease that is highly prevalent in modern society and current pharmacological treatment options are limited, creating a need to develop pharmaceutical agents for the treatment of obesity that are safe and effective.

Diacylglycerol O-acyltransfereases (DGATs) are membrane-bound enzymes that catalyze the terminal step of triacylglycerides biosynthesis. Two enzymes that display DGAT activity have been characterized: DGAT-1 (diacylglycerol O-acyltransferase type 1) (U.S. Pat. No. 6,100,077; Cases, et al., Proc. Nat. Acad. Sci. 95:13018-13023, 1998) and DGAT-2 (diacylglyerol O-acyltransferase type 2) (Cases, et al., J. Biol. Chem. 276:38870, 38876, 2001). DGAT-1 and DGAT-2 share only 12% sequence identity. Significantly, DGAT-1 null mice are resistant to diet-induced obesity and have increased sensitivity to insulin and leptin (Smith, et al., Nature Genetics 25:87-90, 2000; Chen and Farese, Trends Cardiovasc Med. 10:188, 2000; Chen et al., J. Clin. Invest. 109:10049, 2002); DGAT-1 deficient mice are protected against hepatic steatosis, demonstrate increased energy expenditure, and decreased levels of tissue triacylglycerides. In addition to improved triacylglycerides metabolism, DGAT-1 deficient mice also have improved glucose metabolism, with lower glucose and insulin levels following a glucose load, in comparison to wild-type mice. Partial DGAT-1 deficiency in heterozygous DGAT-1+/− animals is sufficient to deliver an intermediate phenotype on body weight, adiposity, and insulin and glucose metabolism when compared to wild type and homozyogous littermates (Chen and Farese, Arterioscler. Thromb. Vasc. Biol. 25:482-486, 2005), and small molecule DGAT-1, inhibitors have been reported to induce weight loss in diet-induced obese (DIO) mice (US 2004/0224997). The phenotypes of DGAT-1 deficient mice, and the pharmacological activity reported with DGAT-1 inhibitors suggests that the discovery of small molecules that effectively block the conversion of diacylglycerol to triacylglycerides by inhibiting the DGAT-1 enzyme can have utility in the treatment of obesity and other diseases associated with triacylglycerides imbalance.

SUMMARY OF THE INVENTION

One aspect of the invention is directed, towards compounds of formula (I), or a pharmaceutically acceptable salt; prodrug, salt of a prodrug, or a combination thereof,

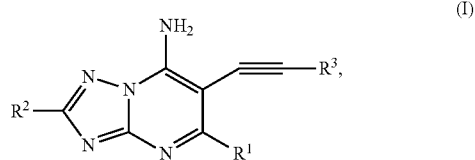

or pharmaceutically acceptable salts, prodrugs, salts of prodrugs, or a combination thereof, wherein $R^1$ is hydrogen or alkyl;

$R^2$ is hydrogen, halogen, alkyl, haloalkyl, aryl, heteroaryl, cycloalkyl, or heterocycle;

$R^3$ is cycloalkyl, aryl, heteroaryl, heterocycle, —$(CR^aR^b)_m$—$R^4$, —$C(O)OR^5$, —$C(R^5)$=N—$O(R^y)$, —$C(O)$—$R^5$, or —$C(O)$—$N(R^5)(R^6)$;

m is 1, 2, 3 or 4;

$R^a$, at each occurrence, is, independently hydrogen, halogen, alkyl, alkenyl, haloalkyl, —$OR^{7a}$, —$N(R^8)(R^9)$, —$C(O)OR^{7b}$, —$C(O)$—$R^{7b}$, —$C(O)$—$N(R^8)(R^9)$, —$(CR^cR^d)_p$—$OR^{7a}$, —$(CR^cR^d)_p$—$N(R^8)(R^9)$, —$(CR^cR^d)_p$—$C(O)OR^{7b}$, —$(CR^cR^d)_p$—$C(O)$—$R^{7b}$, —$(CR^cR^d)_p$—$C(O)$—$N(R^8)(R^9)$, aryl, heteroaryl, cycloalkyl, or heterocycle;

$R^b$, at each occurrence, is independently hydrogen, halogen, alkyl, alkenyl, haloalkyl, —$C(O)OR^{7b}$, —$C(O)$—$R^{7b}$, —$C(O)$—$N(R^8)(R^9)$, —$(CR^cR^d)_p$—$OR^{7a}$, —$(CR^cR^d)_p$—$N(R^8)(R^9)$, —$(CR^cR^d)_p$—$C(O)OR^{7b}$, —$(CR^cR^d)_p$—$C(O)$—$R^{7b}$, —$(CR^cR^d)_p$—$C(O)$—$N(R^8)(R^9)$, aryl, heteroaryl, cycloalkyl, or heterocycle;

optionally $R^a$ and $R^b$ together is =$CH_2$;

$R^c$ and $R^d$, at each occurrence, are each independently hydrogen; halogen, alkyl, or haloalkyl;

$R^y$ is hydrogen, alkyl, haloalkyl, cycloalkyl, aryl, heteroaryl, heterocycle, cycloalkylalkyl, arylalkyl, heteroarylalkyl, or heterocyclealkyl;

$R^4$ is hydrogen, alkyl, haloalkyl, cycloalkyl, aryl, heteroaryl, or heterocycle, provided that when $R^4$ is hydrogen, alkyl or haloalkyl, then at least one $R^a$ is —$OR^{7a}$, —$N(R^8)(R^9)$, —$C(O)OR^{7b}$, —$C(O)$—$R^{7b}$, —$C(O)$—$N(R^8)(R^9)$, —$(CR^cR^d)_p$—$OR^{7a}$, —$(CR^cR^d)_p$—$N(R^8)(R^9)$, —$(CR^cR^d)_p$—$C(O)OR^{7b}$, —$(CR^cR^d)_p$—$C(O)$—$R^{7b}$, or —$(CR^cR^d)_p$—$C(O)$—$N(R^8)(R^9)$; or $R^a$ and $R^b$ together is =$CH_2$;

$R^5$, at each occurrence, is independently alkyl, haloalkyl, cycloalkyl, heteroaryl, heterocycle, cycloalkylalkyl, arylalkyl, heteroarylalkyl, or heterocyclealkyl;

wherein each of the cycloalkyl, aryl, heteroaryl, heterocycle, cycloalkyl moiety of the cycloalkylalkyl, aryl moiety of the arylalkyl, heteroaryl moiety of the heteroarylalkyl, and heterocycle moiety of the heterocyclealkyl, as represented by $R^2$, $R^3$, $R^a$, $R^b$, $R^4$, $R^5$, and $R^y$, is independently unsubstituted or further, substituted with 1, 2, 3, 4 or 5 Substituents selected from, but not limited to, alkyl, halogen, haloalkyl, oxo, $OR^{10}$, $—S(R^{14})$, $—S(O)_2R^{15}$, $—S(O)_2N(R^{11})(R^{12})$, $—N(R^{11})(R^{12})$, $—C(O)OR^{10}$, $—C(O)O(trialkylsilylalkyl)$, $—C(O)N(R^{11})(R^{12})$, $—(CR^eR^f)_q—OR^{10}$, $—(CR^eR^f)_q—N(R^{11})(R^{12})$, $—(CR^eR^f)_q—C(O)OR^{10}$, $—(CR^eR^f)_q—C(O)N(R^{11})(R^{12})$, $G^1$, and $=N—O(R^{10})$, $R^6$, $R^9$ and $R^{12}$, at each occurrence, are each independently hydrogen, alkyl or haloalkyl;

$R^{7a}$, at each occurrence, is each independently hydrogen, alkyl, haloalkyl, $—N=C(H)R^{13a}$, $—(CR^gR^h)_r—C(O)OR^{13}$, or $G^1$, $R^{7b}$ and $R^{10}$, at each occurrence, are each independently hydrogen, alkyl, haloalkyl, $—(CR^gR^h)_r—C(O)OR^{13}$, or $G^1$, $R^8$ and $R^{11}$, at each occurrence, are each independently hydrogen, alkyl, haloalkyl, $—S(O)_2—R^{13a}$, $—S(O)_2—N(R^{13})(R^{14})$, $—C(O)OR^{13}$, $—C(O)N(R^{13})(R^{14})$, or $G^1$;

p, q and r, at each occurrence, are each independently 1, 2, 3, or 4;

$R^e$, $R^f$, $R^g$, and $R^h$, at each occurrence, are each independently hydrogen, halogen, alkyl, or haloalkyl;

$R^{14}$, at each occurrence, is independently hydrogen, alkyl or haloalkyl;

$R^{15}$, at each occurrence, is independently alkyl, haloalkyl, or $G^1$;

$R^{13}$, at each occurrence, is independently hydrogen, alkyl; haloalkyl, or $G^1$;

$R^{13a}$, at each occurrence, is independently alkyl, haloalkyl, or $G^1$; and $G^1$, at each occurrence, is independently aryl, heteroaryl, cycloalkyl, heterocycle, arylalkyl, heteroarylalkyl, cycloalkylalkyl, or heterocyclealkyl, wherein the aryl, heteroaryl, cycloalkyl, heterocycle, aryl moiety of the arylalkyl, heteroaryl moiety of the heteroarylalkyl, cycloalkyl moiety of the cycloalkylalkyl, and heterocycle moiety of the heterocyclealkyl, are each independently unsubstituted or further substituted with 1, 2, 3, 4 or 5 substituents selected from, but not limited to, alkyl, halogen, —CN, —NO$_2$, —OH, —O(alkyl), —NH$_2$, —N(H)(alkyl), —N(alkyl)$_2$, —C(O)OH, —C(O)O(alkyl), —C(O)NH$_2$, —C(O)N(H)(alkyl), —C(O)N(alkyl)$_2$, haloalkyl, and alkyl, substituted with one substituent selected from, but not limited to, —CN, —NO$_2$, —OH, —O(alkyl), —NH$_2$, —N(H)(alkyl), —N(alkyl)$_2$, —C(O)OH, —C(O)O(alkyl), —C(O)NH$_2$, —C(O)N(H)(allyl), and —C(O)N(alkyl)$_2$.

Another aspect of the invention provides methods of treating, various diseases or conditions in a subject; preferably a human, wherein the methods include administering to the subject in need thereof a therapeutically or prophylactically effective amount of a compound of the invention as disclosed herein, or a pharmaceutically acceptable salt thereof, alone or in combination with a pharmaceutically acceptable carrier. In another aspect, the invention provides methods of preventing or treating a disease or condition related to elevated lipid levels, such as plasma lipid levels, especially elevated triacylglycerides levels, in a subject, especially human, afflicted with such elevated levels, including administering to a subject a therapeutically or prophylactically effective amount of a compound, a pharmaceutically acceptable salt thereof, or a pharmaceutical composition including the same, as disclosed herein. The invention also relates to compounds having therapeutic ability to reduce lipid levels, especially triacylglycerides levels, in a subject. Accordingly, the compounds and compositions of the invention, alone or together with one or more pharmaceutical agents selected from the group consisting of DPPIV inhibitor, incretin mimetic, metformin, fenofibrate, rimonabant, sibutramine, orlistat, nicotinic acid, and a statin, are useful for the preparation of a medicament for treating or preventing diseases and disorders described herein, particularly, for treating or preventing type 2 diabetes, obesity, elevated plasma triglycerides, metabolic syndrome, non-alcoholic steatohepatitis, and non-alcoholic fatty liver disease. Compounds of the invention or pharmaceutically acceptable salt thereof, or compositions thereof, alone or together with one or more pharmaceutical agents as described herein, are also useful for the preparation of a medicament for reducing lipid levels in a subject (e.g. mammal, including human), especially triglycerides levels. In another aspect, the invention provides pharmaceutical compositions including one or more compounds of the invention as disclosed herein, or a pharmaceutically acceptable salt thereof, and a pharmaceutically acceptable carrier.

DETAILED DESCRIPTION OF THE INVENTION

For a variable that occurs more than one time in any substituent or in the of the invention or any other formulae herein, its definition on each occurrence is independent of its definition at every other occurrence. Combinations of substituents are permissible only if such combinations result in stable compounds. Stable compounds are compounds which can be, isolated in a useful degree of purity from a reaction mixture.

As used in the specification and the appended claims, unless specified to the contrary, the following terms, have the meaning indicated:

The term "alkenyl" as used herein, means a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl" as used herein, means a straight or branched, saturated hydrocarbon chain containing from 1 to 10 carbon atoms. The term "lower alkyl" or "$C_{1-6}$ alkyl" means, a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon of from 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. The phenyl and the bicyclic aryl groups of they, present invention are unsubstituted or substituted. The bicyclic aryl is attached to the parent molecular moiety through any carbon atom contained within the bicyclic aryl. Representative examples of the aryl groups include, but are not limited to, bicyclo[4.2.0]octa-1,3,5-trien-7-yl, dihydroindenyl, indenyl, naphthyl, dihydronaphthalenyl, and 5,6,7,8-tetrahydronaphthalenyl.

The term "arylalkyl" as used herein, means an aryl group; as defined herein, appended to the parent molecular moiety through an alkyl group, as defined herein. Representative examples of arylalkyl include, but are not limited to, benzyl, 2-phenylethyl and 3-phenylpropyl.

The term "cycloalkyl" or "cycloalkane" as used herein, means a monocyclic, a bicyclic cycloalkyl or a tricyclic cycloalkyl. The monocyclic cycloalkyl is a hydrocarbon ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic cycloalkyl in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bridged bicyclic cycloalkyl in which two non-adjacent carbon atoms of the bicyclic ring system are linked by an alkylene bridge of between one and four carbon atoms. Representative examples of tricyclic-ring systems include, but are not limited to, tricyclo[3.3.1.0$^{3,7}$]nonane and tricyclo[3.3.1.1$^{3,7}$]decane (adamantane). The monocyclic, bicyclic, and tricyclic cycloalkyls can be attached to the parent molecular moiety through any substitutable atom contained, within the bicyclic and tricyclic cycloalkyls, and are each unsubstituted or substituted.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl and cyclohexylmethyl.

The term "cycloalkenyl" or "cycloalkene" as used herein, means a monocyclic or a bicyclic hydrocarbon ring system. The monocyclic cycloalkenyl contains four-, five-, six-, seven- or eight carbon atoms and zero heteroatom. The four-membered ring systems have one double bond, the five- or six-membered ring systems have one or two double bonds, and the seven- or eight-membered ring systems have one, two or three double bonds. The monocyclic cycloalkenyl can be attached to the parent molecular moiety through any substitutable atom contained within the monocyclic cycloalkenyl. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring can contain one or two alkylene bridges, each including one, two, three or four carbon atoms and each linking two non-adjacent carbon atoms of the ring. The bicyclic cycloalkenyl can be attached to the parent molecular moiety through any substitutable atom contained within the bicyclic, cycloalkenyl. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl groups of the present invention can be unsubstituted or substituted.

The term "cycloalkenylalkyl" as used herein, means a cycloalkenyl group, as defined herein, appended to the parent molecular moiety through an alkyl group, as defined herein.

The term "halo" or "halogen" as used herein, means Cl, Br, I or F.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, trifluoromethyl, difluoromethyl, pentafluoroethyl, and 2-chloro-3-fluoropentyl.

The term "heterocycle" or "heterocyclic" as used herein, means a monocyclic heterocycle, a bicyclic, or a tricyclic, heterocycle. The monocyclic heterocycle is a three-, four-, five-, six- or seven-membered ring containing at least one heteroatom independently selected from, but not limited to, O, N, and S. The three- or four-membered ring contains zero or one double bond, and one heteroatom selected from, but not limited to, O, N and S. The five-membered ring contains zero or one double bond and one, two or three heteroatoms selected from, but not limited to, O, N and S. The six-membered ring contains zero, one or two double bonds and one, two or three heteroatoms selected from, but not limited to, O, N and S. The seven-membered ring contains zero, one, two, or three double bonds and one, two or three heteroatoms selected from, but not limited to, O, N and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydro-2H-pyranyl tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged, monocyclic heterocycle ring system in which two non adjacent atoms of the ring are linked by an alkylene bridge containing one, two, three, or four carbon atoms. Representative examples of bicyclic heterocycles include, but are not limited to, benzopyranyl, benzothiopyranyl, 2,3-dihydrobenzofuranyl, 2,3-dihydrobenzothienyl, and 2,3-dihydro-1H-indolyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bridged bicyclic heterocycle in which two non adjacent atoms of the bicyclic ring are linked by an alkylene bridge including one, two, three, or four carbon atoms. Examples of tricyclic heterocycles include, but are not limited to, oxaadamantane and aza-admantane. The monocyclic, bicyclic and tricyclic heterocycles are connected to the parent molecular moiety through any carbon atom or any nitrogen atom contained within the rings. The monocyclic, bicyclic and tricyclic heterocycles of the present invention can be unsubstituted or substituted.

The term "heterocyclealkyl" as used herein, means a heterocycle, as defined herein, appended to the parent molecular moiety through an alkyl group, as defined herein.

The term "heteroaryl" as used herein, means a monocyclic heteroaryl, or a bicyclic heteroaryl. The monocyclic heteroaryl is a five- or six-membered ring. The five-membered ring contains two double bonds. The five-membered ring can contain one heteroatom selected from O or S; or one, two, or three nitrogen atoms and optionally an additional heteroatom selected from oxygen or sulfur; or four nitrogen atoms. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl is exemplified by a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention are connected to the parent molecular moiety through any carbon atom or any nitrogen atom contained within the rings and are substituted or unsubstituted.

The term "heteroarylalkyl" as used herein, means a heteroaryl, as defined herein, appended to the parent molecular moiety through an alkyl group, as defined herein.

The term "heteroatom" as used herein, means a nitrogen, oxygen or sulfur atom.

The term "oxo" as used herein, means a =O group.

The term "trialkylsilyl" as used herein, means (alkyl)$_3$-Si group, attached to the parent molecular moiety through the silicon atom.

The term "trialkylsilylalkyl" as used herein, means a trialkylsilyl group, as defined herein, appended to the parent molecular moiety through an alkyl group, as defined herein.

The term "mammal" as used herein means humans and animals, such as cats, dogs, swine, cattle, horses; and the like.

Compounds of the invention have the formula (I) as described above.

Particular values of variable groups in compounds of formula (I) are as follows. Such values can be used where appropriate with any of the other values, definitions, claims or embodiments defined hereinbefore or hereinafter.

In compounds of formula (I), $R^1$ is hydrogen or alkyl. Examples of the alkyl group for $R^1$ include, but are not limited to, methyl and ethyl.

$R^2$ is hydrogen, halogen, alkyl, haloalkyl, aryl, heteroaryl, cycloalkyl, or heterocycle, wherein each of the rings as represented by $R^2$ is independently unsubstituted or further substituted as described in the summary. In certain embodiments, $R^2$ is hydrogen, halogen, alkyl (for example, methyl, ethyl, and the like), or haloalkyl. In other embodiments, $R^2$ is hydrogen.

$R^3$ is cycloalkyl, aryl, heteroaryl, heterocycle, —(CR$^a$R$^b$)$_m$—R$^4$, —C(O)OR$^5$, —C(R$^5$)=N—O(R$^y$), —C(O)—R$^5$, or —C(O)—N(R$^5$)(R$^6$); wherein each of the rings is independently unsubstituted or further substituted, and the optional substituents, R$^a$, R$^b$, m, R$^4$, R$^5$, R$^6$, and R$^y$ are as defined in the summary.

In certain embodiments, $R^3$ is cycloalkyl (for example, cyclopropyl, cyclobutyl, cyclopentyl, cyclohexyl, bicyclo[2.2.1]heptyl, or cycloheptyl), or heterocycle (for example, morpholinyl, or tetrahydro, 2H-pyranyl), each of which is independently unsubstituted or further substituted as disclosed in the summary section. Particular examples of the optional substituents on the ring as represented by $R^3$ include, but are not limited to, C$_{1-6}$ alkyl (for example, methyl, ethyl, isopropyl, or tert-butyl), haloalkyl (for example, trifluoromethyl or difluoromethyl), halogen, oxo, —OR$^{10}$, —S(R$^{14}$), —S(O)$_2$R$^{15}$, —S(O)$_2$N(R$^{11}$)(R$^{12}$), —N(R$^{11}$)(R$^{12}$), —C(O)OR$^{10}$, —C(O)O(trialkylsilylalkyl), —C(O)N(R$^{11}$)(R$^{12}$), —(CR$^e$R$^f$)$_q$—OR$^{10}$, —(CR$^e$R$^f$)$_q$—N(R$^{11}$)(R$^{12}$), —(CR$^e$R$^f$)$_q$—C(O)OR$^{10}$, —(CR$^e$R$^f$)$_q$—C(O)N(R$^{11}$)(R$^{12}$), and =N—O(R$^{10}$), wherein R$^{10}$, R$^{11}$, R$^{12}$, R$^{14}$, R$^{15}$, R$^e$, R$^f$, and q are as defined in the summary section. For example, R$^{12}$, R$^e$, and R$^f$, at each occurrence, are each independently hydrogen or C$_{1-6}$ alkyl (for example, methyl, ethyl, isopropyl, or tert-butyl). R$^{10}$, at each occurrence, for example, is independently hydrogen, C$_{1-6}$ alkyl (for example, methyl, ethyl, isopropyl or tert-butyl), haloalkyl (for example, trifluoromethyl or difluoromethyl), —(CR$^g$R$^h$)$_r$C(O)OR$^{13}$, or phenyl (unsubstituted or substituted as described for G$^1$ in the summary), wherein R$^g$, R$^h$, and R$^{13}$ are each independently hydrogen or C$_{1-6}$ alkyl (for example, methyl, ethyl, isopropyl or tert-butyl, and the like), and r is 1, 2, 3, or 4, preferably, r is 1 or 2. R$^{11}$, at each occurrence, for example, is independently hydrogen, C$_{1-6}$ alkyl (for example, methyl, ethyl, isopropyl or tert-butyl), haloalkyl (for example, trifluoromethyl or difluoromethyl), —S(O)$_2$—R$^{13a}$, —S(O)$_2$—N(R$^{13}$)(R$^{14}$), —C(O)OR$^{13}$, or —C(O)N(R$^{13}$)(R$^{14}$) wherein R$^{13a}$, R$^{13}$, and R$^{14}$ are as disclosed in the summary, and q, at each occurrence; for example, is 1 or 2.

When $R^3$ is a substituted cycloalkyl or substituted heterocycle, one of the substituents can be attached to the same carbon that is connected to the alkynyl of general formula (I). Thus in certain embodiments, $R^3$ is formula (a),

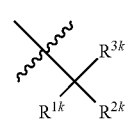

(a)

wherein R$^{1k}$ and R$^{2k}$ together with the carbon atom to which they are attached form a cycloalkyl ring (for example, cyclopropyl, cyclobutyl, cyclopentyl, cyclohexyl, bicyclo[2.2.1]heptyl, or cycloheptyl), or a heterocycle ring (for example, tetrahydro-2H-pyranyl), each of which is independently unsubstituted or further substituted as described in the Summary and in the preceding paragraph, and R$^{3k}$ is —OR$^{10}$—N(R$^{11}$)(R$^{12}$), —C(O)OR$^{10}$, or —C(O)O(trialkylsilylalkyl), wherein R$^{10}$, R$^{11}$ and R$^{12}$ are as defined in the summary. R$^{12}$, for example, is hydrogen or C$_{1-6}$ alkyl (for example, methyl; ethyl, isopropyl or tert-butyl). Particular example of R$^{10}$, at each occurrence, is independently hydrogen, C$_{1-6}$ alkyl (for example, methyl, ethyl, isopropyl or tert-butyl), haloalkyl (for example, trifluoromethyl or difluoromethyl), —(CR$^g$R$^h$)$_r$—C(O)OR$^{13}$, or phenyl (unsubstituted or substituted as described for G$^1$ in the summary), wherein R$^g$, R$^h$, and R$^{13}$, are, for example, each independently hydrogen or C$_{1-6}$ alkyl (for example, methyl, ethyl, isopropyl or tert-butyl), and r is 1, 2, 3, or 4, preferably, r is 1 or 2. $R^{11}$ is, for example, hydrogen, $C_{1-6}$ alkyl (for example, methyl, ethyl, isopropyl or tert-butyl), haloalkyl (for example, trifluoromethyl or difluoromethyl), —S(O)$_2$—R$^{13a}$, —S(O)$_2$—N(R$^{13}$)(R$^{14}$), —C(O)OR$^{13}$, or —C(O)N(R$^{13}$)(R$^{14}$) wherein R$^{13a}$, R$^{13}$ and R$^{14}$ are as disclosed in the summary. In certain embodiments, $R^{3k}$ is —OH or —OCH$_2$COOH. In yet other embodiments $R^{3k}$ is —NH$_2$ or —N(H)S(O)$_2$R$^{13a}$ wherein R$^{13a}$ is optionally substituted phenyl.

In yet other embodiments, $R^3$ is aryl (for example, phenyl), unsubstituted or substituted as described in the summary. Examples of the optional substituents on the aryl as represented by $R^3$ include, but are not limited to, alkyl such as $C_{1-6}$ alkyl (for example, methyl, ethyl, isopropyl or tert-butyl), haloalkyl (for example, trifluoromethyl or difluoromethyl), halogen, —OR$^{10}$, —S(R$^{14}$), —S(O)$_2$R$^{15}$, —S(O)$_2$N(R$^{11}$)(R$^{12}$), —N(R$^{11}$)(R$^{12}$), —C(O)OR$^{10}$, —C(O)O(trialkylsilylalkyl), —C(O)N(R$^{11}$)(R$^{12}$), —(CR$^e$R$^f$)$_q$—OR$^{10}$, —(CR$^e$R$^f$)$_q$—N(R$^{11}$)(R$^{12}$), —(CR$^e$R$^f$)$_q$—C(O)OR$^{10}$, —(CR$^e$R$^f$)$_q$—C(O)N(R$^{11}$)(R$^{12}$), and G$^1$, wherein G$^1$, R$^{10}$, R$^{11}$, R$^{12}$, R$^{14}$, R$^{15}$, R$^e$, R$^f$, and q are as defined in the summary section. For example, G$^1$ is aryl (for example, phenyl) or heteroaryl, each of which is optionally further substituted as described in the summary. R$^{12}$, R$^e$, and R$^f$, at each occurrence, for example, are each independently hydrogen or $C_{1-6}$ alkyl (for example, methyl, ethyl, isopropyl or tert-butyl). R$^{10}$, at each occurrence, for example, is independently hydrogen, $C_{1-6}$ alkyl (for example, methyl, ethyl, isopropyl, or tert-butyl), haloalkyl (for example, trifluoromethyl or difluoromethyl), —(CR$^g$R$^h$)$_r$C(O)OR$^{13}$, or phenyl (unsubstituted or substituted as described for G$^1$ in the summary), wherein R$^g$, R$^h$, and R$^{13}$ are, for example, each independently hydrogen or $C_{1-6}$ alkyl (for example, methyl, ethyl, isopropyl or tert-butyl), and r is 1, 2, 3, or 4, preferably, r is 1 or 2. R$^{11}$, at each occurrence, for example, is independently hydrogen, $C_{1-6}$ alkyl (for example, methyl, ethyl, isopropyl or tert-butyl), haloalkyl (for example, trifluoromethyl or difluoromethyl), —S(O)$_2$—R$^{13a}$, —S(O)$_2$—N(R$^{13}$)(R$^{14}$), —C(O)OR$^{13}$, or —C(O)N(R$^{13}$)(R$^{14}$) wherein R$^{13a}$, R$^{13}$, and R$^{14}$ are as disclosed in the summary. q, at each occurrence, for example, is independently 1 or 2. In certain embodiments, $R^3$ is phenyl, unsubstituted or further substituted as described in the Summary and in embodiments herein.

In still other embodiments, $R^3$ is —(CR$^a$R$^b$)$_m$)—R$^4$, wherein R$^a$, R$^b$, R$^4$, and in are as defined in the summary. In yet other embodiments, $R^3$ is —(CR$^a$R$^b$)$_m$—R$^4$, wherein R$^a$ and R$^b$, at each occurrence, are each independently hydrogen, alkyl (for example, $C_{1-6}$ alkyl such as methyl, ethyl, isopropyl or tert-butyl), alkenyl, halogen or haloalkyl (for example, trifluoromethyl or difluoromethyl), m is 1, 2, 3, or 4, and R$^4$ is cycloalkyl, aryl, heteroaryl, or heterocycle, each of which is optionally further substituted as described in the summary. In certain embodiments, m is 1 or 2. Examples of a subset of compounds described herein include, but are not limited to, those wherein $R^3$ is formula (b)

(b)

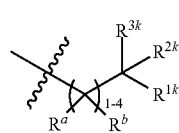

wherein R$^a$ and R$^b$, at each occurrence, are each independently hydrogen, halogen, alkyl such as $C_{1-6}$ alkyl (for example, methyl, ethyl, isopropyl, or tert-butyl), alkenyl, or haloalkyl (for example, trifluoromethyl or difluoromethyl), R$^{1k}$ and R$^{2k}$ together with the carbon atom to which they are attached form a cycloalkyl ring (for example, cyclopropyl, cyclobutyl, cyclopentyl, cyclohexyl, bicyclo[2.2.1]heptyl, or cycloheptyl), or a heterocycle ring (for example, terrahydro-2H-pyranyl), each of which is independently unsubstituted or further substituted as described for $R^3$ in the summary section, and $R^{3k}$ is —OR$^{10}$, —N(R$^{11}$)(R$^{12}$), —C(O)OR$^{10}$, or —C(O)O(trialkylsilylalkyl), wherein R$^{10}$, R$^{11}$, and R$^{12}$ are as defined in the summary. Examples of the optional substituents on the ring formed by R$^{1k}$, R$^{2k}$ and the carbon atom include, but are not limited to, $C_{1-6}$ alkyl (for example, methyl, ethyl, isopropyl, or tert-butyl), haloalkyl (for example, trifluoromethyl or difluoromethyl), halogen, oxo, —OR$^{10}$, —N(R$^{11}$)(R$^{12}$), —C(O)OR$^{10}$, —C(O)O(trialkylsilylalkyl), —C(O)N(R$^{11}$)(R$^{12}$), —(CR$^e$R$^f$)$_q$—OR$^{10}$, —(CR$^e$R$^f$)$_q$—N(R$^{11}$)(R$^{12}$), —(CR$^e$R$^f$)$_q$—C(O)OR$^{10}$, —(CR$^e$R$^f$)$_q$—C(O)N(R$^{11}$)(R$^{12}$), and =N—O(R$^{10}$), wherein R$^{10}$, R$^{11}$, R$^{12}$, R$^e$, R$^f$, and q are as defined in the summary section. For example, R$^{12}$, R$^e$, and R$^f$, at each occurrence, are each independently hydrogen or $C_{1-6}$ alkyl (for example, methyl, ethyl, isopropyl, or tert-butyl). For example, R$^{10}$, at each occurrence, is independently hydrogen, $C_{1-6}$ alkyl (for example, methyl, ethyl, isopropyl or tert-butyl), haloalkyl (for example, trifluoromethyl or difluoromethyl), —(CR$^g$R$^h$)$_r$—C(O)OR$^{13}$, or phenyl (unsubstituted or substituted as described for G$^1$ in the summary), wherein R$^g$, R$^h$, and R$^{13}$, are, for example, each independently hydrogen or $C_{1-6}$alkyl (for example, methyl, ethyl, isopropyl or tert-butyl), and r is 1, 2, 3, or 4, preferably, r is 1 or 2. R$^{11}$, at each occurrence, for example, is independently hydrogen, $C_{1-6}$ alkyl (for example, methyl, ethyl, isopropyl or tert-butyl), haloalkyl (for example, trifluoromethyl or difluoromethyl), —S(O)$_2$—R$^{13a}$, —S(O)$_2$—N(R$^{13}$)(R$^{14}$), C(O)OR$^{13}$, or —C(O)N(R$^{13}$)(R$^{14}$) wherein R$^{13}$, R$^{13a}$, and R$^{14}$ are as disclosed in the summary, and q, at each occurrence, for example, is 1 or 2.

In other embodiments, $R^3$ is formula (c)

(c)

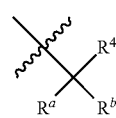

wherein R$^b$ is hydrogen, halogen, alkyl (for example, methyl, ethyl, isopropyl or tert-butyl), alkenyl, —C(O)OR$^{7b}$, haloalkyl (for example, trifluoromethyl or difluoromethyl), aryl (for example, phenyl), heteroaryl, cycloalkyl (for example, cyclopropyl, cyclobutyl, cyclopentyl, cyclohexyl or cycloheptyl), or heterocycle (for example, morpholinyl), wherein each of the aryl, heteroaryl, cycloalkyl, or heterocycle is independently unsubstituted or substituted as described in the summary section. Examples of the optional substituents of R$^b$ as a ring include, but are not limited to, $C_{1-6}$ alkyl, halogen, and haloalkyl. R$^a$ is OR$^{7a}$, N(R$^8$)(R$^9$), or —C(O)OR$^{7b}$, or R$^a$ and R$^b$ together is =CH$_2$, R$^4$ is hydrogen, alkyl (for example, methyl, ethyl, isopropyl or tert-butyl), haloalkyl, cycloalkyl (for example, cyclopropyl, cyclobutyl, cyclopentyl, cyclohexyl, cycloheptyl, or bicyclo[2.2.1]heptyl), aryl (for example, phenyl), heteroaryl, or heterocycle (for example, morpholinyl, tetrahydro-2H-pyranyl), wherein each of the rings as represented by R$^4$ is independently optionally further substituted as described in the summary, and R$^{7a}$, R$^{7b}$, R$^8$, and R$^9$ are as disclosed in the summary. For example, R$^{7a}$ is hydrogen, $C_{1-6}$ alkyl (for example, methyl, ethyl, isopropyl, or tert-butyl), haloalkyl (for example, trifluoromethyl or difluoromethyl), —(CR$^g$R$^h$)$_r$—C(O)OR$^{13}$ wherein R$^g$, R$^h$, R$^{13}$, and r are as described in the summary, or phenyl (unsubstituted or substituted as described in the summary). R$^{7b}$, R$^g$, R$^h$, R$^{13}$, and R$^9$, at each occurrence, for example, re each independently hydrogen, alkyl (for example, methyl, ethyl, isopropyl, or tert-butyl) or haloalkyl (for example, trifluoromethyl or difluoromethyl). r, for example, is 1 or 2. R$^8$, for example, is hydrogen, C$_{1-6}$ alkyl (for example, methyl, ethyl, isopropyl or tert-butyl), haloalkyl (for example, trifluoromethyl or difluoromethyl), —S(O)$_2$—R$^{13a}$, —S(O)$_2$—N(R$^{13}$)(R$^{14}$), —C(O)OR$^{13}$, or —C(O)N(R$^{13}$)(R$^{14}$) wherein R$^{13}$, R$^{13a}$, and R$^{14}$ are as disclosed in the summary.

In another embodiment, R$^3$ is formula (d)

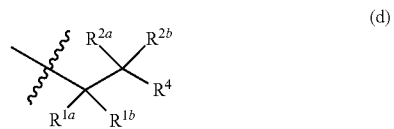

wherein R$^{1b}$ is hydrogen, alkyl (for example, methyl, ethyl, isopropyl or tert-butyl), alkenyl, halogen, —C(O)OR$^{7b}$, haloalkyl (for example, trifluoromethyl or difluoromethyl), aryl, heteroaryl, cycloalkyl (for example, cyclopropyl, Cyclobutyl, cyclopentyl or cyclohexyl), or heterocycle (for example, morpholinyl), R$^{1a}$ is OR$^{7a}$, N(R$^8$)(R$^9$) or —C(O)OR$^{7b}$, and R$^{2a}$ and R$^{2b}$, at each occurrence, are independently hydrogen, halogen, alkyl (for example, methyl, ethyl, isopropyl or tert-butyl), alkenyl, or haloalkyl (for example, trifluoromethyl or difluoromethyl); or R$^{2b}$ is hydrogen, alkyl (for example, methyl, ethyl, isopropyl or tert-butyl), alkenyl, halogen, —C(O)OR$^{7b}$, haloalkyl (for example, trifluoromethyl or difluoromethyl), aryl (for example, phenyl), heteroaryl, cycloalkyl (for example, cyclopropyl, cyclobutyl, cyclopentyl, or cyclohexyl), or heterocycle (for example, morpholinyl), R$^{2a}$ is OR$^{7a}$, N(R$^8$)(R$^9$) or —C(O)OR$^{7b}$, and R$^{1a}$ and R$^{1b}$, at each occurrence, are independently hydrogen, halogen, alkyl (for example, methyl, ethyl, isopropyl or tert-butyl), alkenyl, or haloalkyl (for example, trifluoromethyl or difluoromethyl); wherein each of the aryl, heteroaryl, cycloalkyl, or heterocycle as represented by R$^{1b}$ and R$^{2b}$ is independently unsubstituted or substituted as described for R$^b$ in the summary section. Examples of the optional substituents of R$^{1b}$ or R$^{2b}$ as a ring include, but are not limited to, C$_{1-6}$ alkyl, halogen, and haloalkyl. R$^4$ is hydrogen, alkyl, haloalkyl, cycloalkyl (for example, cyclopropyl, cyclobutyl, cyclopentyl, cyclohexyl, cycloheptyl, or bicyclo[2.2.1]heptyl), aryl (for example, phenyl), heteroaryl, or heterocycle (for example, tetrahydro-2H-pyranyl), wherein each of the cycloalkyl, aryl, heteroaryl, or heterocycle as represented by R$^4$ is independently optionally further substituted as described in the summary, and R$^{7a}$, R$^{7b}$, R$^8$, and R$^9$ are as disclosed in the summary. For example, R$^{7a}$, at each occurrence, is independently hydrogen, C$_{1-6}$ alkyl (for example, methyl, ethyl, isopropyl, or tert-butyl), haloalkyl (for example, trifluoromethyl or difluoromethyl), —(CR$^g$R$^h$)$_r$— C(O)OR$^{13}$ wherein R$^g$, R$^h$, R$^{13}$, and r are as described in the summary, or phenyl (unsubstituted or substituted as described in the summary). R$^{7b}$, R$^g$, R$^h$, R$^9$, R$^{13}$, and R$^9$, M each occurrence, are each independently hydrogen, C$_{1-6}$ alkyl (for example, methyl, ethyl, isopropyl, or tert-butyl) or haloalkyl (for example, trifluoromethyl or difluoromethyl). r, for example, is 1 or 2. R$^8$, at each occurrence, for example, is independently hydrogen, C$_{1-6}$ alkyl (for example, methyl, ethyl, isopropyl or tert-butyl), haloalkyl (for example, trifluoromethyl or difluoromethyl), —S(O)$_2$—R$^{13a}$, —S(O)$_2$—N(R$^{13}$)(R$^{14}$), —C(O)OR$^{13}$, or —C(O)N(R$^{13}$)(R$^{14}$) wherein R$^{13}$, R$^{13a}$, and R$^{14}$ are as disclosed in the summary.

In another embodiment, R$^3$ is —C(O)—R$^5$ wherein R$^5$ is as described in the summary. For example, R$^5$ is aryl such as phenyl, unsubstituted or further substituted as described in the summary.

It is appreciated that the present invention contemplates compounds of formula (I) with combinations of the above embodiments, including particular, more particular and preferred embodiments.

Accordingly, one aspect of the invention relates to compounds of formula (I) pharmaceutically acceptable salts, prodrugs, salts of prodrugs, or a combination thereof, wherein R$^2$ is hydrogen, halogen, alkyl, or haloalkyl, R$^3$ is aryl (for example, phenyl), unsubstituted or substituted as described in the summary. Examples of the optional substituents on the aryl as represented by R$^3$ include, but are not limited to; alkyl such as C$_{1-6}$ alkyl (for example, methyl, ethyl, isopropyl or tert-butyl), haloalkyl (for example, trifluoromethyl or difluoromethyl), halogen, —OR$^{10}$, —S(R$^{14}$), —S(O)$_2$R$^{15}$, —S(O)$_2$N(R$^{11}$)(R$^{12}$), —N(R$^{11}$)(R$^{12}$), —C(O)OR$^{10}$, —C(O)O(trialkylsilylalkyl), —C(O)N(R$^{11}$)(R$^{12}$), —(CR$^e$R$^f$)$_q$—OR$^{10}$, —(CR$^e$R$^f$)$_q$—N(R$^{11}$)(R$^{12}$), —(CR$^e$R$^f$)$_q$—C(O)OR$^{10}$, —(CR$^e$R$^f$)$_q$—C(O)N(R$^{11}$)(R$^{12}$), and G$^1$, wherein G$^1$, R$^{10}$, R$^{11}$, R$^{12}$, R$^{14}$, R$^{15}$, R$^e$, R$^f$, and q are as defined in the summary section. For example, G$^1$ is aryl (for example, phenyl) or heteroaryl, each of which is optionally further substituted as described in the summary. R$^{12}$, R$^e$, and R$^f$, at each occurrence, for example, are each independently hydrogen or C$_{1-6}$ alkyl (for example, methyl, ethyl, isopropyl or tert-butyl). R$^{10}$, at each occurrence, for example, is independently hydrogen, C$_{1-6}$ alkyl (for example, methyl, ethyl, isopropyl, or tert-butyl), haloalkyl (for example, trifluoromethyl or difluoromethyl), —(CR$^g$R$^h$)$_r$—C(O)OR$^{13}$, or phenyl (unsubstituted or substituted as described for G$^1$ in the summary), wherein R$^g$, R$^h$, and R$^{13}$ are, for example, each independently hydrogen or C$_{1-6}$ alkyl (for example, methyl, ethyl, isopropyl or tert-butyl), and r is 1, 2, 3, or 4, preferably, r is 1 or 2. R$^{11}$, at each occurrence, for example, is independently hydrogen, C$_{1-6}$ alkyl (for example, methyl, ethyl, isopropyl, or tert-butyl), haloalkyl (for example, trifluoromethyl or difluoromethyl), —S(O)$_2$—R$^{13a}$, —S(O)$_2$—N(R$^{13}$)(R$^{14}$), —C(O)OR$^{13}$, or —C(O)N(R$^{13}$)(R$^{14}$) wherein R$^{13a}$, R$^{13}$, and R$^{14}$ are, as disclosed in the summary. q, at each occurrence, for example, is independently 1 or 2. In certain embodiments, R$^3$ is phenyl, unsubstituted or further substituted as, described in the Summary and in embodiments herein. In certain embodiments, R$^2$ is hydrogen.

Another aspect of the invention relates to compounds of formula (I), or pharmaceutically acceptable salts, prodrugs, salts of prodrugs, or a combination thereof, wherein R$^3$ is cycloalkyl (for example, cyclopropyl, cyclobutyl, cyclopentyl, cyclohexyl, bicyclo[2.2.1]heptyl, or cycloheptyl), or heterocycle (for example, morpholinyl, or tetrahydro-2H-pyranyl), each of which is independently unsubstituted or further substituted as disclosed in the summary section, and R$^2$ is hydrogen, halogen, alkyl, or haloalkyl. Examples of the optional substituents on the ring as represented by R$^3$ include, but are not limited to, C$_{1-6}$ alkyl (for example, methyl, ethyl, isopropyl, or tert-butyl), haloalkyl (for example, trifluoromethyl or difluoromethyl), halogen, oxo, —OR$^{10}$, —S(R$^{14}$), —S(O)$_2$R$^{15}$, —S(O)$_2$N(R$^{11}$)(R$^{12}$), —N(R$^{11}$)(R$^{12}$), —C(O)OR$^{10}$, —C(O)O(trialkylsilylalkyl), —C(O)N(R$^{11}$)(R$^{12}$), —(CR$^e$R$^f$)$_q$—OR$^{10}$, —(CR$^e$R$^f$)$_q$—N(R$^{11}$)(R$^{12}$), —(CR$^e$R$^f$)$_q$—C(O)OR$^{10}$, —(CR$^e$R$^f$)$_q$—C(O)N(R$^{11}$)(R$^{12}$), and =N—O(R$^{10}$), wherein R$^{10}$, R$^{11}$, R$^{12}$, R$^{14}$, R$^e$, R$^f$ and q are as defined in the summary section. For example, R$^{12}$, R$^e$, and R$^f$, at each occurrence, are each independently hydrogen or C$_{1-6}$ alkyl (for example, methyl, ethyl, isopropyl, or tert-butyl). R$^{10}$, at each occurrence, for example, is independently hydrogen, C$_{1-6}$ alkyl (for example, methyl, ethyl, isopropyl or tert-butyl), haloalkyl (for example, trifluoromethyl or difluoromethyl), —(CR$^g$R$^h$)$_r$—C(O)OR$^{13}$, or phenyl (unsubstituted or substituted as described for G$^1$ in the summary), wherein R$^g$, R$^h$, and R$^{13}$ are each independently hydrogen or C$_{1-6}$ alkyl (for example, methyl, ethyl, isopropyl or tert-butyl, and the like), and r is 1, 2, 3, or 4, preferably, r is 1 or 2. R$^{11}$, at each occurrence, for example, is hydrogen, C$_{1-6}$ alkyl (for example, methyl, ethyl, isopropyl or tert-butyl), haloalkyl (for example, trifluoromethyl or difluoromethyl), —S(O)$_2$—R$^{13a}$, —S(O)$_2$—N(R$^{13}$)(R$^{14}$), —C(O)OR$^{13}$, or —C(O)N(R$^{13}$)(R$^{14}$) wherein R$^{13}$, R$^{13a}$, and R$^{14}$ are as disclosed in the summary, and q is, for example, 1 or 2. In certain embodiments, R$^2$ is hydrogen.

Of this group of compounds, examples of a subgroup include those wherein. R$^3$ is formula (a),

(a)

wherein R$^{1k}$ and R$^{2k}$ together with the carbon atom to which they are attached form a cycloalkyl ring (for example, cyclopropyl, cyclobutyl, cyclopentyl, cyclohexyl, bicyclo[2.2.1]heptyl, or cycloheptyl), or a heterocycle ring (for example, tetrahydro-2H-pyranyl), each of which is independently unsubstituted or further substituted as described in the preceding paragraph, R$^{3k}$ is —OR$^{10}$, —N(R$^{11}$)(R$^{12}$), —C(O)OR$^{10}$, or —C(O)O(trialkylsilylalkyl), wherein R$^{10}$, R$^{11}$ and R$^{12}$ are as defined in the summary, and R$^2$ is hydrogen, halogen, alkyl or haloalkyl. R$^{12}$, for example, is hydrogen or C$_{1-6}$ alkyl (for example, methyl, ethyl, isopropyl or tert-butyl). For example, R$^{10}$, at each occurrence, is independently hydrogen, C$_{1-6}$ alkyl (for example, methyl, ethyl, isopropyl or tert-butyl), haloalkyl (for example, trifluoromethyl or difluoromethyl), —(CR$^g$R$^h$)$_r$—C(O)OR$^{13}$, or phenyl (unsubstituted or substituted as described for G$^1$ in the summary), wherein R$^g$, R$^h$, and R$^{13}$, are, for example, each independently hydrogen or C$_{1-6}$ alkyl (for example, methyl, ethyl, isopropyl or tert-butyl), and r is 1, 2, 3, or 4, preferably, r is 1 or 2. R$^{11}$ is, for example, hydrogen, C$_{1-6}$ alkyl (for example, methyl, ethyl, isopropyl or tert-butyl), haloalkyl (for example, trifluoromethyl or difluoromethyl), —S(O)$_2$—R$^{13a}$, —S(O)$_2$—N(R$^{13}$)(R$^{14}$), —C(O)OR$^{13}$, or —C(O)N(R$^{13}$)(R$^{14}$) wherein R$^{13}$, R$^{13a}$, and R$^{14}$ are as disclosed in the summary. In certain embodiments, R$^2$ is hydrogen. In certain embodiments, R$^{3k}$ is —OH or —OCH$_2$COOH. In yet other embodiments R$^{3k}$ is —NH$_2$ or —N(H)S(O)$_2$R$^{13a}$ wherein R$^{13a}$ is optionally substituted phenyl.

Another aspect of the invention is directed to compounds of formula (I), or pharmaceutically acceptable salts, prodrugs, salts of prodrugs, of a combination thereof, wherein R$^3$ is aryl (for example, phenyl), unsubstituted or substituted as described in the summary, and 1 is hydrogen, halogen, alkyl, or haloalkyl. Examples of the optional substituents on the aryl as represented by R$^3$ include, but are not limited to, alkyl such as C$_{1-6}$ alkyl (for example, methyl, ethyl, isopropyl or tert-butyl), haloalkyl (for example, trifluoromethyl or difluoromethyl), halogen, —OR$^{10}$, —S(R$^{14}$), —S(O)$_2$R$^{15}$, —S(O)$_2$N(R$^{11}$)(R$^{12}$), —N(R$^{11}$)(R$^{12}$), —C(O)OR$^{10}$, —C(O)O(trialkylsilylalkyl), —C(O)N(R$^{11}$)(R$^{12}$), —(CR$^e$R$^f$)$_q$—OR$^{10}$, —(CR$^e$R$^f$)$_q$—N(R$^{11}$)(R$^{12}$), —(CR$^e$R$^f$)$_q$—C(O)OR$^{10}$, —(CR$^e$R$^f$)$_q$—C(O)N(R$^{11}$)(R$^{12}$), and G$^1$, wherein G$^1$, R$^{10}$, R$^{11}$, R$^{12}$, R$^{14}$, R$^{15}$, R$^e$, R$^f$, and q are as defined in the summary section. For example, G$^1$ is aryl (for example, phenyl) or heteroaryl, each of which is optionally further substituted as described in the summary. R$^{12}$, R$^e$, and R$^f$, at each occurrence, for example, are each independently hydrogen or C$_{1-6}$ alkyl (for example, methyl, ethyl, isopropyl or tert-butyl). R$^{10}$, at each occurrence, for example, is independently hydrogen, C$_{1-6}$ alkyl (for example, methyl, ethyl, isopropyl, or tert-butyl), haloalkyl (for example, trifluoromethyl or difluoromethyl), —(CR$^g$R$^h$)$_r$—C(O)OR$^{13}$, or phenyl (unsubstituted or substituted as described for G$^1$ in the summary), wherein R$^g$, R$^h$, R$^{13}$ are, for example, each independently hydrogen or C$_{1-6}$ alkyl (for example, methyl, ethyl, isopropyl or tert-butyl), and r is 1, 2, 3, or 4, preferably, r is 1 or 2. R$^{11}$, at each occurrence, for example, is independently hydrogen, C$_{1-6}$ alkyl (for example, methyl, ethyl, isopropyl or tert-butyl), haloalkyl (for example, trifluoromethyl or difluoromethyl), —S(O)$_2$—R$^{13a}$, —S(O)$_2$—N(R$^{13}$)(R$^{14}$), —C(O)OR$^{13}$, or —C(O)N(R$^{13}$)(R$^{14}$) wherein R$^{13}$, R$^{13a}$, and R$^{14}$ are as disclosed in the summary. q, at each occurrence, for example, is independently 1 or 2. In certain embodiments, R$^2$ is hydrogen. In certain embodiments, R$^3$ is phenyl, optionally substituted as described in the Summary and in embodiments herein.

Yet another aspect of the invention relates to compounds of formula (I), or pharmaceutically acceptable salts, prodrugs, salts of prodrugs, or a combination thereof, wherein R$^3$ is —(CR$^a$R$^b$)$_m$—R$^4$, wherein R$^a$, at each occurrence, is independently hydrogen, halogen, alkyl, alkenyl, haloalkyl, —OR$^{7a}$, —N(R$^8$)(R$^9$), —C(O)OR$^{7b}$, —C(O)—R$^{7b}$, —C(O)—N(R$^8$)(R$^9$), —(CR$^c$R$^d$)$_p$—OR$^{7a}$, —(CR$^c$R$^d$)$_p$—N(R$^8$)(R$^9$), —(CR$^c$R$^d$)$_p$—C(O)OR$^{7b}$, —(CR$^c$R$^d$)$_p$—C(O)—R$^{7b}$, —(CR$^c$R$^d$)$_p$—C(O)—N(R$^8$)(R$^9$), aryl, heteroaryl, cycloalkyl, or heterocycle; R$^b$, at each occurrence, is independently hydrogen, halogen, alkyl, alkenyl, haloalkyl, —C(O)OR$^{7b}$, —C(O)—R$^{7b}$, —C(O)—N(R$^8$)(R$^9$), —(CR$^c$R$^d$)$_p$—OR$^{7a}$, —(CR$^c$R$^d$)$_p$—N(R$^8$)(R$^9$), —(CR$^c$R$^d$)$_p$—C(O)OR$^{7b}$, —(CR$^c$R$^d$)$_p$—C(O)—R$^{7b}$, —(CR$^c$R$^d$)$_p$—C(O)—N(R$^8$)(R$^9$), aryl, heteroaryl, cycloalkyl, or heterocycle, or R$^a$ and R$^b$ together is =CH$_f$. Wherein each of the rings as represented by R$^a$ and R$^b$ are independently unsubstituted or further substituted as described in the summary, R$^4$ is hydrogen, alkyl, haloalkyl, Cycloalkyl, aryl, heteroaryl, or heterocycle, wherein each of the cycloalkyl, aryl, heteroaryl, or heterocycle is independently optionally substituted as described in the summary, with the proviso that when R$^4$ is hydrogen, alkyl, or haloalkyl, then at least one R$^a$ is —OR$^{7a}$, —N(R$^8$)(R$^9$), —C(O)OR$^{7b}$, —C(O)—R$^{7b}$, —C(O)—N(R$^8$)(R$^9$), —(CR$^c$R$^d$)$_p$—OR$^{7a}$, —(CR$^c$R$^d$)$_p$—N(R$^8$)(R$^9$), —(CR$^c$R$^d$)$_p$—C(O)OR$^{7b}$, —(CR$^c$R$^d$)$_p$—C(O)—R$^{7b}$, or —(CR$^c$R$^d$)$_p$—C(O)—N(R$^8$)(R$^9$), or R$^a$ and R$^b$ together is =CH$_2$; R$^2$ is hydrogen, halogen, alkyl or haloalkyl, and m, p, R$^c$, R$^d$, R$^{7a}$, R$^{7b}$, R$^8$, and R$^9$ are as disclosed in the summary. In one embodiment, R$^2$ is hydrogen.

Of this group of compounds, examples include those wherein R$^3$ is —(CR$^a$R$^b$)$_m$—R$^4$, wherein R$^a$ and R$^b$, at each occurrence, are each independently hydrogen, alkyl (for example, C$_{1-6}$ alkyl such as methyl, ethyl, isopropyl or tert-butyl), alkenyl, halogen or haloalkyl (for example, trifluoromethyl or difluoromethyl); m is 1, 2, 3 or 4, and R$^4$ is, cycloalkyl (for example, cyclopropyl, cyclobutyl, cyclopentyl, cyclohexyl, bicyclo[2.2.1]heptyl, or cycloheptyl), aryl (for example, phenyl), heteroaryl, or heterocycle (for example, tetrahydro-2H-pyranyl), each of which is optionally further substituted as described in the summary. In certain embodiments, m is 1 or 2.

Of this group of compounds, other examples include those wherein $R^3$ is of formula (b)

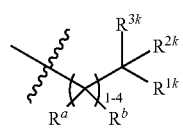

(b)

wherein $R^a$ and $R^b$, at each occurrence, are each independently hydrogen, halogen, alkyl (for example, $C_{1-6}$ alkyl such as methyl, ethyl, isopropyl, or tert-butyl), alkenyl, or haloalkyl (for example, trifluoromethyl or difluoromethyl), $R^{1k}$ and $R^{2n}$ together with the carbon atom to which they are attached form a cycloalkyl ring (for example, cyclopropyl, cyclobutyl, cyclopentyl, cyclohexyl, bicyclo[2.2.1]heptyl, or cycloheptyl), or a heterocycle ring (for example, tetrahydro-2H-pyranyl), each of which is independently unsubstituted or further substituted as described for $R^3$ in the summary section, $R^{3k}$ is $-OR^{10}$, $-N(R^{11})(R^{12})$, $-C(O)OR^{10}$, or $-C(O)O(\text{trialkylsilylalkyl})$, $R^2$ is hydrogen, halogen, alkyl, or haloalkyl, and $R^{10}$, $R^{11}$ and $R^{12}$ are as defined in the summary. Examples of the optional substituents on the ring formed by $R^{1k}$, $R^{2k}$ and the carbon atom include, but are not limited to, $C_{1-6}$ alkyl (for example, methyl, ethyl, isopropyl, or tert-butyl), haloalkyl (for example, trifluoromethyl or difluoromethyl), halogen, oxo, $-OR^{10}$, $-N(R^{11})(R^{12})$, $-C(O)OR^{10}$, $-C(O)OR(\text{trialkylsilylalkyl})$, $-C(O)N(R^{11})(R^{12})$, $-(CR^eR^f)_q-OR^{10}$, $-(CR^eR^f)_q-N(R^{11})(R^{12})$, $-(CR^eR^f)_q-C(O)OR^{10}$, $-(CR^eR^f)_q-C(O)N(R^{11})(R^{12})$, and $=N-O(R^{10})$, wherein $R^{10}$, $R^{11}$, $R^{12}$, $R^e$, $R^f$, and q are as defined in the summary section. $R^{12}$, at each occurrence, for example, is independently hydrogen or $C_{1-6}$ alkyl (for example, methyl, ethyl, isopropyl or tert-butyl). For example, $R^{10}$, at each occurrence, is independently hydrogen, $C_{1-6}$ alkyl (for example, methyl, ethyl, isopropyl or tert-butyl), haloalkyl (for example, trifluoromethyl or difluoromethyl), $-(CR^gR^h)_r-C(O)OR^{13}$, or phenyl (unsubstituted or substituted as described for $G^1$ in the summary), wherein $R^g$, $R^h$, and $R^{13}$, are, for example, each independently hydrogen or $C_{1-6}$ alkyl (for example, methyl, ethyl, isopropyl or tert-butyl), and r is 1, 2, 3, or 4, preferably, r is 1 or 2. $R^{11}$, at each occurrence, for example, is independently hydrogen, $C_{1-6}$ alkyl (for example, methyl, ethyl, isopropyl or tert-butyl), haloalkyl (for example, trifluoromethyl or difluoromethyl), $-S(O)_2-R^{13a}$, $-S(O)_2-N(R^{13})(R^{14})$, $-C(O)OR^{13}$, or $-C(O)N(R^{13})(R^{14})$ wherein $R^{13}$, $R^{13a}$, and $R^{14}$ are as disclosed in the summary, and q, at each occurrence, for example, is independently 1 or 2. In certain embodiments, $R^2$ is hydrogen.

Other examples of this group of compounds include those wherein $R^3$ is formula (c)

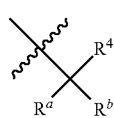

(c)

wherein $R^b$ is hydrogen, halogen, alkyl (for example, alkyl such as methyl, ethyl, isopropyl or tert-butyl), alkenyl, $-C(O)OR^{7b}$, haloalkyl (for example, trifluoromethyl or difluoromethyl), aryl (for example, phenyl), heteroaryl, cycloalkyl (for example, cyclopropyl, cyclobutyl, cyclopentyl, cyclohexyl or cycloheptyl), or heterocycle (for example, morpholinyl), wherein each of the aryl, heteroaryl, cycloalkyl, or heterocycle is independently unsubstituted or substituted as described in the summary section, $R^a$ is $OR^{7a}$, $N(R^8)(R^9)$, or $-C(O)OR^{7b}$, or $R^a$ and $R^b$ together is $=CH_2$; $R^4$ is hydrogen, alkyl (for example, $C_{1-6}$ alkyl such as methyl, ethyl, isopropyl or tert-butyl), haloalkyl, cycloalkyl (for example, cyclopropyl, cyclobutyl, cyclopentyl, cyclohexyl, cycloheptyl, or bicyclo[2.2.1]heptyl), aryl (for example, phenyl), heteroaryl, or heterocycle (for example, tetrahydro-2H-pyranyl), wherein each of the rings as represented by $R^4$ is independently optionally further substituted as described in the summary and in embodiments hereinabove, and $R^{7a}$, $R^{7b}$, $R^8$, and $R^9$ are as disclosed in the summary. Examples of the optional substituents of $R^b$ as a ring include, but are not limited to, $C_{1-6}$ alkyl, halogen, and haloalkyl. $R^{7a}$ is, for example, hydrogen, $C_{1-6}$ alkyl (for example, methyl, ethyl, isopropyl, or tert-butyl), haloalkyl (for example, trifluoromethyl or difluoromethyl), $-(CR^gR^h)_r-C(O)OR^{13}$ wherein $R^g$, $R^h$, $R^{13}$, and r are as described in the summary, or phenyl (unsubstituted or substituted as described in the summary). $R^{7b}$, $R^g$, $R^h$, $R^{13}$, and $R^9$, at each occurrence, for example, are each independently hydrogen, $C_{1-6}$ alkyl (for example, methyl, ethyl, isopropyl, or tert-butyl) or haloalkyl (for example, trifluoromethyl or difluoromethyl). r, for example, is 1 or 2. $R^8$, for example, is hydrogen, $C_{1-6}$ alkyl (for example, methyl, ethyl, isopropyl or tert-butyl), haloalkyl (for example, trifluoromethyl or difluoromethyl), $-S(O)_2-R^{13a}$, $-S(O)_2-N(R^{13})(R^{14})$, $-C(O)OR^{13}$, or $-C(O)N(R^{13})(R^{14})$ wherein $R^{13}$, $R^{13a}$, and $R^{14}$ are as disclosed in the summary.

Yet other examples of this group of compounds include those wherein $R^3$ is formula (d)

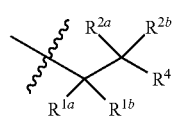

(d)

wherein $R^{1b}$ is hydrogen, alkyl (for example, $C_{1-6}$ alkyl such as methyl, ethyl, isopropyl or tert-butyl), alkenyl, halogen, $-C(O)OR^{7b}$, haloalkyl (for example, trifluoromethyl or difluoromethyl), aryl, heteroaryl, cycloalkyl (for example, cyclopropyl, cyclobutyl, cyclopentyl or cyclohexyl), or heterocycle (for example, morpholinyl); $R^{1a}$ is $OR^{7a}$, $N(R^8)(R^9)$ or $-C(O)OR^{7b}$, and $R^{2a}$ and $R^{2b}$, at each occurrence, are independently hydrogen, halogen, alkyl (for example, methyl, ethyl, isopropyl or tert-butyl), alkenyl, or haloalkyl (for example, trifluoromethyl or difluoromethyl); or $R^{2b}$ is hydrogen, alkyl (for example, methyl, ethyl, isopropyl or tert-butyl), alkenyl, halogen, $-C(O)OR^{7b}$, haloalkyl (for example, trifluoromethyl or difluoromethyl), aryl (for example, phenyl), heteroaryl, cycloalkyl (for example, cyclopropyl, cyclobutyl, cyclopentyl, or cyclohexyl), or heterocycle (for example; morpholinyl), $R^{2a}$ is $OR^{7a}$, $N(R^8)(R^9)$ or $-C(O)OR^{7b}$, and $R^{1a}$ and $R^{1b}$, at each occurrence, are each independently hydrogen, halogen, alkyl (for example, $C_{1-6}$ alkyl such as methyl, ethyl, isopropyl or tert-butyl), alkenyl, or haloalkyl (for example, trifluoromethyl or difluoromethyl);

wherein each of the aryl heteroaryl, cycloalkyl, or heterocycle as represented by $R^{1b}$ and $R^{2b}$ is independently unsubstituted or further substituted as those listed for the rings represented by $R^b$ in the summary section. Examples of the optional substituents of $R^{1b}$ or $R^{2b}$ as a ring include, but are not limited to, $C_{1-6}$ alkyl, halogen, and haloalkyl. $R^4$ is hydrogen, alkyl, haloalkyl, cycloalkyl (for example, cyclopropyl, cyclobutyl, cyclopentyl, cyclohexyl, cycloheptyl, or bicyclo[2.2.1]heptyl), aryl (for example, phenyl), heteroaryl, or heterocycle (for example, tetrahydro-2H-pyranyl), wherein each of the rings as represented by $R^4$ is independently optionally further substituted as described in the summary, and $R^{7a}$, $R^{7b}$, $R^8$, and $R^9$ are as disclosed in the summary. For example, $R^{7a}$, at each occurrence, is independently hydrogen, $C_{1-6}$ alkyl (for example, methyl, ethyl, isopropyl, or tert-butyl), haloalkyl (for example, trifluoromethyl or difluoromethyl), $-(CR^gR^h)_r-C(O)OR^{13}$ wherein $R^g$, $R^h$, $R^{13}$, and r are as described in the summary, or phenyl (unsubstituted or substituted as described in the summary). $R^{7b}$, $R^g$, $R^h$, $R^{13}$, and $R^9$, at, each occurrence, for example, are each independently hydrogen, $C_{1-6}$ alkyl (for example, methyl, ethyl, isopropyl, or tert-butyl) or haloalkyl (for example, trifluoromethyl or difluoromethyl). r; for example, is 1 or 2. $R^8$, at each occurrence, for example, is independently hydrogen, $C_{1-6}$ alkyl (for example, methyl, ethyl, isopropyl or tert-butyl), haloalkyl (for example, trifluoromethyl or difluoromethyl), $-S(O)_2-R^{13a}$, $-S(O)_2-N(R^{13})(R^{14})$, $-C(O)OR^{13}$, or $-C(O)N(R^{13})(R^{14})$ wherein $R^{13}$, $R^{13a}$, and $R^{14}$ are as disclosed in the summary.

Yet another aspect of the invention relates to compounds of formula (I), or pharmaceutically acceptable salts, prodrugs, salts of prodrugs, or a combination thereof; wherein $R^3$ is $-C(O)-R^5$, $R^2$ is hydrogen, halogen, alkyl, or haloalkyl, and $R^5$ is as disclosed in the summary. For example, $R^5$ is aryl such as phenyl, optionally further substituted as described in the summary. In certain embodiments, $R^2$ is hydrogen.

Exemplary compounds of the present invention include, but are not limited to the following:
6-[(4-aminophenyl)ethynyl]-5-methyl[1,2,4]triazolo[1,5-a]pyrimidin-7-amine;
6-(cyclohexylethynyl)-5-methyl[1,2,4]triazolo[1,5-a]pyrimidin-7-amine;
5-methyl-6-(4-phenylbut-1-ynyl)[1,2,4]triazolo[1,5-a]pyrimidin-7-amine;
1-[(7-amino-5-methyl[1,2,4]triazolo[1,5-a]pyrimidin-6-yl)ethynyl]cyclopentanol;
1-[(7-amino-5-methyl[1,2,4]triazolo[1,5-a]pyrimidin-6-yl)ethynyl]cyclohexanol;
4-[(7-amino-5-methyl[1,2,4]triazolo[1,5-a]pyrimidin-6-yl)ethynyl]tetrahydro-2H-pyran-4-ol;
4-(7-amino-5-methyl[1,2,4]triazolo[1,5-a]pyrimidin-6-yl)-2-cyclopentylbut-3-yn-2-ol;
4-(7-amino-5-methyl[1,2,4]triazolo[1,5-a]pyrimidin-6-yl)-2-phenylbut-3-yn-2-ol;
4-(7-amino-5-methyl[1,2,4]triazolo[1,5-a]pyrimidin-6-yl)-1,1,1-trifluoro-2-phenylbut-3-yn-2-ol;
3-(7-amino-5-methyl[1,2,4]triazolo[1,5-a]pyrimidin-6-yl)-1,1-diphenylprop-2-yn-1ol;
3-(7-amino-5-methyl[1,2,4]triazolo[1,5-a]pyrimidin-6-yl)-1-phenylprop-2-yn-1-ol;
6-(3-cyclohexylprop-1-ynyl)-5-methyl[1,2,4]triazolo[1,5-a]pyrimidin-7-amine;
3-(7-amino-5-methyl[1,2,4]triazolo[1,5-a]pyrimidin-6-yl)-1-cyclopropyl-1-phenylprop-2-yn-1-ol;
6-[(4-methoxyphenyl)ethynyl]-5-methyl[1,2,4]triazolo[1,5-a]pyrimidin-7-amine;
3-(7-amino-5-methyl[1,2,4]triazolo[1,5-a]pyrimidin-6-yl)-1,1-bis(4-chlorophenyl)prop-2-yn-1-ol;
5-methyl-6-(3-morpholin-4-yl-3-phenylprop-1-ynyl)[1,2,4]triazolo[1,5-a]pyrimidin-7-amine;
3-(7-amino-5-methyl[1,2,4]triazolo[1,5-a]pyrimidin-6-yl)-1-(1-methylcyclohexyl)-1-phenylprop-2-yn-1-ol;
3-(7-amino-5-methyl[1,2,4]triazolo[1,5-a]pyrimidin-6-yl)-1-(3,4'-dichloro-1,1'-biphenyl-4-yl)prop-2-yn-1-ol;
1-(7-amino-5-methyl[1,2,4]triazolo[1,5-a]pyrimidin-6-yl)-3-(1,1'-biphenyl-4-yl)-4,4-dimethylpent-1-yn-3-ol;
methyl 4-(7-amino-5-methyl[1,2,4]triazolo[1,5-a]pyrimidin-6-yl)-2-hydroxy-2-phenylbut-3-ynoate;
N-{1-[(7-amino-5-methyl[1,2,4]triazolo[1,5-a]pyrimidin-6-yl)ethynyl]cyclohexyl}-3-chlorobenzenesulfonamide;
N-{4-[(7-amino-5-methyl[1,2,4]triazolo[1,5-a]pyrimidin-6-yl)ethynyl]phenyl}-N'-(3-chlorophenyl)urea;
(1R,4R)-2-[(7-amino-5-methyl[1,2,4]triazolo[1,5-a]pyrimidin-6-yl)ethynyl]-1,7,7-trimethylbicyclo[2.2.1]heptan-2-ol;
(1Z)-2-[3-(7-amino-5-methyl[1,2,4]triazolo[1,5-a]pyrimidin-6-yl)prop-2-ynyl]-4-tert-butylcyclohexanone oxime;
4-(7-amino-5-methyl[1,2,4]triazolo[1,5-a]pyrimidin-6-yl)-2-(4-isopropyl-2-methylcyclopentyl)but-3-yn-2-ol;
methyl {[3-(7-amino-5-methyl[1,2,4]triazolo[1,5-a]pyrimidin-6-yl)-1-phenylprop-2-ynyl]oxy}acetate;
{[3-(7-amino-5-methyl[1,2,4]triazolo[1,5-a]pyrimidin-6-yl)-1-phenylprop-2-ynyl]oxy}acetic acid;
{2-[(7-amino-5-methyl[1,2,4]triazolo[1,5-a]pyrimidin-6-yl)ethynyl]phenyl}methanol;
{3-[3-(7-amino-5-methyl[1,2,4]triazolo[1,5-a]pyrimidin-6-yl)-1-hydroxy-1-methylprop-2-ynyl]-2,2-dimethylcyclobutyl}acetic acid;
4-(7-amino-5-methyl[1,2,4]triazolo[1,5-a]pyrimidin-6-yl)-2-cyclobutylbut-3-yn-2-ol;
4-(7-amino-5-methyl[1,2,4]triazolo[1,5a]pyrimidin-6-yl)-2-(3-methylcylobutyl)but-3-yn-2-ol;
5-methyl-6-(3-phenylprop-1-ynyl)[1,2,4]triazolo[1,5-a]pyrimidin-7-amine
6-(3-cyclopentylprop-1-ynyl)-5-methyl[1,2,4]triazolo[1,5-a]pyrimidin-7-amine;
6-[(1-aminocyclohexyl)ethynyl]-5-methyl[1,2,4]triazolo[1,5-a]pyrimidin-7-amine;
3-(7-amino-5-methyl[1,2,4]triazolo[1,5-a]pyrimidin-6-yl)-yl-cyclopentylprop-2-yn-1-ol;
3-(7-amino-5-methyl[1,2,4]triazolo[1,5-a]pyrimidin-6-yl)-1-(2,4-dichlorophenyl)prop-2-yn-1-ol;
4-(1-amino-5-methyl[1,2,4]triazolo[1,5-a]pyrimidin-6-yl)-1-cyclopentyl-2-methylbut-3-yn-2-ol;
{4-[(7-amino-5-methyl[1,2,4]triazolo[1,5-a]pyrimidin-6-yl)ethynyl]-4-hydroxycyclohexyl}acetic acid;
methyl {4-[(7-amino-5-methyl[1,2,4]triazolo[1,5-a]pyrimidin-6-yl)ethynyl]-4-hydroxycyclohexyl}acetate;
(1R,4S)-2-[(7-amino-5-methyl[1,2,4]triazolo[1,5-a]pyrimidin-6-yl)ethynyl]bicyclo[2.2.1]heptan-2-ol;
(1R,2S,4R)-2-[(7-amino-5-methyl[1,2,4]triazolo[1,5-a]pyrimidin-6-yl)ethynyl]-1,7,7-trimethylbicyclo[2.2.1]heptan-2-ol;
(1R,2R,4S)-2-[(7-amino-5-methyl[1,2,4]triazolo[1,5-a]pyrimidin-6-yl)ethynyl]-1,3,3-trimethylbicyclo[2.2.1]heptan-2-ol;
tert-butyl {4-[(7-amino-5-methyl[1,2,4]triazolo[1,5-a]pyrimidin-6-yl)ethynyl]-4-hydroxycyclohexyl}acetate;
(1S,2S,4R)-2-[(7-amino-5-methyl[1,2,4]triazolo[1,5-a]pyrimidin-6-yl)ethynyl]-1,3,3-trimethylbicyclo[2.2.1]heptan-2-ol;

(1S,2R,4S)-2-[(7-amino-5-methyl[1,2,4]triazolo[1,5-a]pyrimidin-6-yl)ethynyl]-1,7,7-trimethylbicyclo[2.2.1]heptan-2-ol;
1-[3-(7-amino-5-methyl[1,2,4]triazolo[1,5-a]pyrimidin-6-yl)prop-2-ynyl]cyclopentanol;
1-[(7-amino[1,2,4]triazolo[1,5-a]pyrimidin-6-yl)ethynyl]cyclopentanol;
1-[3-(7-amino[1,2,4]triazolo[1,5-a]pyrimidin-6-yl)prop-2-ynyl]cyclopentanol;
(1R,2S,4R)-2-[3-(7-amino-5-methyl[1,2,4]triazolo[1,5-a]pyrimidin-6-yl)prop-2-ynyl]-1,7,7-trimethylbicyclo[2.2.1]heptan-2-ol;
methyl 1-[3-(7-amino-5-methyl[1,2,4]triazolo[1,5-a]pyrimidin-6-yl)prop-2-ynyl]cyclohexanecarboxylate;
6-[3-(4-methoxyphenoxy)but-1-ynyl]-5-methyl[1,2,4]triazolo[1,5-a]pyrimidin-7-amine;
(1R)-3-(7-amino-5-methyl[1,2,4]triazolo[1,5-a]pyrimidin-6-yl)-1-phenylprop-2-yn-1-ol;
(1S)-3-(7-amino-5-methyl[1,2,4]triazolo[1,5-a]pyrimidin-6-yl)-1-phenylprop-2-yn-1-ol;
4-(7-amino-5-methyl[1,2,4]triazolo[1,5-a]pyrimidin-6-yl)-1-phenylbut-3-yn-1-ol;
(trans)-ethyl 2-[3-(7-amino-5-methyl[1,2,4]triazolo[1,5-a]pyrimidin-6-yl)-1-hydroxyprop-2-ynyl]cyclopropanecarboxylate;
1-[3-(7-amino-5-methyl[1,2,4]triazolo[1,5-a]pyrimidin-6-yl)prop-2-ynyl]cyclohexanecarboxylic acid;
1-[(7-amino-5-ethyl[1,2,4]triazolo[1,5-a]pyrimidin-6-yl)ethynyl]cyclopentanol;
3-(7-amino-5-Methyl[1,2,4]triazolo[1,5-a]pyrimidin-6-yl)-1-phenylprop-2-yn-1-one;
2-{3-[3-(7-amino-5-methyl[1,2,4]triazolo[1,5-a]pyrimidin-6-yl)-1-hydroxy-1-methylprop-2-ynyl]-2,2-dimethylcyclobutyl}acetamide;
(1R,2S,4R)-2-[(7-amino-5-ethyl[1,2,4]triazolo[1,5-a]pyrimidin-6-yl)ethynyl]-1,7,7-trimethyl bicyclo[2.2.1]heptan-2-ol;
1-[(7-amino-5-methyl[1,2,4]triazolo[1,5-a]pyrimidin-6-yl)ethynyl]cycloheptanol;
{[3-(7-amino-5-methyl[1,2,4]triazolo[1,5-a]pyrimidin-6-yl)-1-cyclopentylprop-2-ynyl]oxy}acetic acid;
({1-[(7-amino-5-methyl[1,2,4]triazolo[1,5-a]pyrimidin-6-yl)ethynyl]cyclopentyl}oxy)acetic acid;
3-(7-amino-5-methyl[1,2,4]triazolo[1,5-a]pyrimidin-6-yl)-1-cyclohexylprop-2-yn-1-ol;
methyl 4-[3-(7-amino-5-methyl[1,2,4]triazolo[1,5-a]pyrimidin-6-yl)-1-hydroxyprop-2-ynyl]cyclohexanecarboxylate;
4-[3-(7-amino-5-methyl[1,2,4]triazolo[1,5-a]pyrimidin-6-yl)-1-hydroxyprop-2-ynyl]cyclohexanecarboxylic acid;
{3-[3-(7-amino-5-methyl[1,2,4]triazolo[1,5-a]pyrimidin-6-yl)-1-methyleneprop-2-ynyl]-2,2-dimethylcyclobutyl}acetic acid;
methyl 1-[3-(7-amino-5-methyl[1,2,4]triazolo[1,5-a]pyrimidin-6-yl)prop-2-ynyl]cyclopentanecarboxylate;
2-(trimethylsilyl)ethyl 1-[3-(7-amino-5-methyl[1,2,4]triazolo[1,5-a]pyrimidin-6-yl)prop-2-ynyl]cyclohexanecarboxylate;
6-[(4-bromophenyl)ethynyl]-5-methyl[1,2,4]triazolo[1,5-a]pyrimidin-7-amine;
6-[(4-chlorophenyl)ethynyl]-5-methyl[1,2,4]triazolo[1,5-a]pyrimidin-7-amine;
methyl 2-{4-[(7-amino-5-methyl[1,2,4]triazolo[1,5-a]pyrimidin-6-yl)ethynyl]phenyl}-2-methylpropanoate;
ethyl 1-[4-(7-amino-5-methyl[1,2,4]triazolo[1,5-a]pyrimidin-6-yl)but-3-ynyl]-2-oxocyclopentanecarboxylate; and
a pharmaceutically acceptable salt, prodrug, or salt of a prodrug thereof.

Compounds disclosed herein can contain asymmetrically substituted carbon or sulfur atoms, and accordingly can exist in, and be isolated in, single stereoisomers (e.g. single enantiomer or single diastereomer), mixtures of stereoisomers (e.g. any mixture of enantiomers or diastereomers) or racemic mixtures thereof. Individual optically-active forms of the compounds can be prepared for example, by synthesis from optically-active starting materials, by chiral synthesis, by enzymatic resolution, by biotransformation, or by chromatographic separation. It is to be understood that the present invention encompasses any racemic, optically-active, stereoisomeric form, or mixtures of various proportions thereof, which form possesses properties useful in the inhibition of DGAT-1 activity. Where the stereochemistry of the chiral centers present in the chemical structures illustrated herein is not specified, the chemical structure is intended to encompass compounds containing either stereoisomer of each chiral center present in the compound, and mixtures thereof.

Geometric isomers can exist in the present compounds. The invention, contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

Within the present invention it is to be understood that compounds disclosed herein can exhibit the phenomenon of tautomerism and that the formulae drawings within this specification can represent only one of the possible tautomeric forms. It is to be understood that the invention encompasses any tautomeric form and is not to be limited merely to any one tautomeric form utilized within the naming of the compounds or formulae drawings.

Synthetic Methods

This invention is intended to encompass compounds of the invention when prepared by synthetic processes or by metabolic processes. Preparation of the compounds of the invention by metabolic processes include those occurring in the human or animal body (in vivo) or processes occurring in vitro.

The synthesis of compounds of formula (I) wherein the groups $R^1$ and $R^2$ have the meanings as set forth in the summary section unless otherwise noted, is exemplified in Schemes 1-8.

As used in the descriptions of the schemes and the examples, certain abbreviations are intended to have the following meanings: DMSO for dimethylsulfoxide, RP-HPLC for preparative reverse phase high pressure liquid chromatography, Boc is tert-butoxycarbonyl, and OTs is p-tolylsulfonate.

Compounds of the invention were named by ACD/ChemSketch version 5.06 (developed by Advanced Chemistry Development, Inc., Toronto, ON, Canada) or were given names consistent with ACD nomenclature.

Compounds of general formula (I) can be prepared using general procedures as outlined in Scheme 1.

Scheme 1

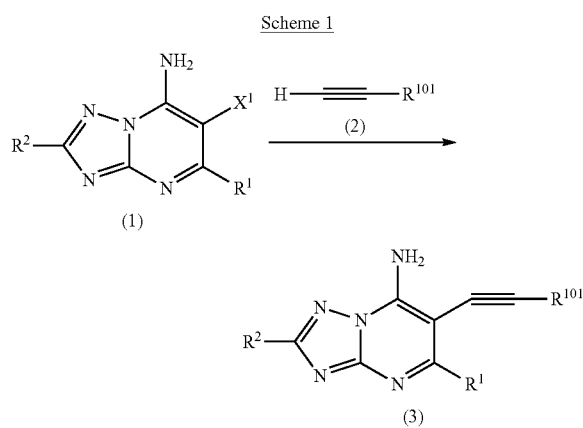

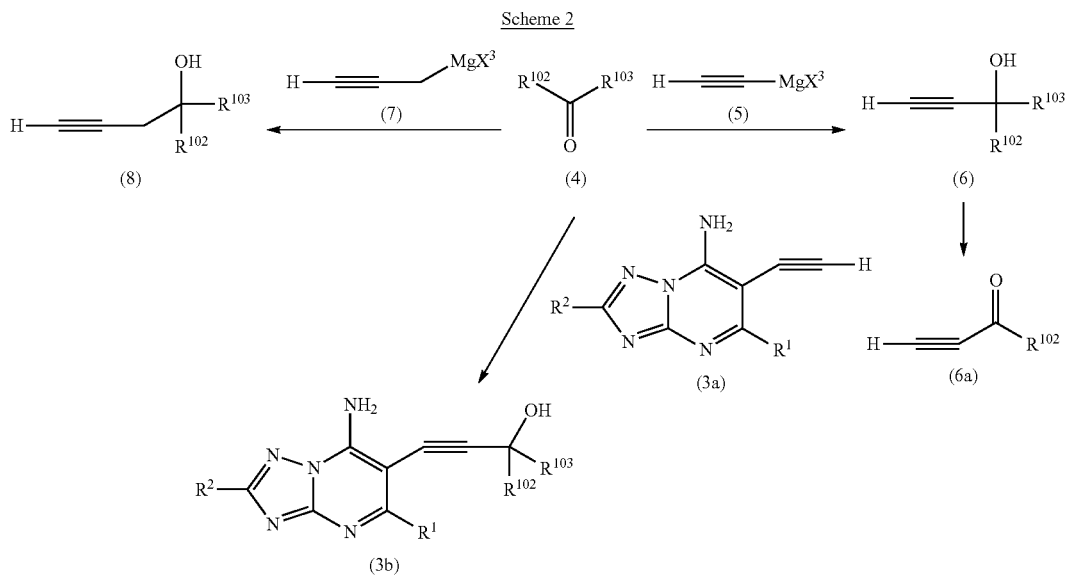

Aromatic halides of formula (1) wherein $X^1$ is halogen can be coupled to alkynes of formula (2) wherein $R^{101}$ is $R^3$ or trialkylsilyl such as trimethylsilyl, using Sonogashira coupling conditions. For example, the reaction is generally conducted in the presence of a base, a palladium catalyst and a copper (I) salt. An example of the copper (I) salt that can be employed to mediate the coupling reaction is copper (I) iodide. Examples of the palladium catalysts include, but are not limited to, bis(triphenylphosphine)palladium(II) dichloride and tetrakis(triphenylphosphine)palladium(0). Examples of the bases include organic base such as trialkylamine (for example, diisopropylethyamine or triethylamine), or inorganic bases such as sodium or potassium salt of $C_{1-6}$ alkoxide (for example, sodium methoxide), cesium fluoride, sodium, potassium or cesium carbonate, and the like. The reaction is generally performed at temperature ranging from about room temperature to about 150° C., preferably at about 50° C. to about 150° C., and more preferably at about 90° C. to about 120° C., in a solvent such as acetonitrile, aromatic hydrocarbon such as toluene, xylene, or benzene, water, N,N-dimethylformamide, dimethylsulfoxide, dioxane, or mixtures thereof.

Compounds of formula (3) wherein $R^{101}$ is trialkylsilyl can be converted to compounds of formula (3) wherein $R^{101}$ is hydrogen by, for example, treatment with a base such as potassium carbonate, in a solvent such as a mixture of tetrahydrofuran and methanol.

Compounds of formula (3) wherein $R^{101}$ is hydrogen can be coupled with halides of formula $R^3$—$X^2$, wherein $X^2$ is halide and $R^3$ is aryl or heteroaryl, using Sonogashira coupling conditions as described hereinabove.

Intermediates of formula (2) can be purchased prepared using reaction conditions analogous to those known in the literatures. For example, alkynes of formula (6), (6a) or (8) wherein $R^{102}$ and $R^{103}$ are each independently aryl, alkyl, haloalkyl, hydrogen, aryl, heteroaryl, cycloalkyl, heterocycle, arylalkyl, heteroarylalkyl, cycloalkylalkyl, or heterocyclealkyl, or $R^{102}$ and $R^{103}$, together with the carbon to which they are attached, form a cycloalkyl or heterocycle ring, can be prepared using general procedures as illustrated in Scheme 2.

Grignard reagents of formula (5) or (7) wherein $X^3$ is halogen can be treated with ketones or aldehydes of formula (4) in a solvent such as, but not limited to, tetrahydrofuran and diethylether, to provide alcohols of formula (6). Grignard reagents of formula (7) can be prepared from, for example, the reaction of propargyl halides of formula $(H)CCCH_2X^3$ with magnesium in the presence of mercury(II) halides, in a solvent such as diethyl ether. Compounds of formula (6a) wherein $R^{102}$ is hydrogen, aryl, alkyl, haloalkyl, aryl, heteroaryl, cycloalkyl, heterocycle, arylalkyl, heteroarylalkyl, cycloalkylalkyl, or heterocyclealkyl can be prepared by oxidizing (6) wherein $R^{103}$ is hydrogen with an oxidizing agent such as, but not limited to, Dess Martin reagent.

In the presence of a base such as n-butyllithium, compounds of formula (3a) can be deprotonated and the resulting anion, when treated with ketones or aldehydes of formula (4) in a solvent such as, but not limited to, tetrahydrofuran and diethylether, provides compounds of formula (3b) wherein $R^{102}$ and $R^{103}$ are as defined in Scheme 1.

Scheme 3

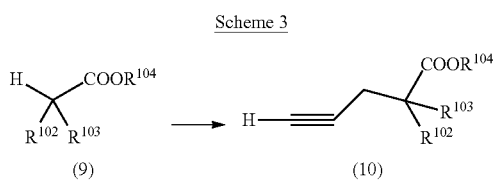

Alkynes of formula (10) wherein $R^{102}$ and $R^{103}$ are as defined hereinabove can be prepared from the compounds of formula (9) wherein $R^{104}$ is an acid protecting group such as, but not limited to, $C_{1-6}$ alkyl, trialkylsilylalkyl, benzyl (substituted or unsubstituted), etc. Such protecting acids, can be prepared from the corresponding acids using procedures analogous to, those known in the art. For example, 2-trimethylsilyl)ethyl, can be incorporated into the corresponding acid by reacting the acid with 2-(trimethylsilyl)ethanol in the presence of a coupling reagent such as 1-ethyl-3-[3-(dimethylamino)propyl]-carbodiimide hydrochloride. In the presence of a strong base such as sodium hydride or lithium diisopropylamide; in a solvent such as, but not limited to, tetrahydrofuran or N,N-dimethylformamide, at a temperature from about −78° C. to about room temperature, the protected acids can be de-protonated and the resulting anions can be treated in situ with propargyl halides of formula $(H)CCCH_2X^3$ wherein $X^3$ is halogen, at about room temperature, to provide compounds of formula (10).

Scheme 4

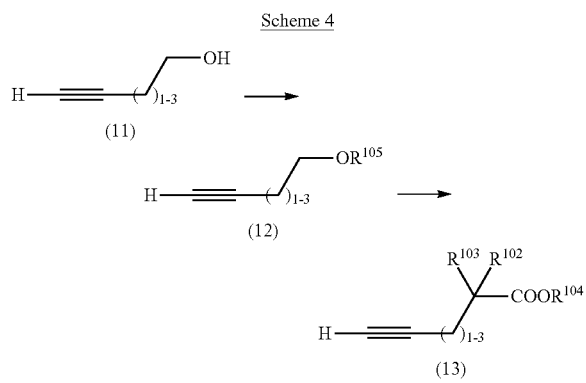

Protected acids of formula (13) can be prepared from the corresponding alcohols of formula (11) by (a) treatment with a halide such as trifluoromethane sulfonyl halide, benzenesulfonyl halide or toluenesulfonyl halide, in the presence of an organic base such as pyridine, or an inorganic base such as sodium carbonate, to provide compounds of formula (12) wherein $R^{105}$ is trifluoromethane sulfonyl, benzenesulfonyl or toluenesulfonyl; and (b) reacting the compounds of formula (12) with the anions formed in situ from (9) as described in Scheme 3.

Scheme 5

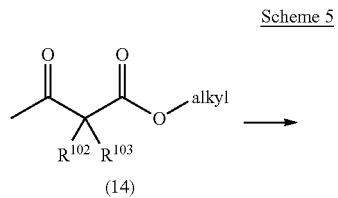

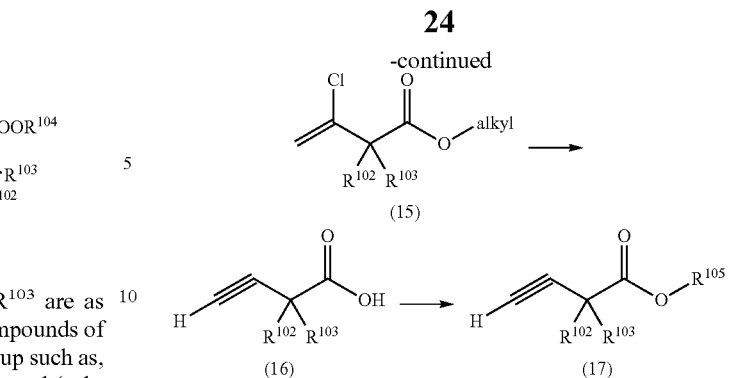

Protected acids of formula (17) can be prepared from β-keto esters of formula (14) as shown in Scheme 5.

Treatment of (14) with phosphorous pentachloride affordschlorides of formula (15). Hydrolysis of the ester to the corresponding acid, followed by treatment with $NaNH_2$ in dimethylsulfoxide, provides acids of formula (16) which can be protected to yield (17) using methodologies anagolous to those known in the art.

Scheme 6

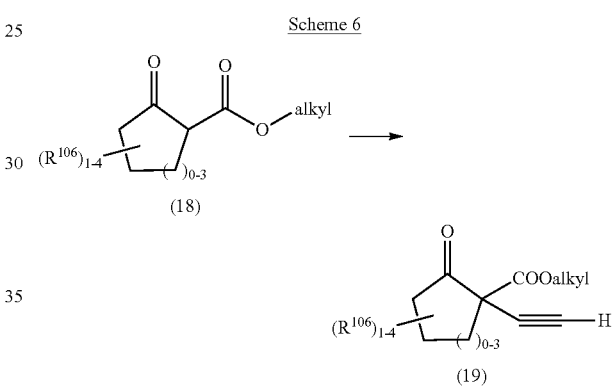

Alkynes of formula (19) wherein $R^{106}$ is alkyl, haloalkyl, or halogen, can be prepared from corresponding compounds of formula (18) using procedures anagolous to those described in J. Chem. Soc., Chem. Commun., 1990, 2, p. 118-119, and Tetrahedron Lett., 1986, 27, p. 5024-5028.

Scheme 7

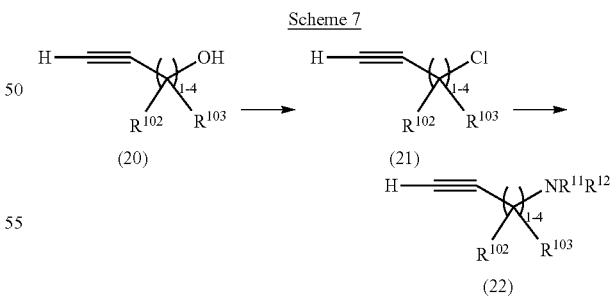

Alkynes of formula (22) can be prepared from the corresponding alcohols of formula (20) as illustrated in Scheme 5.

Conversion of alcohols of formula (20) to chlorides of formula (21) can be accomplished using procedures analogous to those described in JAGS; 1957, 79, p. 2142-2144. Displacement of the chlorides with $NaNH_2$ or amines of formula $HNR^{11}R^{12}$ wherein $R^{11}$ and $R^{12}$ are not both hydrogen, provides amines of formula (22).

Scheme 8

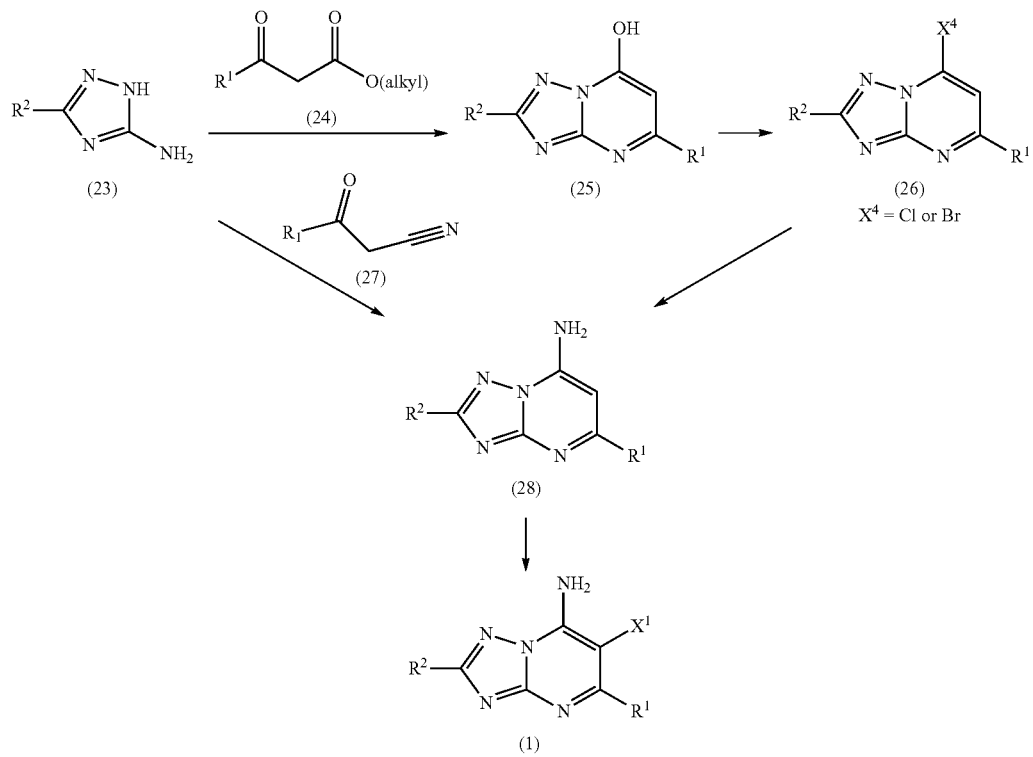

Condensation of appropriate β keto esters, of formula (24) with aminotraizoles of formula (23) under temperature ranging from about room temperature to about the boiling point of the solvent employed, provides hydroxypyrimidine derivatives of formula (25). Examples of the inert solvent used in this reaction include acetic acid, a lower alcohol solvent such as ethanol, methanol, isopropyl alcohol, and the like; an aromatic hydrocarbon solvent such as toluene, benzene, chlorobenzene, xylene, etc.; and an ethereal solvent such as tetrahydrofuran, 1,4-dioxane, etc.

The halopyrimidine derivatives of formula (26) can be obtained from the reaction of (25) with an appropriate halogenating agent, preferably with a brominating (for example, phosphorous oxybromide) or a chlorinating agent (for example, phosphorous oxychloride), neat or in the presence of a solvent, and in the presence of an appropriate acid scavenger. Examples of the acid scavenger are organic bases such as triethylamine, diisopropylethyl amine, dimethylaminopyridine, pyridine, etc.; and inorganic bases such as sodium hydroxide, sodium or potassium bicarbonate, etc. The reaction is suitably carried out at a temperature from about 25° C. to about 15° C., preferably at about 80° C. to about 120° C. Examples of solvent include, but are not limited to, aromatic hydrocarbon solvents such as benzene, xylene, chlorobenzene, toluene etc.

The transformation of compounds of formula (26) to compounds of formula (28) can be accomplished by reaction of the former, with a solution of ammonia in a solvent such as but not limited to methanol. The reaction is typically conducted at about 60° C. to about 100° C.

Alternatively, aminotriazoles of formula (23) can be treated with nitriles of formula (27) under temperature conditions ranging from room temperature to the boiling point of the solvent employed, to provide compounds of formula (28). Examples of the inert solvent used in this reaction include acetic acid, a lower alcohol solvent such as ethanol, methanol, isopropyl alcohol, and the like; an aromatic hydrocarbon solvent such as toluene, benzene, chlorobenzene, xylene, etc.; and an ethereal solvent such as tetrahydrofuran, 1,4-dioxane, etc.

Iodination of compounds of formula (28) provides compounds of formula (1) wherein $X^1$ is iodine can be accomplished by reacting (28) with an iodinating agent. Examples of the iodinating agent are for example, IC1 (commercially available or produced in situ from the reaction of sodium iodide and chloramines-T hydrate in the presence of acetic acid), N-iodosuccinimide, iodine, benzyltrimethylammonium dichloroiodide, and the like.

Aminotriazoles of formula (23) are either commercially available or can be prepared from reaction conditions analogous to those known in the art. For example, (23) can be obtained from the reaction of carboxylic acids of formula $R^2COOH$, or its esters, or acid chlorides thereof, with aminoguanidine hydrochloride or aminoguarnidine bicarbonate.

It will be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimal reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Synthetic Examples section. Reactions can be worked up in the conventional manner, e.g. by eliminating the solvent froth the residue and further purified according to methodologies generally known in the art such as, but not limited to, crystallization, distillation, extraction; trituration and chromatography. Unless otherwise described the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction, conditions, and deprotection at suitable point in the reaction sequence of the method are included in the scope of the invention. Suitable protecting groups and the methods for protecting and deprotecting different substituents using such suitable protecting groups are well known to those skilled in the art; examples of which can be found in T. Greene and, P. Wuts, Protecting Groups in Chemical Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

Biological Data

Inhibition of DGAT-1

The identification of the compounds of the invention as DGAT-1 inhibitors was readily achieved using a high throughput screening FlashPlate assay. In this assay, recombinant human DGAT-1 containing an N-terminal $His_6$-epitope tag was produced in the baculovirus expression system. Insect cells (e.g., Sf9 or High Five) were infected for 24 to 72 hours and collected by centrifugation. Cell pellets were resuspended in homogenization buffer [250 mM sucrose, 10 mM Tris-HCl (pH 7.4), 1 mM EDTA] and lysed using a homogenization apparatus, such as a Microfluidizer (single pass, 4° C.). Cell debris was removed by centrifugation at 10,000×g for 30 min, and microsomal membranes were collected by ultracentrifugation at 100,000×g for 30 min.

DGAT-1 activity was determined as follows: Assay buffer [20 mM HEPES (pH 7.5), 2 mM $MgCl_2$, 0.04% BSA] containing 50 µM of enzyme substrate (didecanoyl glycerol) and 7.5 µM radiolabeled acyl-CoA substrate.[$1-^{14}C$]decanoyl-CoA) was added to each well of a phospholipid. FlashPlate (PerkinElmer Life Sciences). A small aliquot of membrane (1 µg/well) was added to start the reaction, which was allowed to proceed for 60 min. The reaction was terminated upon the addition of an equal volume (100 µL) of isopropanol. The plates were sealed, incubated overnight and counted the next morning on a TopCount Scintillation Plate Reader (PerkinElmer Life Science). DGAT-1 catalyzes the transfer of the radiolabel-led decanoyl group onto the sn-3 position of didecanoyl glycerol. The resultant radiolabeled tridecanoyl glycerol (tricaprin) preferentially binds to the hydrophobic coating on the phospholipid FlashPlate. The proximity of the radiolabeled product to the solid scintillant incorporated into the bottom of the FlashPlate induced fluor release from the scintillant, which was measured in the TopCount Plate Reader. Various concentrations (e.g. 0.0001 µM, 0.001 µM, 0.01 µM, 0.1 µM, 1.0 µM, 10.0 µM) of the representative compounds of the invention were added to individual wells prier to the addition of membranes. The potencies of DGAT-1 inhibition for the compounds of the present invention were determined by calculating the $IC_{50}$ values defined as the inhibitor concentration from the sigmoidal dose response curve at which the enzyme activity was inhibited 50%. Compounds of the present invention were effective in inhibiting DGAT-1 activity and thus are useful as therapeutic agents for treating conditions and diseases, that are associated with DGAT-1 activity.

TABLE 1

DGAT-1 Inhibition of compounds of the present invention ($IC_{50}$ µM)

| | | | | | |
|---|---|---|---|---|---|
| 0.00754 | 0.00772 | 0.01077 | 0.01104 | 0.01118 | 0.0133 |
| 0.0133 | 0.0143 | 0.0146 | 0.01535 | 0.01771 | 0.01855 |
| 0.01912 | 0.02689 | 0.028 | 0.03192 | 0.03236 | 0.033 |
| 0.03301 | 0.0333 | 0.03558 | 0.039 | 0.04538 | 0.04873 |
| 0.04973 | 0.05443 | 0.0602 | 0.061 | 0.06187 | 0.06317 |
| 0.06973 | 0.07075 | 0.07371 | 0.09735 | 0.1046 | 0.10806 |
| 0.11939 | 0.14815 | 0.1534 | 0.15414 | 0.20577 | 0.2751 |
| 0.321 | 0.32826 | 0.329 | 0.36042 | 0.40512 | 0.41522 |
| 0.44694 | 0.4603 | 0.483 | 0.48431 | 0.50815 | 0.522 |
| 0.5707 | 0.58654 | 0.61032 | 0.71215 | 0.77617 | 0.81507 |

Evaluation of Compound Efficacy on the Reduction of Chylomicron Excursion in DIO or CD1 Mice The purpose of this protocol was to determine the effect of acute administration of a compound on the chylomicron excursion induced by a corn oil bolus in either lean mice (CD1 mice, Jackson Laboratories) or mice made obese by spontaneous ad libitum consumption of a high-fat diet (Buhman, K. K. et al., *J Biol Chem*. 2002, 277, 25474-25479). Diet-induced obesity (DIO) in rodents mimics key aspects of human obesity and metabolic syndrome. DIO mice used in this study have been shown to be hyperinsulinemic and insulin resistant, hyperleptinemic and leptin resistant, and have marked visceral obesity (for review on DIO mice see Collins et al.; Physiol. Behav. 81:243-248, 2004).

Representative compounds of the invention were typically dosed at 0.03 mg/kg, 0.3 mg/kg, 3 mg/kg, or 10 mg/kg p.o as a formulation in 1% Tween 80 in water one hour prior to the administration of corn oil bolus. One hour after the bolus was administered, plasma samples were taken and analyzed for triglycerides. The compounds were considered to be active if drug treatment resulted in >30% reduction in plasma triglycerides in drug, treated animals (measured one hour after the administration of corn oil bolus) relative to vehicle-treated control animals. In this model, representative compounds produced significant reductions in plasma triglycerides, relative to vehicle-treated control animals.

Compounds of the present invention and the pharmaceutically acceptable salts are useful as therapeutic agents. Accordingly, an embodiment of this invention includes a method of treating the various conditions in a subject in need thereof (including mammals) which includes administering to said subject an amount of the compound of formula (I), or a pharmaceutically acceptable salt, prodrug, or salt of a prodrug thereof, that is effective in treating the target condition, or a pharmaceutical composition including the same.

Another aspect of the present invention provides a method of treating, delay or prevention of various conditions in a patient (such as mammal, preferably human) that are mediated by DGAT-1, which includes administering to said patient a compound of formula (I), or a pharmaceutically acceptable salt, prodrug, salt of a prodrug thereof, or a pharmaceutical composition including the same.

Another aspect of the present invention provides methods for the prevention, delay or treatment of obesity and inducing weight loss in an individual, which includes administering to said individual a compound of the invention, or its pharmaceutically acceptable salt, prodrug, salt of a prodrug thereof, or a pharmaceutical composition including the same. Yet another aspect of the invention provides a method for preventing weight gain in an individual by administering at least one compound of the invention, or its pharmaceutically acceptable salt, prodrug, salt of a prodrug, or a combination thereof, in an amount that is sufficient to prevent weight gain.

The present invention also relates to the use of the compounds of this invention for the treatment of obesity-related diseases including associated dyslipidemia and other obesity- and overweight-related complications, such as, for example, cholesterol gallstones, gallbladder disease, gout, cancer (e.g., colon, rectum, prostate, breast, ovary, endometrium, cervix, gallbladder, and bile duct), menstrual abnormalities, infertility, polycystic ovaries, osteoarthritis, and sleep apnea, as well as for a number of other pharmaceutical uses associated therewith, such as the regulation of appetite and food intake, dyslipidemia, hypertriglyceridemia, metabolic syndrome or Syndrome X, type 2 diabetes (non-insulin-dependent diabetes), atherosclerotic diseases such as heart failure, hyperlipidemia, hypercholesteremia, low HDL levels, hypertension, cardiovascular disease (including atherosclerosis, coronary heart disease, coronary artery disease, and hypertension), cerebrovascular disease such as stroke, and peripheral vessel disease. The compounds of this invention can also be useful for treating physiological disorders related to, for example, regulation of insulin sensitivity, inflammatory response, liver steatosis, elevated liver triacylglycerides, non-alcoholic fatty liver disease, non-alcoholic steatohepatitis, plasma triacylglycerides, HDL, LDL and cholesterol levels and the like. Metabolic syndrome is characterized by a group of metabolic risk factors in one person. Such factors include, but are not limited to, abdominal obesity, atherogenic dyslipidemia (blood fat disorders such as high triglycerides, low HDL cholesterol and high LDL cholesterol), elevated blood pressure, insulin resistance (or glucose intolerance), prothrombotic state (e.g. high fibrinogen or plasminogen activator inhibitor-1 in the blood), and proinflammatory state (e.g. elevated C-reactive protein in the blood). In one embodiment, the present invention provides methods of treating the above listed disorders wherein said methods include the step of to a subject in need thereof one or more of the compound of the invention, or pharmaceutically acceptable salt thereof or a pharmaceutical composition including the same. The compounds of this invention, or pharmaceutical acceptable salts thereof, or pharmaceutical compositions including the same, are also useful in lowering plasma triglycerides level. Thus, in one embodiment, the present invention provides a method for lowering plasma triglycerides in a subject (including mammal) in need thereof, wherein said method includes the step of administering to the subject in need thereof one or more of the compound of invention, or pharmaceutically acceptable salt thereof, or a pharmaceutical composition including the same.

The term "treatment" or "treating" includes any process, action, application, therapy, or the like, wherein a subject, including human, is provided medical aid with the object of improving the subject s condition, directly or indirectly, or slowing the progression of a condition or disorder in the subject.

Compounds of the invention, or pharmaceutically acceptable salts, prodrugs, salts of prodrugs, or combination thereof, can be administered alone or in combination (i.e. co-administered) with one or more additional pharmaceutical agents. Combination therapy includes administration of a single pharmaceutical dosage formulation containing one or more of the compounds of invention, or pharmaceutically acceptable salts, prodrug, salts of prodrugs thereof, and one or more additional pharmaceutical agents, as well as administration of the compounds of invention, or pharmaceutically acceptable salts, prodrug, salts of prodrugs thereof, and each additional pharmaceutical agent, in its own separate pharmaceutical dosage formulation. For example, a compound of formula (I), or a pharmaceutically acceptable salts, prodrugs, salts of prodrugs thereof, and one or more additional pharmaceutical agents, can be administered to the patient together, in a single oral dosage composition having a fixed ratio of each active ingredient, such as a tablet or capsule; or each agent can be administered in separate oral dosage formulations.

Where separate dosage formulations are used, compounds of the invention (or pharmaceutical salts, prodrugs, or salts of prodrugs thereof) and one or more additional pharmaceutical agents can be administered at essentially the same time (e.g., concurrently) or at separately staggered times (e.g., sequentially).

For example, the compounds of the invention (or pharmaceutical salts, prodrugs, or salts of prodrugs thereof) can be used in combination with one of more of the following pharmaceutical agents, including, but not limited to, anti-obesity drugs including $\beta$-3 agonists such as CL-316,243; CB-1 antagonists and/or inverse agonsists (for example, rimonabant); neuropeptide Y5 inhibitors; appetite suppressants, such as, for example, sibutramine (Meridia); MCHr1 antagonists and lipase inhibitors, such as, for example, orlistat Xenical), and a drug compound that modulates digestion and/or metabolism such as drugs that modulate thermogenesis, lipolysis, gut motility, fat absorption, and satiety.

In addition, compounds of the invention (or pharmaceutical salts, prodrugs, or salts of prodrugs thereof) can be administered in combination with, one or more of the following pharmaceutical agents including PPAR ligands (agonists, antagonists), insulin secretagogues (for example, sulfonylurea drugs and non-sulfonylurea secretagogues), $\alpha$-glucosidase inhibitors, insulin sensitizers, hepatic glucose output lowering compounds, and insulin and insulin derivatives. Such agents can be administered prior to, concurrently with, or following administration of the compounds of the invention. Insulin and insulin derivatives include both long and short acting forms and formulations of insulin. PPAR ligands can include agonists and/or antagonists of any of the PPAR receptors or combinations thereof. For example, PPAR ligands can include ligands of PPAR-$\alpha$, PPAR-$\gamma$, PPAR-$\delta$ or any combination of two or three of the receptors of PPAR. PPAR ligands include, for example, rosiglitazone, troglitazone, and pioglitazone. Sulfonylurea drugs include, for example, glyburide, glimepiride, chlorpropamide, tolbutamide, and glipizide. α-glucosidase inhibitors include acarbose; miglitol, and voglibose. Insulin sensitizers include PPAR-γ agonists such as the glitazones (e.g., troglitazone, pioglitazone, englitazone, MCC-555, rosiglitazone, and the like) and other thiazolidinedione and non-thiazolidinedione compounds; biguanides such as metformin and phenformin; protein tyrosine phosphatase-1B (PP-1B) inhibitors; dipeptidyl peptidase IV (DPP-IV) inhibitors (for example, sitagliptin), and 11beta-HSD inhibitors. Hepatic glucose output lowering compounds include glucagon anatgonists and metformin, such as Glucophage and Glucophage XR. Insulin secretagogues include sulfonylurea and non-sulfonylurea drugs: GLP-1, GIP, PACAP, secretin, and derivatives thereof; nateglinide, meglitinide, repaglinide, glibenclamide; glimepiride, chlorpropamide, glipizide. GLP-1 includes derivatives of GLP-1 with longer half-lives than native GLP-1, such as, for example, fatty-acid derivatized GLP-1 and exendin.

Compounds of the invention (or pharmaceutical salts, prodrugs, or salts of prodrugs thereof) can also be used in methods of the invention in combination with one or more pharmaceutical agents including, but are not limited to, HMG-CoA reductase inhibitors, nicotinic acid (for example, Niaspan), fatty acid lowering compounds (e.g., acipimox); lipid lowering drugs (e.g., stanol esters, sterol glycosides such as tiqueside, and azetidinones such as ezetimibe), ACAT inhibitors (such as avasimibe), bile acid sequestrants, bile acid reuptake inhibitors, microsomal triacylglycerides transport inhibitors, and fibric acid derivatives. HMG-CoA reductase inhibitors include, for example, statin such as lovastatin, simvastatin, pravastatin, fluvastatin, atorvastatin, rivastatin, itavastatin, cerivastatin, and ZD-4522. Fibric acid derivatives include, for example, clofibrate, fenofibrate, bezafibrate, ciprofibrate, beclofibrate, etofibrate, and gemfibrozil. Sequestrants include, for example, cholestyramine, colestipol, and dialkylaminoalkyl derivatives of a cross-linked dextran.

Compounds of the invention (or pharmaceutical salts, prodrugs, or salts of prodrugs thereof) can also be used in combination with anti-hypertensive drugs, such as, for example, β-blockers and ACE inhibitors. Examples of additional antihypertensive agents for use in combination with the compounds of the present invention include calcium channel blockers (L-type and T-type; e.g., diltiazem, verapamil, nifedipine, amlodipine and mybefradil, diuretics (e.g., chlorothiazide; hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine; bumetanide, triamtrenene, amiloride, spironolactone), renin inhibitors, ACE inhibitors (e.g., captopril, zofenopril; fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, neutral endopeptidase (NEP) inhibitors, vasopepsidase inhibitors (dual NEP-ACE inhibitors) (e.g., omapatrilat and gemopatrilat), and nitrates.

The compounds of this invention can also be co-administered with an incretin mimetic such as, but not limited to, exenatide.

The compounds of this invention (or pharmaceutical salts, prodrugs, or salts of prodrugs thereof) can be utilized to achieve the desired pharmacological effect by administration to a subject in need thereof in an appropriately formulated pharmaceutical composition. A subject, for example, can be a mammal, including human, in need of treatment for a particular condition or disease. Therefore the present invention includes pharmaceutical compositions which are included of a therapeutically effective amount of a compound (or pharmaceutical salts, prodrugs, or salts of prodrugs thereof) identified by the methods described herein, in combination with a pharmaceutically acceptable carrier. The compounds identified by the methods described herein can be administered with a pharmaceutically acceptable carrier using any effective conventional dosage unit forms, for example, immediate and timed release preparations, orally, parenterally, topically, or the like.

The pharmaceutical compositions can be formulated for oral administration in solid or liquid form, for parenteral injection or for rectal administration.

The term "pharmaceutically acceptable carrier" as used herein, means a non-toxic, solid, semi-solid or liquid filler, diluent, encapsulating material, or formulation auxiliary of any type. Examples of therapeutically suitable excipients include sugars; cellulose and derivatives thereof; oils; glycols; solutions; buffering, coloring, releasing, coating, sweetening, flavoring, and perfuming agents; and the like. These therapeutic compositions can be administered parenterally, intracisternally, orally, rectally, intravenously, or intraperitoneally.

Liquid dosage forms for oral administration of the present compounds include formulations of the same as emulsions, microemulsions, solutions, suspensions, syrups, and elixirs. In addition to the compounds, the liquid dosage fonts can contain diluents and/or solubilizing or emulsifying agents. Besides inert diluents, the oral compositions can include wetting, emulsifying, sweetening, flavoring, and perfuming agents.

Injectable preparations of the present compounds include sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents that dissolve or disperse in the injectable media.

Inhibition of DGAT-1 by the compounds of the present invention can be delayed by using a liquid suspension of crystalline or amorphous material with poor water solubility. The rate of absorption of the compounds depends upon their rate of dissolution which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions that are compatible with body tissues.

Solid dosage fonts for oral administration of the present compounds include capsules, tablets, pills, powders, and granules. In such forms, the compound is mixed with at least one inert, therapeutically suitable excipient such as a carrier, filler, extender, disintegrating agent, solution retarding agent, wetting agent, absorbent, or lubricant. With capsules, tablets, and pills, the excipient can also contain buffering agents. Suppositories for rectal administration can be prepared by mixing the compounds with a suitable non-irritating excipient that is solid at ordinary temperature but fluid in the rectum.

The present compounds can be micro-encapsulated with one or more of the excipients discussed previously. The solid dosage forms of tablets, dragees, capsules, pills, and granules can be prepared with coatings and shells such as enteric and release-controlling. In these forms, the compounds can be mixed with at least one inert diluent and can optionally include tableting lubricants and aids. Capsules can also optionally contain opacifying agents that delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of disclosed herein which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

Pharmaceutically acceptable salts are well-known in the art. The salts can be prepared during the final isolation and purification of the compounds or Separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, malate, maleate, methanesulfonate, naphthylenesulfonate, nicotinate, oxalate, pamoate, pectinate, persulfate, 3-phenylpropionate, picrate, oxalate, pivalate, propionate, succinate, tartrate, dichloroacetic, trifluoroacetic, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like.

Basic addition salts can be prepared during the final isolation and purification of the present compounds by reaction of a carboxyl group with, a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_{1-6}$ alkyl esters and $C_{5-7}$ cycloalkyl esters, although $C_{1-4}$ alkyl esters are preferred. Esters of the compounds of the invention can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The "term pharmaceutically acceptable amide," as, used, herein, refers to non-toxic amides of the invention derived from ammonia, primary $C_{1-6}$ alkyl amines and secondary $C_{1-6}$ dialkyl amines. In the case of secondary amines, the amine can also be in the form of a 5- or 6-membered heterocycle containing one nitrogen atom. Amides derived from ammonia, $C_{1-3}$ alkyl primary amides and $C_{1-2}$ dialkyl secondary amides are preferred. Amides of the compounds of the invention, can be prepared according to conventional methods. Pharmaceutically acceptable amides can be prepared from compounds containing primary or secondary amine groups by reaction of the compound that contains they amino group with an alkyl anhydride, aryl anhydride, acyl halide, or amyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug" as, used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of the invention, for example, by hydrolysis in blood. A thorough discussion is provided in T. Higuchi and V. Stella, Pro-drugs as Novel. Delivery Systems, V. 14 of the A.C.S. Symposium Series, and in Edward B. Roche, ed., Bioreversible Carriers in Drug Design, American Pharmaceutical Association and Pergamon Press (1987).

Disorders that can be treated or prevented in a patient by administering to the patient, a therapeutically effective amount of compound (or pharmaceutical salts, prodrugs, or salts of prodrugs thereof) of the present invention in such an amount and for such time as is necessary to achieve the desired result. The term "therapeutically effective amount," refers to a sufficient amount of a compound of the invention to effectively ameliorate disorders by inhibiting DGAT-1 at a reasonable benefit/risk ratio applicable to any medical treatment. The specific therapeutically effective dose level for any particular patient can depend upon a variety of factors including the disorder being treated and the severity of the disorder; the activity of the compound employed; the specific Composition employed; the age, body weight, general health, sex, and diet of the patient; the time of administration, route of administration; rate of excretion; the duration of the treatment; and drugs used in combination or coincidental therapy.

The total daily dose of the compounds of the present invention necessary to inhibit the action of DGAT-1 in single or divided doses can be in amounts, for example, from about 0.01 to 50 mg/kg body weight. In a more preferred range, compounds of the present invention inhibit the action of DGAT-1 in a single or divided, doses from about 0.05 to 25 mg/kg body weight. Single dose compositions can contain such amounts or submultiple doses thereof of the compounds of the present invention to make up the daily dose. In general, treatment regimens include administration to a patient in need of such treatment from about 1 mg to about 1000 mg of the compounds per day in single or multiple doses.

The compounds identified by the methods described herein can be administered as the sole pharmaceutical agent or in combination with one or more other pharmaceutical agents where the combination causes no unacceptable adverse effects. For example, the compounds of this invention can be combined with anti-obesity, or with known antidiabetic or other indication agents, and the like. Thus, the present, invention also includes pharmaceutical compositions which are made of a therapeutically effective amount of a compound identified by the methods described herein, or a pharmaceutically acceptable salt thereof, a pharmaceutically acceptable carrier, and one of more pharmaceutical agents as disclosed hereinabove.

EXAMPLES

Example 1

6-[(4-aminophenyl)ethynyl]-5-methyl[1,2,4]triazolo[1,5-a]pyrimidin-7-amine

The title compound was prepared according to the procedures described in Example 4B, substituting the commercially available 4-ethynylaniline for 1-ethynylcyclopentanol used in Example 4B. $^1$H NMR (30.0 MHz, DMSO-$d_6$) δ 8.56 (s, 1H), 8.44 (brs, 2H), 7.40 (d, J=8.8 Hz, 2H), 6.67 (d, J=8.8 Hz, 2H), 4.51 (brs, 2H), 2.59 (s, 3H). MS (ESI) m/z 265 (M+H)$^+$.

Example 2

6-(cyclohexylethynyl)-5-methyl[1,2,4]triazolo[1,5-a]pyrimidin-7-amine

The title compound was prepared according to the procedures described in Example 4B, substituting the commercially available ethynylcyclohexane for 1-ethynylcyclopentanol used in Example 4B. $^1$H NMR (300 MHz, DMSO-$d_6$) δ 8.47 (s, 1H), 8.26 (brs, 2H), 2.79-2.69 (m, 1H), 2.52 (s, 3H), 1.93-1.81 (m, 2H), 1.63-1.77 (m, 2H), 1.64-1.28 (m, 6H). MS (ESI) m/z 256 (M+H)$^+$.

Example 3

5-methyl-6-(4-phenylbut-1-ynyl)[1,2,4]triazolo[1,5-a]pyrimidin-7-amine

The title compound was prepared according to the procedures described in Example 4B, substituting the commercially available but-3-ynylbenzene for 1-ethynylcyclopentanol used in Example 4B. $^1$H NMR (300 MHz, DMSO-$d_6$) δ 8.40 (s, 1H), 8.12 (brs, 2H), 7.35-7.29 (m, 5H), 2.97-2.88 (m, 2H), 2.86-2.78 (m, 2H), 2.39 (s, 3H). MS (ESI) m/z 278 (M+H)$^+$.

Example 4

1-[(7-amino-5-methyl[1,2,4]triazolo[1,5-a]pyrimidin-6-yl)ethynyl]cyclopentanol

Example 4A 6-iodo-5-methyl-[1,2,4]triazolo[1,5-a]pyrimidin-7-amine

To a stirring mixture of 3.05 g (20.4 mmol) of 5-methyl[1,2,4]triazolo[1,5-a]pyrimidin-7-amine (prepared as described in Kano; Makisumi; Chem. Pharm. Bull.; 6; 1958; 583, 585) in 50 mL of acetic acid at room temperature was added NaI (3.2 g, 21.5 mmol). Chloramine-T trihydrate (6.0 g, 21.5 mmol) was then added portion wise. The resulting mixture was then stirred for 1 h at room temperature. Most of the organic solvent was removed on a rotavap. The mixture was taken tip in 40 mL of $CH_3CN$ and filtered. The solid collected was washed with diethyl ether and dried in vacuum oven to give the title compound as a light yellow solid (4.93 g, 88% yield).

Example 4B

1-[(7-amino-5-methyl[1,2,4]triazolo[1,5-a]pyrimidin-6-yl)ethynyl]cyclopentanol

Example 4A (350 mg, 1.27 mmol), bis(triphenylphosphine)palladium(II) dichloride (38 mg, 0.64 mmol), and CuI (21 mg, 0.13 mmol) were weighed into a pressure tube. $CH_3CN$ (10 mL) was added and the nitrogen was babbled through. 1-Ethynylcyclopentanol (180 mg, 1.91 mmol) and triethylamine (382 µL, 3.18 mmol) were then added sequentially. The pressure tube was then capped and heated at 110° C. for 20 min. The reaction mixture was then allowed to cool to robin temperature, and partitioned between ethyl acetate (15 mL) and brine (10 mL). The aqueous layer was extracted once with ethyl acetate (15 mL). The combined organic layer was over $MgSO_4$ and concentrated in vacuuo. The residue was purified by reverse phase HPLC (C-18 column, eluting with a 5-100% $CH_3CN$ gradient in 10 mM ammonium acetate$_{(aq.)}$) to give the title compound as a white solid (140 mg, 43% yield). $^1$H NMR (300 MHz, DMSO-$d_6$) δ 8.42 (s, 1H), 8.14 (brs, 2H), 5.36 (s, 1H), 2.51 (s, 3H), 2.05-1.84 (m, 4H), 1.83-1.62 (m, 4H). MS (ESI) m/z 258 (M+H)$^+$.

Example 5

1-[(7-amino-5-methyl[1,2,4]triazolo[1,5-a]pyrimidin-6-yl)ethynyl]cyclohexanol

The title compound was prepared according to the procedures described in Example 4B, substituting the commercially available 1-ethynyl-1-cyclohexanol for 1-ethynylcyclopentanol used in Example 4B. $^1$H NMR (300 MHz, DMSO-$d_6$) δ 8.41 (s, 1H), 8.19 (brs, 2H), 5.53 (s, 1H), 3.29 (s, 3H), 1.96-1.83 (m, 2H), 1.75-1.43 (m, 6H), 1.29-1.10 (m, 2H). MS (ESI) m/z 272 (M+H)$^+$.

Example 6

4-[(7-amino-5-methyl[1,2,4]triazolo[1,5-a]pyrimidin-6-yl)ethynyl]tetrahydro-2H-pyran-4-ol

Example 6A

4-Ethynyl-tetrahydro-pyran-4-ol

A solution of ethynylmagnesium chloride in tetrahydrofuran (0.5 M, 12 ML, 6.0 mmol) was added with cooling in an ice-water bath to a solution of tetrahydro-4H-pyran-4-one (0.496 g, 5.0 mmol) in diethyl ether (300 mL) dropwise over 15 min. The mixture was stirred at room temperature for 1 h. Aqueous saturated ammonium chloride solution (10.0 mL) was then added and mixture extracted with ether (2×20 mL). The ether layers were washed with saturated aqueous sodium chloride solution (20 mL), then combined, dried over $MgSO_4$, filtered and concentrated to give 4-ethynyl-tetrahydro-pyran-4-ol as a colorless oil that solidified on standing. (0.60 g, 96.2% yield).

Example 6B

4-[(7-amino-5-methyl[1,2,4]triazolo[1,5-a]pyrimidin-6-yl)ethynyl]tetrahydro-2H-pyran-4-ol The title compound was prepared according to the procedures described in Example 4B, substituting Example 6A for 1-ethynylcyclopentanol used in Example 4B. $^1$H NMR (300 MHz, DMSO-$d_6$) δ 8.52 (s, 1H), 8.31 (brs, 2H), 3.89-3.75 (m, 2H), 3.63-3.51 (m, 2H), 2.54 (s, 3H), 2.10-1.89 (m, 2H), 1.79-1.63 (m, 2H). MS (ESI) m/z 274 (M+H)$^+$.

Example 7

4-(7-amino-5-methyl[1,2,4]triazolo[1,5-a]pyrimidin-6-yl)-2-cyclopentylbut-3-yn-2-ol

Example 7A 2-cyclopentylbut-3-yn-2-ol

The title compound was prepared according to the procedures described in Example 6A, substituting 1-cyclopentylethanone for tetrahydro-4H-pyran-4-one used in Example 6A.

Example 7B 4-(1-amino-5-methyl[1,2,4]triazolo[1,5-a]pyrimidin-6-yl)-2-cyclopentylbut-3-yn-2-ol The title compound was prepared according to the procedures described in Example 4B, substituting Example 7A for 1-ethynylcyclopentanol used in Example 4B. $^1$H NMR (300 MHz, DMSO-$d_6$) δ 8.47 (s, 1H), 8.21 (brs, 2H), 2.50 (s, 3H), 2.17-2.03 (m, 1H), 1.81-1.43 (m, 8H), 1.46 (s, 3H). MS-(ESI) m/z 286 (M+H)$^+$.

Example 8

4-(7-amino-5-methyl[1,2,4]triazolo[1,5-a]pyrimidin-6-yl)-2-phenylbut-3-yn-2-ol

The title compound was prepared according to the procedures described in Example 4B, substituting the commercially available 2-phenyl-3-butyn-2-ol for 1-ethynylcyclopentanol used in Example 4B. $^1$H NMR (300 MHz, DMSO-$d_6$) δ 8.45 (s, 1H), 8.26 (brs, 2H), 7.67 (d, J=7.5 Hz, 2H), 7.39 (t, J=7.5 Hz, 2H), 7.28 (m, 1H), 6.16 (s, 1H), 2.54 (s, 3H), 1.75 (s, 3H). MS (ESI) m/z 294 (M+H)$^+$.

Example 9

4-(7-amino-5-methyl[1,2,4]triazolo[1,5-a]pyrimidin-6-yl)-1,1,1-trifluoro-2-phenylbut-3-yn-2-ol The title compound was prepared according to the procedures described in Example 4B, substituting the commercially available 1,1,1-trifluoro-2-phenyl-3-butyn-2-ol for 1-ethynylcyclopentanol used in Example 4B. $^1$H NMR (300 MHz, DMSO-$d_6$) δ 8.49 (s, 1H), 7.88 (s, 1H), 7.79-7.72 (m, 2H), 7.54-7.42 (m, 3H), 2.60 (s, 3H). MS (ESI) m/z 3.48 (M+H)$^+$.

Example 10

3-(7-amino-5-methyl[1,2,4]triazolo[1,5-a]pyrimidin-6-yl)-1,1-diphenylprop-2-yn-1-ol The title compound was prepared according to the procedures described in Example 4B, substituting the commercially available 1,1-diphenyl-2-propyn-1-ol for 1-ethynylcyclopentanol used in Example 4B. $^1$H NMR (300 MHz, DMSO-$d_6$) δ 8.48 (s, 1H), 8.28 (brs, 2H), 7.68-7.62 (m, 2H), 7.47-7.21 (m, 6H), 7.04-7.00 (m, 1H), 2.59 (s, 3H). MS (ESI) m/z 356 (M+H)$^+$.

Example 11

3-(7-amino-5-methyl[1,2,4]triazolo[1,5-a]pyrimidin-6-yl)-1-phenylprop-2-yn-1-ol

The title compound was prepared according to the procedures described in Example 4B, substituting the commercially available 1-phenyl-2-propyn-1-ol for 1-ethynylcyclopentanol used in Example 4B. $^1$H NMR (300 MHz, DMSO-$d_6$) δ 8.43 (s, 1H), 8.28 (brs, 2H), 7.60-7.55 (m, 2H), 7.44-7.36 (m, 3H), 7.34-7.27 (m, 1H), 6.08 (d, J=6.1 Hz, 1H), 5.68 (d, J=6.1 Hz, 1H), 2.50 (s, 3H). MS (ESI) m/z 280 (M+H)$^+$.

Example 12

6-(3-cyclohexylprop-1-ynyl)-5-methyl[1,2,4]triazolo[1,5-a]pyrimidin-7-amine

The title compound was prepared according to the procedures described in Example 4B, substituting the commercially available 3-cyclohexyl-1-propyne for 1-ethynylcyclopentanol used in Example 4B. $^1$H NMR (300 MHz, DMSO-$d_6$) δ 8.47 (s, 1H), 8.27 (brs, 2H), 2.43 (d, J=6.8 Hz, 2H), 1.89-1.50 (m, 5H), 1.34-0.99 (m, 6H). MS (ESI) m/z 270 (M+H)$^+$.

Example 13

3-(7-amino-5-methyl[1,2,4]triazolo[1,5-a]pyrimidin-6-yl)-1-cyclopropyl-1-phenylprop-2-yn-1-ol

Example 13A 1-cyclopropyl-1-phenylprop-2-yn-1-ol

The title compound was prepared according to the procedures described in Example 6A, substituting cyclopropyl (phenyl)methanone for tetrahydro-4H-pyran-4-one used in Example 6A.

Example 13B 3-(7 amino-5-methyl[1,2,4]triazolo[1,5-a]pyrimidin-6-yl)-1-cyclopropyl-1-phenylprop-2-yn-1-ol The title compound was prepared according to the procedures described in Example 4B, substituting Example 13A for 1-ethynylcyclopentanol used in Example 4B. $^1$H NMR (300 MHz, DMSO-$d_6$) δ 8.47 (s, 1H), 8.30 (brs, 2H), 7.74-7.68 (m, 2H), 7.44-7.37 (m, 3H), 7.35-7.27 (m, 1H), 6.69 (t, J=7.5 Hz, 1H), 2.61 (s, 3H), 3.63 (t, J=6.4 Hz, 2H), 2.71 (m, 2H). MS (ESI) m/z 320 (M+H)$^+$.

Example 14

6-[(4-methoxyphenyl)ethynyl]-5-methyl[1,2,4]triazolo[1,5-a]pyrimidin-7-amine

The title compound was prepared according to the procedures described in Example 4B, substituting 1-ethynyl-4-methoxybenzene for 1-ethynylcyclopentanol used in Example 4B. $^1$H NMR (300 MHz, DMSO-$d_6$) δ 8.52 (brs, 2H), 8.50 (s, 1H), 7.63 (d, J=-9.2 Hz, 2H), 6.99 (d, J=9.2 Hz, 2H), 3.80 (s, 3H), 2.61 (s, 3H). MS (ESI) m/z 280 (M+H)$^+$.

Example 15

3-(7-amino-5-methyl[1,2,4]triazolo[1,5-a]pyrimidin-6-yl)-1,1-bis(4-chlorophenyl)prop-2-yn-1-ol

Example 15A 1,1-bis(4-chlorophenyl)prop-2-yn-1-ol

The title compound was prepared according to the procedures described in Example 6A, substituting bis(4-chlorophenyl)methanone for tetrahydro-4H-pyran-4-one used in Example 6A.

Example 15B 3-(7-amino-5-methyl[1,2,4]triazolo[1,5-a]pyrimidin-6-yl)-1,1-bis(4-chlorophenyl)prop-2-yn-1-ol The title compound was prepared according to the procedures described in Example 4B, substituting Example 15A for 1-ethynylcyclopentanol used in Example 4B. $^1$H NMR (300 MHz, DMSO-$d_6$) δ 8.47 (s, 1H), 8.31 (brs, 2H), 7.64 (d, J=8.8 Hz, 4H), 7.42 (d, J=8.8 Hz, 4H), 7.12 (brs, 1H), 2.56 (s, 3H). MS (ESI) m/z 424 (M+H)$^+$.

Example 16

5-methyl-6-(3-morpholin-4-yl-3-phenylprop-1-ynyl)[1,2,4]triazolo[1,5-a]pyrimidin-7-amine The title compound was prepared according to the procedures described in Example 4B, substituting 4-(1-phenylprop-2-ynyl)-morpholine (prepared as described in Ahn, Jin Hee; Joung, Meyoung Ju; Yoon, Nung Min; *J. Org. Chem*; EN; 64; 2; 1999; 488-492) for 1-ethynylcyclopentanol used in Example 4B. $^1$H NMR (300 MHz, DMSO-$d_6$) δ 849 (s, 1H), 7.99-7.94 (m, 1H), 7.74-7.65 (m, 1H), 7.63-7.42 (m, 4H), 3.81-3.66 (m, 4H), 3.15-2.90 (m, 4H), 2.60 (s, 3H). MS (ESI) m/z 349 (M+H)$^+$.

Example 17

3-(7-amino-5-methyl[1,2,4]-triazolo[1,5-a]pyrimidin-6-yl)-1-(1-methyl cyclohexyl)-1-phenylprop-2-yn-1-ol

Example 17A
1-(1-methylcyclohexyl)-1-phenylprop-2-yn-1-ol

The title compound was prepared according to the procedures described in Example 6A, substituting (1-methyl-cyclohexyl)-phenyl ketone (prepared as described in Rouzaud, J. et al.; BSCFAS; Bull. Soc. Chim. Fr.; FR; 1965; 2030-2037) for tetrahydro-4H-pyran-4-one used in Example 6A.

Example 17B 3-(7-amino-5-methyl[1,2,4]triazolo[1,5-a]pyrimidin-6-yl)-1-(1-methylcyclohexyl)-1-phenylprop-2-yn-1-ol The title compound was prepared according to the procedures described in Example 4B, substituting Example 17A for 1-ethynylcyclopentanol used in Example 4B, $^1$H-NMR (300 MHz, DMSO-$d_6$) δ 8.47 (s, 1H), 8.20 (brs, 2H), 7.63-7.56 (m, 2H), 7.42-7.23 (m, 3H), 2.65 (s, 3H), 1.74-1.46 (m, 4H), 1.46-0.90 (m, 6H), 0.93 (s, 3H). MS (ESI) m/z 376 (M+H)$^+$.

Example 18

3-(7-amino-5-methyl[1,2,4]triazolo[1,5-a]pyrimidin-6-yl)-1-(3,4'-dichloro-1,1'-biphenyl-4-yl)prop-2-yn-1-ol

Example 18A 1-(3,4'-dichlorobiphenyl-4-yl)prop-2-yn-1-ol

The title compound was prepared according to the procedures described in Example 6A, substituting 3,4'-dichlorobiphenyl-4-carboxaldehyde (prepared as described in WO2001039773A1) for tetrahydro-4H-pyran-4-one used in Example 6A.

Example 18B 3-(7-amino-5-methyl[1,2,4]triazolo[1,5-a]pyrimidin-6-yl)-1-(3,4'-dichloro-1,1'-biphenyl-4-yl)prop-2-yn-1-ol The title compound was prepared according to the procedures described in Example 4B, substituting Example 18A for 1-ethynylcyclopentanol used in Example 4B. $^1$H NMR (300 MHz, DMSO-$d_6$) δ 8.47 (s, 1H), 8.30 (brs, 2H), 7.68-7.60 (in, 4H), 7.46-7.39 (m, 4H), 7.13 (m, 1H), 2.56 (s, 3H). MS (ESI) m/z 424, 426, 428 (M+H)$^+$.

Example 19

1-(7-amino-5-methyl[1,2,4]triazolo[1,5-a]pyrimidin-6-yl)-3-(1,1'-biphenyl-4-yl)-4,4-dimethylpent-1-yn-3-ol

Example 19A 3-(biphenyl-4-yl)-4,4-dimethylpent-1-yn-3-ol

The title compound was prepared according to the procedures described in Example 6A, substituting 4-biphenyl-ter-butyl ketone (prepared as described in Tsuji, Yutaka; Fujio, Mizue; Tsuno, Yuho; Bull. Chem. Soc. Jpn.; 63; 3; 1990; 856-866) for tetrahydro-4H-pyran-4-one used in Example 6A.

Example 19B 1-(7-amino-5-methyl[1,2,4]triazolo[1,5-a]pyrimidin-6-yl)-3-(1,1'-biphenyl-4-yl)-4,4-dimethylpent-1-yn-3-ol The title compound was prepared according to the procedures described in Example 4B, substituting Example 19A for 1-ethynylcyclopentanol used in Example 4B. $^1$H NMR (300 MHz, DMSO-$d_5$) δ 8.45 (s, 1H), 8.20 (brs, 2H), 7.74-7.63 (m, 6H), 7.51-731 (m, 3H), 6.19 (s, 1H), 2.67 (s, 3H), 1.05 (s, 9H). MS (ESI) m/z 412 (M+H)$^+$.

Example 20 methyl 4-(7-amino-5-methyl[1,2,4]triazolo[1,5-a]pyrimidin-6-yl)-2-hydroxy-2-phenylbut-3-ynoate

Example 20A methyl 2-hydroxy-2-phenylbut-3-ynoate

The title compound was prepared according to the procedures described in Example 6A, substituting methyl benzoylformate for tetrahydro-4H-pyran-4-one used in Example 6A.

Example 20B methyl 4-(7-amino-5-methyl[1,2,4]triazolo[1,5-a]pyrimidin-6-yl)-2-hydroxy-2-phenylbut-3-ynoate The title Compound was prepared according to the procedures described in Example 4B, substituting Example 20A for 1-ethynylcyclopentanol used in Example 4B. $^1$H NMR (300 MHz, DMSO-$d_6$) δ 8.45 (s, 1H), 8.20 (brs, 2H), 7.75-7.22 (m, 5H), 3.68 (s, 3H), 2.58 (s, 3H). MS (ESI) m/z 338 (M+H)$^+$.

Example 21

N-{1-[(7-amino-5-methyl[1,2,4]triazolo[1,5-a]pyrimidin-6-yl)ethynyl]cyclohexyl}-3-chlorobenzenesulfonamide

Example 21A 3-chloro-N-(1-ethynylcyclohexyl)benzenesulfonamide

To a solution of 1-ethynylcyclohexanamine (40 mg, 0.32 mmol) in $CH_2Cl_2$, was added triethylamine (68 mL, 0.48 mmol), followed by 3-chlorobenzenesulfonyl chloride (68.2 mg, 0.32 mmol). After 30 min, the mixture was partitioned between ethyl acetate and 3N aq. HCl. The organic layer was washed with sat. $NaHCO_3$, brine, dried over $Na_2SO_4$, concentrated in vacuuo to give the title compound as a white solid (90 mg, 93% yield).

Example 21B

N-{1-[(7-amino-5-methyl[1,2,4]triazolo[1,5-a]pyrimidin-6-yl)ethynyl]cyclohexyl}-3-chlorobenzenesulfonamide The title compound was prepared according to the procedures described in Example 4B, substituting Example 21A for 1-ethynylcyclopentanol used in Example 4B. $^1$H NMR (300 MHz, DMSO-$d_6$) δ 8.47 (s, 1H), 8.17 (s, 1H), 7.80-7.28 (m, 4H), 2.26 (s, 3H), 2.11-1.99 (m, 2H), 1.79-4.38 (m, 6H), 1.32-1.10 (m, 2H). MS (ESI) m/z 445 (M+H)$^+$.

Example 22

N-{4-[(7-amino-5-methyl[1,2,4]triazolo[1,5-a]pyrimidin-6-yl)ethynyl]phenyl}-N'-(3-chlorophenyl)urea To a stirred solution of Example 1 (10 mg, 0.038 mmol) in 1.0 mL of $CH_3CN$ was added 3-chloro-phenyl isocyanate (6.4 mg, 0.046 mmol) and triethylamine (8 μL, 0.057 mmol). The resulting mixture was stirred for over night at room temperature. The resulting mixture was purified by reverse phase HPLC (C-18 column, eluting; with a 5-100% $CH_3CN$ gradient in 0.1% trifluoroacetic acid) to the title compound as its trifluoroacetic acid salt (3.5 mg, 17.3% yield). MS (ESI) m/z 416, 418 (M+H)$^+$.

Example 23

(1R,4R)-2-[(7-amino-5-methyl[1,2,4]triazolo[1,5-a]pyrimidin-6-yl)ethynyl]-1,7,7-trimethylbicyclo[2.2.1]heptan-2-ol

Example 23A (1R,4R)-2-ethynyl-1,7,7-trimethylbicyclo[2.2.1]heptan-2-ol

The title compound was prepared according to the procedures described in Example 6A, substituting (±)-camphor for tetrahydro-4H-pyran-4-one used in Example 6A.

Example 23B (1R,4R)-2-[(7-amino-5-methyl[1,2,4]triazolo[1,5-a]pyrimidin-6-yl)ethynyl]-1,7,7-trimethylbicyclo[2.2.1]heptan-2-ol The title compound was prepared according to the procedures described in Example 4B, substituting Example 23A for 1-ethynylcyclopentanol used in Example 4B. $^1$H NMR (300 MHz, DMSO-$d_6$) δ 8.43 (s, 1H), 8.23 (brs, 2H), 5.55 (s, 1H), 2.59 (s, 3H), −2.50 (s, 3H), 2.24-2.14 (m, 2H), 1.96-1.83 (m, 3H), 1.78-4.63 (m, 3H), 1.54-1.41 (m, 2H), 1.20-1.09 (m, 2H), 1.08 (s, 3H), 0.93 (s, 3H), 0.86 (s, 3H). MS (ESI) m/z 326 (M+H)$^+$.

Example 24

(1Z)-2-[3-(7-amino-5-methyl[1,2,4]triazolo[1,5-a]pyrimidin-6-yl)prop-2-ynyl]-4-tert-butylcyclohexanone oxime Example 24A (Z)-4-tert-butyl-2-(prop-2-ynyl)cyclohexanone oxime A mixture of 4-tert-butyl-2-prop-2-ynyl-cyclohexanone (50 mg, 0.26 mmol) (prepared as described in Dufey, P.; Bull. Soc. Chim. Fr.; 1968, 4653-4662) in 1.0 mL of ethanol was refluxed with hydroxylamine hydrochloride (25 mg, 0.36 mmol) and pyridine (0.25 mL, excess) for 3 h. The mixture was then allowed to cool to room temperature and partitioned between ethyl acetate and 3N aq. HCl. The organic layers were washed with saturated aqueous sodium chloride solution, dried over MgSO$_4$, filtered and concentrated to give the titled compound as a light yellow solid (50 mg, 93% yield).

Example 24B (1Z)-2-[3-(7-amino-5-methyl[1,2,4]triazolo[1,5-a]pyrimidin-6-yl)prop-2-ynyl]-4-tert-butylcyclohexanone oxime The title compound was prepared according to the procedures described in Example 4B, substituting Example 24A for 1-ethynylcyclopentanol used in Example 4B. $^1$H NMR (300 MHz, DMSO-$d_6$) δ 8.42 (s, 1H), 8.15 (brs, 2H), 3.02-2.90 (m, 1H), 2.80-2.69 (m, 1H), 2.50 (s, 3H), 2.60-1.22 (m, 2H), 1.93-1.79 (m, 1H), 1.66-0.95 (m, 3H), 0.87 (s, 9H). MS (ESI) m/z 355 (M+H)$^+$.

Example 25

4-(7-amino-5-methyl[1,2,4]triazolo[1,5-a]pyrimidin-6-yl)-2-(4-isopropyl-2-methylcyclopentyl)but-3-yn-2-ol Example 25A 2-(4-isopropyl-2-methylcyclopentyl)but-3-yn-2-ol The title compound was prepared according to the procedures described in Example 6A, substituting 1-(4-isopropyl-2-methylcyclopentyl)ethanone (prepared as described in Roger, A. et al. Bull. Soc. Chim. Fr. 1967, 3030-3037) for tetrahydro-4H-pyran-4-one used in Example 6A.

Example 25B 4-(7-amino-5-methyl[1,2,4]triazolo[1,5-a]pyrimidin-6-yl)-2-(4-isopropyl-2-methylcyclopentyl)but-3-yn-2-ol The title compound was prepared according to the procedures described in Example 4B, substituting Example 25A for 1-ethynylcyclopentanol used in Example 4B. $^1$H NMR (300 MHz, DMSO-$d_6$) δ 8.46 (s, 1H), 8.22 (brs, 2H), 5.40 (brs, 1H), 2.50 (s, 3H), 2.14-1.97 (m, 1H), 1.85-1.54 (m, 3H), 1.43 (s, 3H), 1.49-1.13 (m, 3H), 1.10&1.08 (s, 3H in total), 0.88 (s, 3H), 0.85 (s, 3H). MS (ESI) m/z 342 (M+H)$^+$.

Example 26 methyl {[3-(7-amino-5-methyl[1,2,4]triazolo[1,5-a]pyrimidin-6-yl)-1-phenylprop-2-ynyl]oxy}acetate Example 26A methyl 2-(1-phenylprop-2-ynyloxy)acetate To a stirred suspension of NaH (60%, 76 mg, 1.89 mmol) in 5 mL of anhydrous N,N-dimethylformamide was added 1-phenylprop-2-yn-1-ol (250 mg, 1.89 mmol). After 15 min at room temperature, methyl bromoacetate (179 μL, 1.89 mmol) was added. The resulting mixture was stirred at room temperature for 90 min before it was quenched with saturated ammonium chloride and extracted with ethyl acetate (2×15 mL). The combined organic layer was washed with brine, dried over Na$_2$SO$_4$, filtered, and concentrated in vacuuo. The residue was purified by flash chromatography on silica gel, eluting with ethyl acetate:hexane (1.9), to provide the title compound as a colorless oil (160 mg, 41% yield).

Example 26B methyl {[3-(7-amino-5-methyl[1,2,4]triazolo[1,5-a]pyrimidin-6-yl)-1-phenylprop-2-ynyl]oxy}acetate The title compound was prepared according to the procedures described in Example 4B, substituting Example 26A for 1-ethynylcyclopentanol used in Example 4B. $^1$H NMR (300 MHz, DMSO-$d_6$) δ 8.44 (s, 1H), 8.44 (brs, 2H), 7.64 (d, J=6.4 Hz, 2H), 7.49-735 (m, 3H), 5.72 (s, 1H), 4.41 (q, J=16.5 Hz, 2H), 1.69 (s, 3H), 2.50 (s, 3H). MS (ESI) m/z 352 (M+H)$^+$.

Example 27

{[3-(7-amino-5-methyl[1,2,4]triazolo[1,5-a]pyrimidin-6-yl)-1-phenylprop-2-ynyl]oxy}acetic acid Example 26B (60 mg, 0.17 mmol) was stirred in methanol/tetrahydrofuran (1 mL, 1:1, v/v) and 3N aq. NaOH (171 μL, 0.51 mmol) was added. The mixture was stirred at room temperature for 5 h. Volatile organic solvent was evaporated in vacuuo and the residue was treated with 1N NaOH to adjust the pH to 5. The precipitate formed was collected through filtration and dried in vacuum oven to give the title compound (25 mg, 45% yield) as a brown solid. $^1$H NMR (300 MHz, DMSO-$d_6$) δ 12.75 (s, 1H), 8.44 (s, 1H), 8.44 (brs, 2H), 7.64 (d, J=6.8 Hz, 2H), 7.48-7.33 (m, 3H), 5.72 (s, 1H), 4.32 (d, J=16.6 Hz, 1H), 4.23 (d, J=16.6 Hz, 1H), 2.52 (s, 3H). MS (ESI) m/z 338 (M+H)$^+$.

Example 28

{2-[(7-amino-5-methyl[1,2,4]triazolo[1,5-a]pyrimidin-6-yl)ethynyl]phenyl}methanol The title compound was prepared according to the procedures described in Example 4B, substituting (2-ethynylphe-

Example 29

{3-[3-(7-amino-5-methyl[1,2,4]triazolo[1,5-a]pyrimidin-6-yl)-1-hydroxy-1-methylprop-2-ynyl]-2,2-dimethylcyclobutyl}acetic acid

Example 29A 2-(3-(2-hydroxybut-3-yn-2-yl)-2,2-dimethylcyclobutyl)acetic acid The title compound was prepared according to the procedures described in Example 6A, substituting 2-(3-acetyl-2,2-dimethylcyclobutyl)acetic acid (prepared as described in Burgess, K. et al. Tetrahedron Lett. 38, 1997, 1681-1684) for tetrahydro-4H-pyran-4-one used in Example 6A.

Example 29B

{3-[3-(7-amino-5-methyl[1,2,4]triazolo[1,5-a]pyrimidin-6-yl)-1-hydroxy-1-methylprop-2-ynyl]-2,2-dimethylcyclobutyl}acetic acid A mixture of Example 4A (28 mg, 0.1 mmol), Example 29A (21 mg, 0.1 mmol), bis(triphenylphosphine)palladium (II) dichloride (3.5 mg, 0.005 mmol). CuI (1 mg, 0.005 mmol), and triethylamine (28 µL, 0.2 mmol) in acetonitrile (500 µL) was heated at 100° C. for 5 min in a microwave reactor under an atmosphere of nitrogen. The resulting mixture was purified by reverse phase HPLC (C-18 column, eluting with a 5-100% $CH_3CN$ gradient in 0.1% trifluoroacetic acid), and further purified by flash chromatograph on silica-gel (eluting with 10% methanol in ethyl acetate) to provide the title compound as a white solid (6 mg, 17% yield). $^1$H NMR (300 MHz, DMSO-$d_6$) δ 11.93 (s, 1H), 8.42 (s, 1H), 8.12 (s, 2H), 5.32 (s, 1H), 2.52 (s, 3H), 1.82-2.32 (m, 6H), 1.42 (s, 3H), 1.12 (s, 6H). MS (ESI) m/z 358 (M+H)$^+$.

Example 30

4-(7-amino-5-methyl[1,2,4]triazolo[1,5-a]pyrimidin-6-yl)-2-cyclobutylbut-3-yn-2-ol The titled compound was prepared according to the procedures described in Example 29B, substituting 2-cyclobutyl-but-3-yn-2-ol (as prepared as described in U.S. Pat. No. 2,779,799) for Example 29A to provide a white solid (11 mg, 41%). $^1$H NMR (300 MHz, DMSO-$d_6$) δ 8.43 (s, 1H), 8.16 (s, 2H), 5.39 (s, 1H), 2.52 (s, 3H), 1.58-2.21 (m, 7H), 1.37 (s, 3H). MS (ESI) m/z 272 (M+H)$^+$.

Example 31

4-(7-amino-5-methyl[1,2,4]triazolo[1,5-a]pyrimidin-6-yl)-2-(3-methylcyclobutyl)but-3-yn-2-ol The titled compound was prepared according to the procedures described in Example 29B, substituting 2-(3-methylcyclobutyl)but-3-yn-2-ol (prepared as described in U.S. Pat. No. 2,779,799) for Example 29A to provide a white solid (4 mg, 14%). $^1$H NMR (300 MHz, DMSO-$d_6$) δ 8.43 (s, 1H), 8.12 (s, 2H), 5.37 (s, 1H), 2.52 (s, 3H), 1.45-2.38 (m, 6H), 1.34 (d, J=7.12 Hz, 3H), 0.93-1.17 (m, 3H). MS (ESI) m/z 286 (M+H)$^+$.

Example 32

5-methyl-6-(3-phenylprop-1-ynyl)[1,2,4]triazolo[1,5-a]pyrimidin-7-amine

The title compound was prepared according to the procedures described in Example 4B, substituting the commercially available prop-2-ynylbenzene for 1-ethynylcyclopentanol used in Example 4B. $^1$H NMR (300 MHz, DMSO-$d_6$) δ 8.41 (s, 1H), 8.27 (s, 2H), 7.21-7.51 (m, 5H), 3.98 (s, 2H), 2.54 (s, 3H). MS (ESI m/z 264 (M+H)$^+$.

Example 33

6-(3-cyclopentylprop-1-ynyl)-5-methyl[1,2,4]triazolo[1,5-a]pyrimidin-7-amine

The title compound was prepared according to, the procedures described in Example 4B, substituting the commercially available prop-2-ynylcyclopentane for 1-ethynylcyclopentanol used in Example 4B. $^1$H NMR (300 MHz, DMSO-$d_6$) δ 8.40 (s, 1H), 8.12 (s, 2H), 2.51 (s, 3H), 2.08-2.22 (m, 1H), 1.73-1.87 (m, 2H), 1.45-1.70 (m, 4H), 1.27-1.42 (m, 2H). MS (ESI) m/z 256 (M+H)$^+$.

Example 34

6-[(1-aminocyclohexyl)ethynyl]-5-methyl[1,2,4]triazolo[1,5-a]pyrimidin-7-amine

The title compound was prepared according to the procedures described in Example 4B, substituting the commercially available 1-ethynylcyclohexanamine for 1-ethynylcyclopentanol used in Example 4B. $^1$H NMR (300 MHz, DMSO-$d_6$) δ 8.69 (s, 1H), 8.49 (brs, 2H), 2.55 (s, 3H), 2.18-2.09 (m, 1H), 2.07-1.96 (m, 1H), 1.84-1.50 (m, 6H), 1.50-1.33 (m, 1H), 1.26-1.05 (m, 1H). MS (ESI) m/z 271 (M+H)$^+$.

Example 35

3-(7-amino-5-methyl[1,2,4]triazolo[1,5-a]pyrimidin-6-yl)-1-cyclopentylprop-2-yn-1-ol

Example 35A 1-cyclopentylprop-2-yn-1-ol

The title compound was prepared according to the procedures described in Example 6A, substituting cyclopentane carboxaldehyde for tetrahydro-4H-pyran-4-one used in Example 6A.

Example 35B 3-(7-amino-5-methyl[1,2,4]triazolo[1,5-a]pyrimidin-6-yl)-1-cyclopentylprop-2-yn-1-ol The title compound was prepared according to the procedures described in Example 4B, substituting Example 35A for 1-ethynylcyclopentanol used in Example 4B. $^1$H NMR (300 MHz, DMSO-$d_6$) δ 8.42 (s, 1H), 8.17 (brs, 2H), 5.37 (d, J=5.1 Hz, 1H), 4.41-4.34 (m, 1H), 2.50 (brs, 3H), 2.30-2.11 (m, 1H), 1.81-1.40 (m, 8H). MS (ESI) m/z 272 (M+H)$^+$.

Example 36

3-(7-amino-5-methyl[1,2,4]triazolo[1,5-a]pyrimidin-6-yl)-1-(2,4-dichlorophenyl)prop-2-yn-1-ol

Example 36A 1-(2,4-dichlorophenyl)prop-2-yn-1-ol

The title compound was prepared according to the procedures described in Example 6A, substituting 2,4-dichlorobenzaldehyde for tetrahydro-4H-pyran-4-one used in Example 6A.

Example 36B 3-(7-amino-5-methyl[1,2,4]triazolo[1,5-a]pyrimidin-6-yl)-1-(2,4-dichlorophenyl)prop-2-yn-1-ol The title compound was prepared according to the procedures described in Example 4B, substituting Example 36A for 1-ethynylcyclopentanol used in Example 4B. $^1$H NMR (300. MHz, DMSO-d$_6$) δ 8.43 (s, 1H), 8.28 (brs, 2H), 7.82 (d, J=8.5 Hz, 1H), 7.65 (d, J=2.0 Hz, 1H), 7.53 (dd, J=8.5, 2.0 Hz, 1H), 6.40 (d, J=5.8 Hz, 1H), 5.88 (d, J=5.8 Hz, 1H), 250 (s, 3H). MS (ESI) m/z 348, 350, 352 (M+H)$^+$.

Example 37

4-(7-amino-5-methyl[1,2,4]triazolo[1,5-a]pyrimidin-6-yl)-1-cyclopentyl-2-methylbut-3-yn-2-ol

Example 37A 1-cyclopentyl-2-methylbut-3-yn-2-ol

The title compound was prepared according to the procedures described in Example 6A, substituting cyclopentylacetone for tetrahydro-4H-pyran-4-one used in Example 6A.

Example 37B 4-(7-amino-5-methyl[1,2,4]triazolo[1,5-a]pyrimidin-6-yl)-1-cyclopentyl-2-methylbut-3-yn-2-ol A mixture of Example 4A (28 mg, 0.1 mmol), Example 37A (18 mg, 0.12 mmol), bis(triphenylphosphine)palladium (II) dichloride (3.5 mg, 0.005 mmol), CuI (1 mg, 0.005 mmol), and triethylamine (28 µL, 0.2 mmol) in acetonitrile (500 µL) was heated at 100° C. for 5 min in a microwave reactor under an atmosphere of nitrogen. The resulting mixture was partitioned between ethyl acetate and water. The organic phase was washed with brine, dried over MgSO$_4$, filtered and concentrated in vacuuo. The residue was purified by flash chromatograph on silica gel (eluting with ethyl acetate) to provide the title compound as a pale yellow solid (9 mg, 30% yield). $^1$H NMR (300 MHz, DMSO-d$_6$) δ 8.42 (s, 1H), 8.13 (s, 2H), 5.38 (s, 1H), 2.49 (s, 3H), 1.99-2.20 (m, 1H), 1.80-1.94 (m, 2H), 1.76 (dd, J=6.27, 2.88 Hz, 2H), 1.49 (s, 3H), 1.37-1.65 (m, 4H), 1.08-1.28 (m, 2H). MS (ESI) m/z 300 (M+H)$^+$.

Example 38

{4-[(7-amino-5-methyl[1,2,4]triazolo[1,5-a]pyrimidin-6-yl)ethynyl]-4-hydroxycyclohexyl}acetic acid Example 43B (5.0 mg) in CH$_2$Cl$_2$/trifluoroacetic acid (0.5 mL, 1:1, v/v) was left at room temperature for 2 h. Solvent was then removed in vacuuo to give the title compound as its trifluoroacetic acid salt (6.0 mg, 100%). $^1$H NMR (300 MHz, DMSO-d$_6$) δ 8.43 (s, 1H), 5.65 (brs, 1H), 2.53 (s, 3H), 2.29-2.08 (m, 2H), 2.05-1.90 (m, 2H), 1.81-1.59 (m, 3H), 1.59-1.44 (m, 2H), 1.41-1.21 (m, 2H). MS (ESI) m/z 330 (M+H)$^+$.

Example 39 methyl {4-[(7-amino-5-methyl[1,2,4]triazolo[1,5-a]pyrimidin-6-yl)ethynyl]-4-hydroxycyclohexyl}acetate

Example 39A methyl 2-(4-ethynyl-4-hydroxycyclohexyl)acetate

The title compound was prepared according to the procedures described in Example 6A, substituting (4-oxo-cyclohexyl)-acetic acid methyl ester (prepared as described in Suemune, Hiroshi; Oda, Kozo; Sakai, Kiyoshi; Tetrahedron Lett.; 28; 29; 1987; 3173-3376) for tetrahydro-4H-pyran-4-one used in Example 6A.

Example 39B methyl {4-[(7-amino-5-methyl[1,2,4]triazolo[1,5-a]pyrimidin-6-yl)ethynyl]-4-hydroxycyclohexyl}acetate The title compound was prepared according to the procedures described in Example 4B, substituting Example 39A for 1-ethynylcyclopentanol used in Example 4B. $^1$H NMR (300 MHz, DMSO-d$_6$) δ 8.45 (s, 1H), 8.18 (brs, 2H), 3.58 (s, 3H), 2.53 (s, 3H), 2.27-22.0 (m, 2H), 2.02-1.94 (m, 2H), 1.77-1.65 (m, 3H), 1.58-1.45 (m, 2H), 1.40-1.24 (m, 2H). MS (ESI) m/z 344 (M+H)$^+$.

Example 40

(1R,4S)-2-[(7-amino-5-methyl[1,2,4]triazolo[1,5-a]pyrimidin-6-yl)ethynyl]bicyclo[2.2.1]heptan-2-ol

Example 40A (1R,4S)-2-ethynylbicyclo[2.2.1]heptan-2-ol

The title compound was prepared according to the procedures described in Example 6A, substituting norcamphor for tetrahydro-4H-pyran-4-one used in Example 6A.

Example 40B (1R,4S)-2-[(7-amino-5-methyl[1,2,4]triazolo[1,5-a]pyrimidin-6-yl)ethynyl]bicyclo[2.2.1]heptan-2-ol The title compound was prepared according to the procedures described in Example 4B, substituting Example 40A for 1-ethynylcyclopentanol used in Example 4B. $^1$H NMR (300 DMSO-d$_6$) δ 8.43 (s, 1H), 8.16 (brs, 2H), 5.45 (brs, 1H), 2.51 (s, 3H), 2.42-2.37 (m, 1H), 2.25-2.10 (m, 2H), 2.04-1.92 (m, 1H), 1.80-1.73 (m, 1H), 1.59-1.45 (m, 1H), 1.39-1.18 (m, MS (ESI) m/z 284 (M+H)$^+$.

Example 41

(1R,2S,4R)-2-[(7-amino-5-methyl[1,2,4]triazolo[1,5-a]pyrimidin-6-yl)ethynyl]-1,7,7-trimethylbicyclo[2.2.1]heptan-2-ol

Example 41A (1R,2S,4R)-2-ethynyl-1,7,7-trimethylbicyclo[2.2.1]heptan-2-ol

The title compound was prepared according to the procedures described in Example 6A, substituting R-(+)-camphor for tetrahydro-4H-pyran-4-one used in Example 6A.

Example 41B (1R,2S,4R)-2-[(7-amino-5-methyl[1,2,4]triazolo[1,5-a]pyrimidin-6-yl)ethynyl]-1,7,7-trimethylbicyclo[2.2.1]heptan-2-ol The title compound was prepared according to the procedures described in Example 4B, substituting Example 41A for 1-ethynylcyclopentanol used in Example 4B. $^1$H NMR (300 MHz, DMSO-d$_6$) δ 8.43 (s, 1H), 8.23 (brs, 2H), 5.5 (s, 1H), 2.50 (s, 3H), 2.50 (s, 3H), 2.24-2.14 (m, 2H), 1.96-1.83 (m, 3H), 1.78-1.63 (m, 3H), 1.54-1.41 (m, 2H), 1.20-1.09 (m, 2H), 1.08 (s, 3H), 0.93 (s, 3H), 0.86 (s, 3H) MS (ESI) m/z 326 (M+H)$^+$

Example 42

(1R,2R,4S)-2-[(7-amino-5-methyl[1,2,4]triazolo[1,5-a]pyrimidin-6-yl)ethynyl]-1,3,3-trimethylbicyclo[2.2.1]heptan-2-ol Example 42A (1R,2S,4S)-2-ethynyl-1,3,3-trimethylbicyclo[2.2.1]heptan-2-ol The title compound was prepared according to the procedures described in Example 6A, substituting (1R)-(−)-fenchone for tetrahydro-4H-pyran-4-one used in Example 6A.

Example 42B (1R,2R,4S)-2-[(7-amino-5-methyl[1,2,4]triazolo[1,5-a]pyrimidin-6-yl)ethynyl]-1,3,3-trimethylbicyclo[2.2.1]heptan-2-ol The title compound was prepared according to the procedures described in Example 4B, substituting Example 42A for 1-ethynylcyclopentanol used in Example 4B. $^1$H NMR (300 MHz, DMSO-d$_6$) δ 8.43 (s, 1H), 8.15 (brs, 2H), 5.30 (s, 1H), 2.52 (s, 3H), 2.02-1.90 (m, 1H), 1.78-0.159 (m, 4H), 1.46-1.31 (m, 1H), 1.19 (s, 3H), 1.14 (s, 3H), 1.12-1.04 (m, 1H), 0.94 (s, 3H). MS (ESI) m/z 326 (M+H)$^+$.

Example 43 tert-butyl {4-[(7-amino-5-methyl[1,2,4]triazolo[1,5-a]pyrimidin-6-yl)ethynyl]-4-hydroxycyclohexyl}acetate

Example 43A tert-Butyl 2-(4-ethynyl-4-hydroxycyclohexyl)acetate

The title compound was prepared according to the procedures described in Example 6A, substituting (4-oxo-cyclohexyl)-acetic acid tert-butyl ester (prepared as described in Suemune, Hiroshi; Oda, Kozo; Sakai, Kiyoshi; Tetrahedron Lett.; 28; 29; 1987; 3373-3376) for tetrahydro-4H-pyran-4-one used in Example 6A.

Example 43B tert-butyl {4-[(7-amino-5-methyl[1,2,4]triazolo[1,5-a]pyrimidin-6-yl)ethynyl]-4-hydroxycyclohexyl}acetate The title compound was prepared according to the procedure described in Example 4B, substituting Example 43A for 1-ethynylcyclopentanol used in Example 4B. $^1$H NMR (300 MHz, DMSO-d$_6$) δ 8.43 (s, 1H), 8.18 (brs, 2H), 5.65 (s, 1H), 2.50 (s, 3H), 2.14-2.08 (m, 2H), 2.03-1.94 (m, 2H), 1.77-1.65 (m, 3H), 1.58-1.45 (m, 2H), 1.40-1.28 (m, 2H), 1.39 (s, 9H). MS (ESI) m/z 386 (M+H)$^+$.

Example 44

(1S,2S,4R)-2-[(7-amino-5-methyl[1,2,4]triazolo[1,5-a]pyrimidin-6-yl)ethynyl]-1,3,3-trimethylbicyclo[2.2.1]heptan-2-ol

Example 44A (1S,2R,4R)-2-ethynyl-1,3,3-trimethylbicyclo[2.2.1]heptan-2-ol

The title compound was prepared according to the procedures described in Example 6A, substituting (1S)-(+)-fenchone for tetrahydro-4H-pyran-4-one used in Example 6A.

Example 44B (1S,2S,4R)-2-[(7-amino-5-methyl[1,2,4]triazolo[1,5-a]pyrimidin-6-yl)ethynyl]-1,3,3-trimethylbicyclo[2.2.1]heptan-2-ol The title compound was prepared according to the procedures described in Example 4B, substituting Example 44A for 1-ethynylcyclopentanol used in Example 4B. $^1$H NMR (300 MHz, DMSO-d$_6$) δ 8.43 (s, 1H), 8.15 (brs, 2H), 5.30 (s, 1H), 2.52 (s, 3H), 2.02-1.90 (m, 1H), 1.78-0.159 (m, 4H), 1.46-1.31 (m, 1H), 1.19 (s, 3H), 1.14 (s, 3H), 1.12-1.04 (m, 1H), 0.94 (s, 3H). MS (ESI) m/z 326 (M+H)$^+$.

Example 45

(1S,2R,4S)-2-[(7-amino-5-methyl[1,2,4]triazolo[1,5-a]pyrimidin-6-yl)ethynyl]-1,7,7-trimethylbicyclo[2.2.1]heptan-2-ol

Example 45A (1S,2R,4S)-2-ethynyl-1,7,7-trimethylbicyclo[2.2.1]heptan-2-ol

The title compound was prepared according to the procedures described in Example 6A, substituting S-(−)-camphor for tetrahydro-4H-pyran-4-one used in Example 6A.

Example 45B (1S,2R,4S)-2-[(7-amino-5-methyl[1,2,4]triazolo[1,5-a]pyrimidin-6-yl)ethynyl]-1,7,7-trimethylbicyclo[2.2.1]heptan-2-ol The title compound was prepared according to the procedures described in Example 4B, substituting Example 45A for 1-ethynylcyclopentanol used in Example 4B. $^1$H NMR (300 MHz, DMSO-d$_6$) δ 8.43 (s, 1H), 8.23 (brs, 2H), 5.55 (s, 1H), 2.50 (s, 3H), 2.50 (s, 3H), 2.24-2.14 (m, 2H), 1.96-1.83 (m, 3H), 1.78-1.63 (m, 3H), 1.54-1.41 (m, 2H), 1.20-1.09 (m, 2H), 1.08 (s, 3H), 0.93 (s, 3H), 0.86 (s, 3H). MS (ESI) m/z 326 (M+H)$^+$.

Example 46

1-[3-(7-amino-5-methyl[1,2,4]triazolo[1,5-a]pyrimidin-6-yl)prop-2-ynyl]cyclopentanol

Example 46A 1-(prop-2-ynyl)cyclopentanol

Magnesium turnings (350 mg, 14.4 mmol) and HgCl$_2$ (16 mg, 0.659 mmol) were stirred with 20 mL of anhydrous diethyl ether in a 100-mL round bottom flask. Propargyl bromide (80% in xylene, 2.5 mL, 13.2 mmol) was added. The mixture was stirred for 30 min at room temperature before cyclopentanone (1.0 g, 11.9 mmol) was added in 4.0 mL tetrahydrofuran. The resulting mixture was refluxed for 2 h, then allowed to cool to room temperature, and quenched with saturated aqueous ammonium chloride (15 mL). The biphasic mixture was extracted with ethyl (50 mL) and the organic layer was washed with brine, dried over Na$_2$SO$_4$, filtered, and concentrated in vacuuo. The residue was purified by flash chromatograph on silica gel (eluting with 10% hexanes in ethyl acetate) to provide the title compound (800 mg, 54%) as a colorless oil.

Example 46B

1-[3-(7-amino-5-methyl[1,2,4]triazolo[1,5-a]pyrimidin-6-yl)prop-2-ynyl]cyclopentanol The title compound was prepared according to the procedures described in Example 4B, substituting Example 46A for 1-ethynylcyclopentanol used in Example 4B. $^1$H NMR (300 MHz, DMSO-d$_6$) δ 8.41 (s, 1H), 8.15 (brs, 2H), 4.68 (s, 1H), 2.75 (s, 2H), 2.50 (s, 3H), 1.80-1.52 (m, 8H). MS (ESI) m/z 272 (M+H)$^+$.

Example 47

1-[(7-amino[1,2,4]triazolo[1,5-a]pyrimidin-6-yl)ethynyl]cyclopentanol

The title compound was prepared according to the procedures described in Example 4B, substituting the commercially available 6-bromo-[1,2,4]triazolo[1,5-a]pyrimidin-7-amine for Example 4A used in Example 4B. $^1$H NMR (300 MHz, DMSO-d$_6$) δ 8.50 (s, 1H), 8.40 (brs, 2H), 8.32 (s, 1H), 5.34 (s, 1H), 2.50 (s, 3H), 2.07-1.63 (m, 8H). MS (ESI) m/z 244 (M+H)$^+$.

Example 48

1-[3-(7-amino[1,2,4]triazolo[1,5-a]pyrimidin-6-yl)prop-2-ynyl]cyclopentanol

The title compound was prepared according to the procedures described in Example 4B, substituting the commercially available 6-bromo-[1,2,4]triazolo[1,5-a]pyrimidin-7-amine for Example 4A, and substituting Example 46A for 1-ethynylcyclopentanol used in Example 4B. $^1$H NMR (300 MHz, DMSO-d$_6$) δ 8.49 (s, 1H), 8.35 (brs, 2H), 8.34 (s, 1H), 4.68 (s, 1H), 2.71 (s, 2H), 2.50 (s, 3H), 1.80-1.53 (m, 8H). MS (ESI) m/z 258 (M+H)$^+$.

Example 49

(1R,2S,4R)-2-[3-(7-amino-5-methyl[1,2,4]triazolo[1,5-a]pyrimidin-6-yl)prop-2-ynyl]-1,7,7-trimethylbicyclo[2.2.1]heptan-2-ol

Example 49A (1R,2S,4R)-1,7,7-trimethyl-2-(prop-2-ynyl)bicyclo[2.2.1]heptan-2-ol The title compound was prepared according to the procedures described in Example 46A, Substituting R-(+)-camphor for cyclopentanone used in Example 46A.

Example 49B (1R,2S,4R)-2-[3-(7-amino-5-methyl[1,2,4]triazolo[1,5-a]pyrimidin-6-yl)prop-2-ynyl]-1,7,7-trimethylbicyclo[2.2.1]heptan-2-ol The title compound was prepared according to the procedures described in Example 4B, substituting Example 49A for 1-ethynylcyclopentanol used in Example 4B. $^1$H NMR (300 MHz, DMSO-d$_6$) δ 8.41 (s, 1H), 8.14 (brs, 2H), 4.56 (s, 1H), 2.73 (s, 2H), 2.53 (s, 3H), 2.01-1.90 (m, 1H), 1.73-1.59 (m, 2H), 1.52-1.32 (m, 3H), 1.09 (s, 3H), 1.16-1.02 (m, 1H), 0.91 (s, 3H), 0.82 (s, 3H). MS (ESI) m/z 340 (M+H)$^+$.

Example 50 methyl 1-[3-(7-amino-5-methyl[1,2,4]triazolo[1,5-a]pyrimidin-6-yl)prop-2-ynyl]cyclohexanecarboxylate

Example 50A methyl 1-(prop-2-ynyl)cyclohexanecarboxylate

To a solution of diisopropylamine (879 μL, 6.22 mmol) in anhydrous tetrahydrofuran (12 mL) at −40° C. under nitrogen was added 1.6 M n-butyl lithium in hexane (3.9 mL, 6.22 mmol), followed by hexamethylphosphoramide (4 mL). The mixture was cooled down to −78° C. and added a solution of methyl cyclohexanecarboxylate (80 7 μL, 5.65 mmol) tetrahydrofuran (4 mL) with the temperature maintained below −70° C. throughout the addition. After 15 min, propargyl bromide (80% w/w in xylene, 2.5 mL, 22.6 mmol) was added, and the reaction mixture was allowed to warm to room temperature. After 30 min, it was quenched with saturated ammonium chloride, and extracted with ethyl acetate. The organic phase was washed with water (×4), dried over MgSO$_4$, filtered and concentrated to get 900 mg the title intermediate as a pale brown oil.

Example 50B methyl 1-[3-(7-amino-5-methyl[1,2,4]triazolo[1,5-a]pyrimidin-6-yl)prop-2-ynyl]cyclohexanecarboxylate A mixture of Example 4A (28 mg, 0.1 mmol), Example 50A (36 mg, 0.2 mmol), bis(triphenylphosphine)palladium (II) dichloride (3.5 mg, 0.005 mmol), CuI (1 mg, 0.005 mmol), and triethylamine (28 μL, 0.2 mmol) in acetonitrile (500 μL) was heated in a sealed tube under nitrogen at 90° C. oil bath for 3 h. The resulting mixture was purified by reverse phase. HPLC (C-18 column, eluting with a 5-100% C$_3$CN gradient in 10 mM aqueous ammonium acetate) to provide the title compound as a pale pink solid (8 mg, 24% yield). $^1$H NMR (300 MHz, DMSO-d$_6$) δ 8.41 (s, 1H), 8.10 (s, 2H), 3.67 (s, 3H), 2.48 (s, 3H), 2.73 (s, 2H), 2.00-2.15 (m, 2H), 1.17-1.68 (m, 8H). MS (ESI) m/z 328 (M+H)$^+$.

Example 51

6-[3-(4-methoxyphenoxy)but-1-ynyl]-5-methyl[1,2,4]triazolo[1,5-a]pyrimidin-7-amine The titled compound was prepared according to the procedures described in Example 50B, substituting 1-(but-3-yn-2-yloxy)-4-methoxybenzene (prepared as described in Harfenist; J. Org. Chem.; 37; 1972; 841) for Example 50A. $^1$H NMR (300 MHz, DMSO-d$_6$) δ 8.42 (s, 1H), 8.28 (s, 2H), 7.05-7.08 (m, 2H), 6.81-6.92 (m, 2H), 5.27 (q, J=6.44 Hz, 3H), 3.70 (s, 3H), 2.38 (s, 3H), 1.69 (d, J=6.44 Hz, 3H). MS (ESI) m/z 324 (M+H)$^+$.

Example 52

(1R)-3-(7-amino-5-methyl[1,2,4]triazolo[1,5a]pyrimidin-6-yl)-1-phenylprop-2-yn-1-ol The title compound was prepared according to the procedures described in Example 4B, substituting the commercially available (S)-1-phenyl-2-propyn-1-ol for 1-ethynylcyclopentanol used in Example 4B. $^1$H NMR (300 MHz, DMSO-d$_6$) δ 8.43 (s, 1H), 8.28 (brs, 2H), 7.60-7.55 (m, 2H), 7.44-7.36 (m, 3H), 7.34-7.27 (m, 1H), 6.08 (d, J=6.1 Hz, 1H), 5.68 (d, J=6.1 Hz, 1H), 2.50 (s, 3H). MS (ESI) m/z 280 (M+H)$^+$.

Example 53

(1S)-3-(7-amino-5-methyl[1,2,4]triazolo[1,5-a]pyrimidin-6-yl)-1-phenylprop-2-yn-1-ol The title compound was prepared according to the procedures described in Example 4B, substituting the commercially available (R)-1-phenyl-2-propyn-1-ol for 1-ethynylcyclopentanol used in Example 4B. $^1$H NMR (300 MHz, DMSO-d$_6$) δ 8.43 (s, 1H), 8.28 (brs, 2H), 7.60-7.55 (m, 2H), 7.44-7.36 (m, 3H), 7.34-7.27 (m, 1H), 6.08 (d, J=6.1 Hz, 1H), 5.68 (d, J=6.1 Hz, 1H), 2.50 (s, 3H). MS (ESI) m/z 280 (M+H)$^+$.

Example 54

4-(7-amino-5-methyl[1,2,4]triazolo[1,5-a]pyrimidin-6-yl)-1-phenylbut-3-yn-1-ol

The titled compound was prepared as described in Example 50B, substituting 1-phenyl-3-butyn-1-ol for Example 50A. $^1$H NMR (300 MHz, DMSO-d$_6$) δ 8.40 (s, 1H), 8.09 (s, 2H), 7.20-7.49 (m, 5H), 5.67 (d, J=4.07 Hz, 1H), 4.75-4.97 (m, 1H), 2.89 (dd, J=6.27, 1.53 Hz, 2H), 2.35 (s, 3H). MS (ESI) m/z 294 (M+H)$^+$.

Example 55

(trans)-ethyl 2-[3-(7-amino-5-methyl[1,2,4]triazolo[1,5-a]pyrimidin-6-yl)-1-hydroxyprop-2-ynyl]cyclopropanecarboxylate Example 55A (trans)-ethyl 2-(-1-hydroxyprop-2-ynyl)cyclopropanecarboxylate A solution of ethyl 2-formyl-1-cyclopropanecarboxylate (predominately trans, 331 μL, 2.5 mmol) in tetrahydrofuran (5 mL) was cooled down to −70° C. Ethynylmagnesium bromide (0.5 M in tetrahydrofuran, 5 mL, 2.5 mmol) was added to the above solution under an atmosphere of nitrogen dropwise, and stirred at −70° C. for 1 h. The reaction was quenched with water, and extracted with ethyl acetate. The organic phase was washed with brine, dried over MgSO$_4$, filtered and concentrated to get 419 mg of the title compound (yield 100%, unpurified) as a pale yellow oil.

Example 55B (trans)-ethyl 2-[3-(7-amino-5-methyl[1,2,4]triazolo[1,5-a]pyrimidin-6-yl)-1-hydroxyprop-2-ynyl]cyclopropanecarboxylate A mixture of Example 4A (28 mg, 0.1 mmol), Example 55A (20 mg, 0.12 mmol), bis(triphenylphosphine)palladium (II) dichloride (3.5 mg, 0.005 mmol), CuI (1 mg, 0.005 mmol), and triethylamine (28 μL, 0.2 mmol) in acetonitrile (500 μL) was heated in a sealed tube under an atmosphere of nitrogen with 90° C. oil bath for 1.5 h. The resulting mixture was partitioned between ethyl acetate and water. The organic phase was washed with brine, dried (MgSO$_4$), filtered and concentrated in vacuuo. The residue was purified by flash chromatograph on silica gel (eluting with ethyl acetate) to provide the title compound as a white solid (2 mg, 6% yield). $^1$H NMR (500 MHz, DMSO-d$_6$) δ 8.43 (s, 1H), 8.26 (s, 2H), 5.67 (dd, J=13.73, 6.10 Hz, 1H), 4.39-4.65 (m, 1H), 4.07 (q, J=7.02 Hz, 2H), 2.47 (s, 3H), 1.69-1.86 (m, 2H), 1.19 (t, J=7.02 Hz, 2H), 1.03-1.14 (m, 2H). MS (ESI) m/z 316 (M+H)$^+$.

Example 56

1-[3-(7-amino-5-methyl[1,2,4]triazolo[1,5-a]pyrimidin-6-yl)prop-2-ynyl]cyclohexanecarboxylic acid To a solution of Example 69 (83 mg, 0.2 mmol) in tetrahydrofuran (2 mL) was added tetrabutyl ammonium fluoride (1M in tetrahydrofuran, 500 µL, 0.5 mmol) at room temperature, and stirred at room temperature for 24 h. The reaction was quenched with 2N HCl (3 mL). After 5 min, it was adjusted to pH ~4-5 with saturated NaHCO$_3$, and partitioned between ethyl acetate and water. The organic phase was washed with brine, dried (MgSO$_4$), filtered and concentrated in vacuuo to provide the title compound as an off-white solid (63 mg, 100%). $^1$H NMR (300 MHz, DMSO-D6) δ 12.53 (s, 1H), 8.40 (s, 1H), 8.09 (s, 2H), 2.70 (s, 2H), 2.49 (s, 3H), 2.01-2.14 (m, 2H), 1.20-1.65 (m, 8H). MS (ESI) m/z 3.14 (M+H)$^+$.

Example 57

1-[(7-amino-5-ethyl[1,2,4]triazolo[1,5-a]pyrimidin-6-yl)ethynyl]cyclopentanol

Example 57A 5-ethyl-[1,2,4]triazolo[1,5-a]pyrimidin-7-amine

A mixture of 3-oxopentanenitrile (1.0 g, 10.3 mmol) and 3-amino-1,2,4-triazole (0.91 g, 10.8 mmol) in 10 mL of acetic acid was heated in a pressure tube at 150° C. for 24 h. The reaction mixture was allowed to cool to room temperature, and solvent was removed in vacuo. The solid was removed via filtration. The filtrate partially upon standing at room temperature, and the solid was collected via filtration to give the title compound (200 mg, 12% yield).

Example 57B 5-ethyl-6-iodo-[1,2,4]thiazolo[1,5-a]pyrimidin-7-amine

The title compound was prepared according to the procedures described in Example 4A, substituting Example 57A for 5-methyl[1,2,4]triazolo[1,5-a]pyrimidin-7-amine used in Example 4A Example 57C 1-[(7-amino-5-ethyl[1,2,4]triazolo[1,5-a]pyrimidin-6-yl)ethynyl]cyclopentanol The title compound was prepared according to the procedures described in Example 4B, substituting Example 57B for Example 4A used in Example 4B. $^1$H NMR (300 MHz, DMSO-d$_6$) δ 8.44 (s, 1H), 8.12 (brs, 2H), 5.37 (s, 1H), 2.84 (q, J=7.5 Hz, 2H), 2.05-1.62 (m, 8H), 1.24 (t, J=7.5 Hz, 3H). (MS (ESI) m/z 272 (M+H)$^+$.

Example 58

3-(7-amino-5-methyl[1,2,4]triazolo[1,5-a]pyrimidin-6-yl)-1-phenylprop-2-yn-1-one Example 11 (35 mg, 0.153 mmol) was suspended in 1.0 mL of CH$_2$Cl$_2$. Dess-Martin reagent (100 mg, 0.235 mmol) was then added. The resulting milky mixture was stirred at room temperature for 5 h. Solvent was removed in vacuuo, the residue was taken up in DMSO/methanol (1.5 mL, 1:1, v/v); and filtered through celite. The filtrate was purified using reverse phase HPLC (C-18 column, eluting with a 5-100% CH$_3$CN gradient in 10 mM ammonium acetate$_{(aq.)}$) to give the title compound (5 mg, 14%). $^1$H NMR (300 MHz, DMSO-d$_6$) δ 8.84 (brs, 2H), 8.50 (s, 1H), 8.25-8.18 (m, 2H), 7.79-7.58 (m, 3H), 2.67 (s, 3H). MS (ESI) m/z 278 (M+H)$^+$.

Example 59

2-{3-[3-(7-amino-5-methyl[1,2,4]triazolo[1,5-a]pyrimidin-6-yl)-1-hydroxy-1-methylprop-2-ynyl]-2,2-dimethylcyclobutyl}acetamide Example 59A 2-(3-(2-hydroxybut-1-yn-2-yl)-2,2-dimethylcyclobutyl)acetamide To a mixture of Example 29A (84 mg, 0.4 mmol), ammonium chloride (32 mg, 0.6 mmol), O-(benzotriazol-1-yl)-N,N,N',N'-tetramethyluronium tetrafluoroborate (154 mg, 0.48 mmol) in N,N-dimethylformamide was added N,N-diisopropylethylamine (348 µL, 2.0 mmol). The reaction mixture was stirred at room temperature overnight. It was partitioned between ethyl acetate and saturated NaHCO$_3$. The organic phase was washed with brine twice, dried (MgSO$_4$), filtered and concentrated in vacuo to provide the title intermediate as a white solid (50 mg, 60% yield).

Example 59B

2-{3-[3-(7-amino-5-methyl[1,2,4]triazolo[1,5-a]pyrimidin-6-yl)-1-hydroxy-1-methylprop-2-ynyl]-2,2-dimethylcyclobutyl}acetamide The titled compound was prepared as described in Example 29B, substituting Example 59A for Example 29A. $^1$H NMR (300 MHz, DMSO-d$_6$) δ 8.43 (s, 1H), 7.94 (s, 2H), 7.18 (s, 1H), 6.61 (s, 1H), 5.30 (s, 1H), 2.52 (s, 3H), 1.79, 2.15 (m, 5H), 1.58-4.75 (m, 1H), 1.42 (s, 3H), 1.13 (s, 3H), 1.10 (s, 3H). MS (ESI) m/z 357 (M+H)$^+$.

Example 60

(1R,2S,4R)-2-[(7-amino-5-ethyl[1,2,4]triazolo[1,5-a]pyrimidin-6-yl)ethynyl]-1,7,7-trimethylbicyclo[2.2.1]heptan-2-ol The title compound was prepared according to the procedures described in Example 4B, substituting Example 57B for Example 4A, and substituting the product of Example 41A for 1-ethynylcyclopentanol used in Example 4B. $^1$H NMR (300 MHz, DMSO-d$_6$) δ 8.44 (s, 1H), 8.18 (brs, 2H), 5.57 (s, 1H), 2.83 (q, J=7.5 Hz, 2H), 2.29-2.14 (m, 1H), 1.96-1.82 (m, 2H), 1.78-1.64 (m, 2H), 1.55-1.41 (m, 1H), 1.24 (t, J=7.5 Hz, 3H), 1.18-1.09 (m, 1H), 1.08 (s, 3H), 0.93 (s, 3H), 0.86 (s, 3H). MS (ESI) m/z 340 (M+H)$^+$.

Example 61

1-[(7-amino-5-methyl[1,2,4]triazolo[1,5-a]pyrimidin-6-yl)ethynyl]cycloheptanol

The title compound was prepared according to the procedures described in Example 4B, substituting the commercially available 1-ethynylcycloheptanol for 1-ethynylcyclopentanol used in Example 4B. $^1$H NMR (300 MHz, DMSO-d$_6$) δ 8.42 (s, 1H), 8.15 (brs, 2H), 5.41 (s, 1H), 2.50 (s, 3H), 2.08-1.97 (m, 2H), 1.87-1.76 (m, 2H), 1.71-1.46 (m, 8H). MS (ESI) m/z 286 (M+H)$^+$.

Example 62

{[3-(7-amino-5-methyl[1,2,4]triazolo[1,5-a]pyrimidin-6-yl)-1-cyclopentylprop-2-ynyl]oxy}acetic acid To a stirring solution of Example 35B (20 mg, 0.074 mmol) in 0.5 mL of anhydrous N,N-dimethylformamide was added NaH (60%, 4.0 mg, 0.096 mmol). The resulting mixture was stirred for 20 min before tert-butyl bromoacetate (11 µL, 0.0.74 mmol) was added, and stirring continued for 2 h. The reaction mixture was then partitioned between ethyl acetate (10 mL) and brine (10 mL), the organic layer was dried over $MgSO_4$, filtered, evaporated to dryness in vacuuo. The residue was treated with 1.0 mL of 4N HCl in 1,4-dioxane for 3 h. Organic solvent was then removed on a rotavap, and the residue was purified using reverse phase HPLC (C-18 column, eluting with a 5-100% $CH_3CN$ gradient in 10 mM ammonium acetate$_{(aq.)}$) to give the title Compound (5 mg, 21% yield). $^1$H NMR (300 MHz, DMSO-$d_6$) δ 8.45 (s, 1H), 8.15 (brs, 2H), 4.79-4.60 (m, 2H), 4.34 (d, J=7.1 Hz, 1H), 2.54 (s, 3H), 2.25-2.15 (m, 1H), 1.81-1.38 (m, 8H). MS (ESI) m/z 330 (M+H)$^+$.

Example 63

({1-[(7-amino-5-methyl[1,2,4]triazolo[1,5-a]pyrimidin-6-yl)ethynyl]cyclopentyl}oxy)acetic acid The title compound was prepared according to the procedures described in Example 62, substituting. Example 4B for Example 35B. $^1$H NMR (300 MHz, DMSO-$d_6$) δ 8.46 (s, 1H), 8.36 (brs, 2H), 6.27-6.23 (m, 1H), 3.91 (s, 1H), 2.52 (s, 3H), 2.60-2.39 (m, 4H), 1.97-1.86 (m, 4H). MS (ESI) m/z 298 (M–$H_2O$)$^+$.

Example 64

3-(7-amino-5-methyl[1,2,4]triazolo[1,5-a]pyrimidin-6-yl)-1-cyclohexylprop-2-yn-1-ol

Example 64A 1-cyclohexylprop-2-yn-1-ol

The title compound was prepared according to the procedures described in Example 6A, substituting cyclohexane carboxaldehyde for tetrahydro-4H-pyran-4-one used in Example 6A.

Example 64B 3-(7-amino-5-methyl[1,2,4]triazolo[1,5-a]pyrimidin-6-yl)-1-cyclohexylprop-2-yn-1-ol The titled compound was prepared as described in Example 4B, substituting Example 64A for 1-ethynylcyclopentanol used in Example 4B. $^1$H NMR (300 MHz, DMSO-$d_6$) δ 8.43 (s, 1H), 8.19 (s, 2H), 5.30 (d, 5.09 Hz, 1H), 4.39-4.24 (m, 1H), 2.52 (s, 3H), 2.01-0.96 (m, 11H). MS (ESI) m/z 286 (M+H)$^+$.

Example 65 methyl 4-[3-(7-amino-5-methyl[1,2,4]triazolo[1,5-a]pyrimidin-6-yl)-1-hydroxyprop-2-ynyl]cyclohexanecarboxylate

Example 65A methyl 4-formylcyclohexanecarboxylate 4-hydroxymethyl-1-cyclohexanecarboxylic acid (1.58 g, 10 mmol) was dissolved in HCl saturated methanol (20 mL). It was heated in an oil bath (70-80° C.) for 3 h. The reaction mixture was concentrated in vacuuo, and co-evaporated with ethyl acetate to get 1.8 g of oil (>100%). Half of this batch (~5 mmol) in tetrahydrofuran (15 mL) was treated with Dess-Martin periodinane (2.8 g, 6.6 mmol) at room temperature for 1 h. The resulting mixture was concentrated, and purified by flash chromatograph on silica gel (eluting with 20-40% ethyl acetate in Hexane) to provide the title compound as a colorless oil (540 mg, 64% yield).

Example 65B methyl 4-(1-hydroxyprop-2-ynyl)cyclohexanecarboxylate

The title compound was prepared according to the procedures described in Example 6A, substituting Example 65A for tetrahydro-4H-pyran-4-one used in Example 6A.

Example 65C methyl 4-[3 (7-amino-5-methyl[1,2,4]triazolo[1,5-a]pyrimidin-6-yl)-1-hydroxyprop-2-ynyl]cyclohexanecarboxylate The title compound was prepared as described in Example 4B, substituting Example 65B for 1-ethynylcyclopentanol used in Example 4B. $^1$H NMR (300 MHz, DMSO-$d_6$) δ 8.43 (s, 1H), 8.00 (s, 2H), 5.33 (d, J=4.41 Hz, 1H), 4.30-4.44 (m, 1H), 3.60 (s, 3H), 2.60-2.72 (m, 1H), 2.49 (s, 3H), 1.21-2.15 (m, 9H). MS (ESI) m/z 344 (M+H)$^+$.

Example 66

4-[3-(7-amino-5-methyl[1,2,4]triazolo[1,5-a]pyrimidin-6-yl)-1-hydroxyprop-2-ynyl]cyclohexanecarboxylic acid To a solution of Example 65C (26.5 mg, 0.077 mmol) in tetrahydrofuran (0.5 mL)/methanol (0.5 mL) was added 2N NaOH (77 µL, 0.154 mmol). The reaction mixture was stirred at room temperature overnight, and neutralized with 2N HCl (0.154 mmol). It was purified by reverse phase HPLC C-18 column, eluting with a 5-100% $CH_3CN$ gradient in 10 mM ammonium acetate$_{(aq.)}$) to provide the title compound as a white solid (10 mg, 40% yield). $^1$H NMR (300 MHz, DMSO-$d_6$) δ 8.42 (s, 1H), 8.31 (s, 2H), 5.31 (s, 1H), 4.37 (d, J=5.43 Hz, 1H), 2.49 (s, 3H), 2.48-2.50 (m, 1H), 1.26-2.13 (m, 9H). MS (ESI) m/z 330 (M+H)$^+$.

Example 67

{3-[3-(7-amino-5-methyl[1,2,4]triazolo[1,5-a]pyrimidin-6-yl)-1-methyleneprop-2-ynyl]-2,2-dimethylcyclobutyl}acetic acid

Example 67A 2-(3-(but-1-en-3-yn-2-yl)-2,2-dimethylcyclobutyl) acetic acid

To a stirred solution of Example 29A (253 mg, 1.2 mmol) in 5 mL of $CH_2Cl_2$ was added triethylsilane (250 µL, 1.6 mmol), followed by trifluoroacetic acid (116 µL, 1.6 mmol). The resulting mixture was stirred at room temperature for over night. Volatile organics were removed in vacuuo and the residue was evaporated with toluene (2×10 mL). The resulting title compound was used without further purification.

Example 67B

{3-[3-(7-amino-5-methyl[1,2,4]triazolo[1,5-a]pyrimidin-6-yl)-1-methyleneprop-2-ynyl]-2,2-dimethylcyclobutyl}acetic acid The title compound was prepared according to the procedures described in Example 4B, substituting Example 67A for 1-ethynylcyclopentanol used in Example 4B. $^1$H NMR (300 MHz, DMSO-$d_6$) δ 8.42 (s, 1H), 7.86 (brs, 2H), 6.07-5.96 (m, 2H); 2.67-2.11 (m, 5H), 2.52 (s, 3H), 1.94-1.87 (m, 1H), 1.41 (s, 3H), 1.26 (s, 3H). MS (ESI) ink 340 (M+H)$^+$.

Example 68 methyl 1-[3-(7-amino-5-methyl[1,2,4]triazolo[1,5-a]pyrimidin-6-yl)prop-2-ynyl]cyclopentanecarboxylate

Example 68A methyl 1-(prop-2-ynyl)cyclopentanecarboxylate

The title compound was prepared according to the procedures described in Example 50A, substituting methyl cyclopentanecarboxylate for methyl cyclohexanecarboxylate.

Example 68B methyl 1-[3-(7-amino-5-methyl[1,2,4]triazolo[1,5-a]pyrimidin-6-yl)prop-2-ynyl]cyclopentanecarboxylate The titled compound was prepared as described in Example 4B, substituting Example 68A for 1-ethynylcyclopentanol used in Example 4B. $^1$H NMR (300 MHz, DMSO-$d_6$) δ 8.40 (s, 1H), 8.13 (s, 2H), 3.66 (s, 3H), 2.82 (s, 2H), 2.46 (s, 3H), 1.96-2.17 (m, 2H), 1.54-1.83 (m, 6H). MS (ESI) m/z 314 (M+H)$^+$.

Example 69

2-(trimethylsilyl)ethyl 1-[3-(7-amino-5-methyl[1,2,4]triazolo[1,5-a]pyrimidin-6-yl)prop-2-ynyl]cyclohexanecarboxylate

Example 69A 2-trimethylsilyl)ethyl cyclohexanecarboxylate

To a mixture of cyclohexanecarboxylic acid (1.28 g, 10 mmol), 2-(trimethylsilyl)ethanol (1.3 g, 11 mmol), 1-ethyl-3-[3-(dimethylamino)propyl]carbodiimide hydrochloride (2.11 g, 11 mmol) in dichloromethane was added 4-dimethylaminopyridine (123 mg, 1.0 mmol). The reaction mixture was stirred at room temperature for 3 d. It was partitioned between ethyl acetate and 2N HCl. The organic phase was washed with brine, saturated $NaHCO_3$, brine, dried over $MgSO_4$, filtered and concentrated in vacuuo. The residue was purified by flash chromatograph on silica gel (eluting with 0-20% ethyl acetate in hexane) to provide the title compound as a colorless oil (1.7 g, 75% yield).

Example 69B 2-(trimethylsilyl)ethyl 1-(prop-2-ynyl)cyclohexanecarboxylate

The titled compound was prepared as described in Example 50A, substituting Example 69A for methyl cyclohexanecarboxylate used in Example 50A (yield 39%).

Example 69C 2-(trimethylsilyl)ethyl 1-[3-(7-amino-5-methyl[1,2,4]triazolo[1,5-a]pyrimidin-6-yl)prop-2-ynyl]cyclohexanecarboxylate The titled compound was prepared as described in Example 4B, substituting Example 69B for 1-ethynylcyclopentanol used in Example 4B (Yield 39%). $^1$H NMR (300 MHz, DMSO-$d_6$) δ 8.39 (s, 1H), 8.10 (s, 2H), 4.07-4.20 (m, 2H), 2.70 (s, 2H), 2.47 (s, 3H), 2.00-2.18 (m, 2H), 1.19-1.67 (m, 8H), 0.86-0.99 (m, 2H), −0.01 (s, 9H). MS (ESI) m/z 414 (M+H)$^+$.

Example 70

6-[(4-bromophenyl)ethynyl]-5-methyl[1,2,4]triazolo[1,5-a]pyrimidin-7-amine

The title compound was prepared according to the procedures described in Example 4B, substituting the commercially available 1-bromo-4-ethynylbenzene for 1-ethynylcyclopentanol used in Example 4B. $^1$H NMR (300 MHz, DMSO-$d_6$) δ 8.52 (s, 2H), 8.45 (s, 1H), 7.65 (s, 4H), 2.61 (s, 3H). MS (ESI) m/z'328 (M+H)$^+$.

Example 71

6-[(4-chlorophenyl)ethynyl]-5-methyl[1,2,4]triazolo[1,5-a]pyrimidin-7-amine

The title compound was prepared according to the procedures described in Example 4B, substituting the commercially available 1-chloro-4-ethynylbenzene for 1, ethynylcyclopentanol used in Example 4a. $^1$H NMR (300 MHz, DMSO-$d_6$) δ 8.51 (s, 2H), 8.45 (s, 1H), 7.68-73.6 (m, 2H), 7.45-7.54 (m, 2H), 2.61 (s, 3H). MS (ESI) m/z 283 (M+H)$^+$.

Example 72 methyl 2-{4-[(7-amino-5-methyl[1,2,4]triazolo[1,5-a]pyrimidin-6-yl)ethynyl]phenyl}-2-methylpropanoate

Example 72A 5-methyl-6-((trimethylsilyl)ethynyl)-[1,2,4]triazolo[1,5-a]pyrimidin-7-amine A mixture, of Example 4A (275 mg, 1.0 mmol), ethynyltrimethylsilane (283 µL, 2.0 mmol), bis(triphenylphosphine)

palladium(II) dichloride (35 mg, 0.05 mmol), CuI (10 mg, 0.05 mmol), and triethylamine (279 μL, 2 mmol) in acetonitrile (4 mL) was heated at 90° C. under an atmosphere of nitrogen for 1 h. The resulting mixture was partitioned between ethyl acetate and water. The organic phase was washed with brine, dried (MgSO₄), filtered and concentrated in vacuuo. The residue was purified by flash chromatograph on silica gel (eluting with ethyl acetate) to provide the title compound as a pale yellow solid (123 mg, 50% yield).

Example 72B 6-ethynyl-5-methyl-[1,2,4]triazolo[1,5-a]pyrimidin-7-amine

A mixture of Example 72A (122 mg, 0.5 mmol), potassium carbonate (138 mg, 1.0 mmol) in a mixed solvent of methanol/tetrahydrofuran/H₂O (3 mL/3 mL/0.5 mL) was stirred at room temperature for 1.5 h. The reaction mixture was acidified with 1N HCl. The solid was filtered, washed with water and ethyl acetate to provide the title compounds an off-white solid (35 mg, 40% yield).

Example 72C methyl 2-{-4-[(7-amino-5-methyl[1,2,4]triazolo[1,5-a]pyrimidin-6-yl)ethynyl]phenyl}-2-methylpropanoate A mixture of Example 72B (17 mg, 0.1 mmol), methyl 2-(4-bromophenyl)-2-methylpropanoate (38 mg, 6.15 mmol), bis(triphenylphosphine)palladium(10 dichloride (3.5 mg, 0005 mmol), CuI (1 mg, 0.005 mmol), and triethylamine (28 μL, 0.2 mmol) in acetonitrile (500 μL) was heated at 95° C. under nitrogen for 1 h. The resulting mixture was partitioned between ethyl acetate and water. The organic phase was washed with brine, dried over MgSO₄, filtered, and concentrated in vacuuo. The residue was purified by flash chromatograph on silica gel (eluting with ethyl acetate) to provide the title compound as a white solid (16 mg, 45% yield). ¹H NMR (300 MHz, DMSO-d₆) δ 8.44 (s, 3H), 7.64 (d, J=8.48 Hz, 2H), 7.36 (d, J=8.48 Hz, 2H), 3.61 (s, 3H), 2.60 (s, 3H), 1.52 (s, 6H). MS (ESI) m/z 350 (M+H)⁺.

Example 73 ethyl 1-[4-(7-amino-5-methyl[1,2,4]triazolo[1,5-a]pyrimidin-6-yl)but-3-ynyl]-2-oxocyclopentanecarboxylate The title compound was prepared according to the procedures described in Example 4B, substituting 1-but-3-ynyl-2-oxo-cyclopentanecarboxylic acid ethyl ester (prepared as described in Belotti, D.; Cossy, J.; Pete, J. P.; Portella, C.; *J. Org. Chem.;* 51; 22; 1986; 4196-4200) for 1-ethynylcyclopentanol used in Example 4B. ¹H NMR (300 MHz, DMSO-d₆) δ 8.41 (s, 1H), 8.18 (brs, 2H), 4.03 (q, J=7.1 Hz, 2H), 2.87 (t, J=6.8 Hz, 2H), 2.76-2.68 (m, 2H), 2.58-2.23 (m, 6H), 2.50 (s, 3H), 1.15 (t, J=7.1 Hz, 3H). MS (ESI) m/z 356 (M+H)⁺.

It is understood that the foregoing detailed description and accompanying examples are merely, illustrative and are not to be taken as limitations upon the scope of the invention. Various changes and modifications including, but not limited to, those relating to the chemical structures, substituents, derivatives, intermediates, syntheses, formulations and/or methods of use of the invention, can be made without departing from the spirit of the present invention and scope thereof.

We claim:
1. A method for treating a disorder selected from the group consisting of type 2 diabetes, obesity, elevated plasma triglycerides, metabolic syndrome, non-alcoholic steatohepatitis, and non-alcoholic fatty liver disease, said method comprising the step of administering to a subject in need thereof a compound of formula (I),

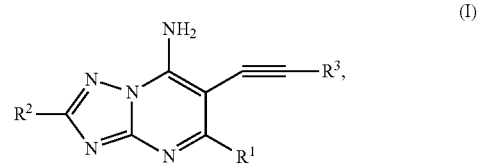

or a pharmaceutically acceptable salt thereof, wherein
$R^1$ is hydrogen or alkyl;
$R^2$ is hydrogen;
$R^3$ is cycloalkyl, aryl, heteroaryl, heterocycle, $-(CR^aR^b)_m-R^4$, $-C(O)OR^5$, $-C(R^5)=N-O(R^y)$, $-C(O)-R^5$, or $-C(O)-N(R^5)(R^6)$;
m is 1, 2, 3 or 4;
$R^a$, at each occurrence, is independently hydrogen, halogen, alkyl, alkenyl, haloalkyl, $-OR^{7a}$, $-N(R^8)(R^9)$, $-C(O)OR^{7b}$, $-C(O)-R^{7b}$, $-C(O)-N(R^8)(R^9)$, $-(CR^cR^d)_p-OR^{7a}$, $-(CR^cR^d)_p-N(R^8)(R^9)$, $-(CR^cR^d)_p-C(O)OR^{7b}$, $-(CR^cR^d)_p-C(O)-R^{7b}$, $-(CR^cR^d)_p-C(O)-N(R^8)(R^9)$, aryl, heteroaryl, cycloalkyl, or heterocycle;
$R^b$, at each occurrence, is independently hydrogen, halogen, alkyl, alkenyl, haloalkyl, $-C(O)OR^{7b}$, $-C(O)-R^{7b}$, $-C(O)-N(R^8)(R^9)$, $-(CR^cR^d)_p-OR^{7a}$, $-(CR^cR^d)_p-N(R^8)(R^9)$, $-(CR^cR^d)_p-C(O)OR^{7b}$, $-(CR^cR^d)_p-C(O)-R^{7b}$, $-(CR^cR^d)_p-C(O)-N(R^8)(R^9)$, aryl, heteroaryl, cycloalkyl, or heterocycle;
optionally, $R^a$ and $R^b$ together is $=CH_2$;
$R^c$ and $R^d$, at each occurrence, are each independently hydrogen halogen, alkyl, or haloalkyl;
$R^y$ is hydrogen, alkyl, haloalkyl, cycloalkyl, aryl, heteroaryl, heterocycle, cycloalkylalkyl, arylalkyl, heteroarylalkyl, or heterocyclealkyl;
$R^4$ is hydrogen, alkyl, haloalkyl, cycloalkyl, aryl, heteroaryl, or heterocycle, provided that when $R^4$ is hydrogen, alkyl or haloalkyl, then at least one $R^a$ is $-OR^{7a}$, $-N(R^8)(R^9)$, $-C(O)OR^{7b}$, $-C(O)-R^{7b}$, $-C(O)-N(R^8)(R^9)$, $-(CR^cR^d)_p-OR^{7a}$, $-(CR^cR^d)_p-N(R^8)(R^9)$, $-(CR^cR^d)_p-C(O)OR^{7b}$, $-(CR^cR^d)_p-C(O)-R^{7b}$, or $-(CR^cR^d)_p-C(O)-N(R^8)(R^9)$; or $R^a$ and $R^b$ together is $=CH_2$;
$R^5$, at each occurrence, is independently alkyl, haloalkyl cycloalkyl, aryl, heteroaryl, heterocycle, cycloalkylalkyl, arylalkyl, heteroarylalkyl, or heterocyclealkyl;
wherein each of the cycloalkyl, aryl, heteroaryl, heterocycle, cycloalkyl moiety of the cycloalkylalkyl, aryl moiety of the arylalkyl, heteroaryl moiety of the heteroarylalkyl, and heterocycle moiety of the heterocyclealkyl, as represented by $R^3$, $R^a$, $R^b$, $R^4$, $R^5$, and $R^y$ is independently unsubstituted or further substituted with 1, 2, 3, 4 or 5 substituents selected from the group consisting of alkyl, halogen, haloalkyl, oxo, $-OR^{10}$, $-S(R^{14})$, $-S(O)_2R^{15}$, $-S(O)_2N(R^{11})(R^{12})$, $-N(R^{11})(R^{12})$, $-C(O)OR^{10}$, $-C(O)O(trialkylsilylalkyl)$, $-C(O)N(R^{11})(R^{12})$, $-(CR^eR^f)_q-OR^{10}$, $-(CR^eR^f)_q-N(R^{11})(R^{12})$, $-(CR^eR^f)_q-C(O)OR^{10}$, $-(CR^eR^f)_q-C(O)N(R^{11})(R^{12})$, $G^1$, and $=N-O(R^{10})$;

R⁶, R⁹ and R¹², at each occurrence, are each independently hydrogen, alkyl or haloalkyl;

R⁷ᵃ, at each occurrence, is each independently hydrogen, alkyl, haloalkyl, —N=C(H)R¹³ᵃ, —(CRᵍRʰ)ᵣ—C(O)OR¹³, or G¹;

R⁷ᵇ and R¹⁰, at each occurrence, are each independently hydrogen, alkyl, haloalkyl, —(CRᵍRʰ)ᵣ—C(O)OR¹³, or G¹;

R⁸ and R¹¹, at each occurrence, are each independently hydrogen, alkyl, haloalkyl, —S(O)₂—R¹³ᵃ, —S(O)₂—N(R¹³)(R¹⁴), —C(O)OR¹³, —C(O)N(R¹³)(R¹⁴), or G¹;

p, q, and r, at each occurrence, are each independently 1, 2, 3, or 4;

Rᵉ, Rᶠ, Rᵍ, and Rʰ, at each occurrence, are each independently hydrogen, halogen, alkyl, or haloalkyl;

R¹⁴, at each occurrence, is independently hydrogen, alkyl or haloalkyl;

R¹⁵, at each occurrence, is independently alkyl, haloalkyl, or G¹;

R¹³, at each occurrence, is independently hydrogen, alkyl, haloalkyl, or G¹;

R¹³ᵃ, at each occurrence, is independently alkyl, haloalkyl, or G¹; and

G¹, at each occurrence, is independently aryl, heteroaryl, cycloalkyl, heterocycle, arylalkyl, heteroarylalkyl, cycloalkylalkyl, or heterocyclealkyl, wherein the aryl, heteroaryl, cycloalkyl, heterocycle, aryl moiety of the arylalkyl, heteroaryl moiety of the heteroarylalkyl, cycloalkyl moiety of the cycloalkylalkyl, and heterocycle moiety of the heterocyclealkyl, are each independently unsubstituted or further substituted with 1, 2, 3, 4, or 5 substituents selected from the group consisting of alkyl, halogen, —CN, —NO₂, —OH, —O(alkyl), —NH₂, —N(H)(alkyl), —N(alkyl)₂, —C(O)OH, —C(O)O(alkyl), —C(O)NH₂, —C(O)N(H)(alkyl), —C(O)N(alkyl)₂, haloalkyl, and alkyl substituted with one substituent selected from the group consisting of —CN, —NO₂, —OH, —O(alkyl), —NH₂, —N(H)(alkyl), —N (alkyl)₂, —C(O)OH, —C(O)O(alkyl), —C(O)NH₂, —C(O)N(H)(alkyl), and —C(O)N(alkyl)₂.

2. The method of claim 1 further comprising the step of co-administering with one or more pharmaceutical agents selected from the group consisting of DPPIV inhibitor, incretin mimetic, metformin, fenofibrate, rimonabant, sibutramine, orlistat, nicotinic acid, and a statin.

3. A method for treating a disorder selected from the group consisting of type 2 diabetes, obesity, elevated plasma triglycerides, metabolic syndrome, non-alcoholic steatohepatitis, and non-alcoholic fatty liver disease, said method comprising the step of administering to a subject in need thereof a pharmaceutical composition comprising a compound of formula (I),

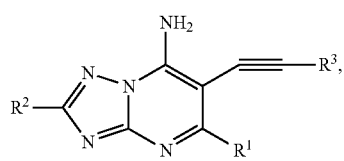

or a pharmaceutically acceptable salt thereof, wherein
R¹ is hydrogen or alkyl;
R² is hydrogen;

R³ is cycloalkyl, aryl, heteroaryl, heterocycle, —(CRᵃRᵇ)ₘ—R⁴, —C(O)OR⁵, —C(R⁵)=N—O(Rʸ), —C(O)—R⁵, or —C(O)—N(R⁵)(R⁶);

m is 1, 2, 3 or 4;

Rᵃ, at each occurrence, is independently hydrogen, halogen, alkyl, alkenyl, haloalkyl, —OR⁷ᵃ, —N(R⁸)(R⁹), —C(O)OR⁷ᵇ, —C(O)—R⁷ᵇ, —C(O)—N(R⁸)(R⁹), —(CRᶜRᵈ)ₚ—OR⁷ᵃ, —(CRᶜRᵈ)ₚ—N(R⁸)(R⁹), —(CRᶜRᵈ)ₚ—C(O)OR⁷ᵇ, —(CRᶜRᵈ)ₚ—C(O)—R⁷ᵇ, —(CRᶜRᵈ)ₚ—C(O)—N(R⁸)(R⁹), aryl, heteroaryl, cycloalkyl, or heterocycle;

Rᵇ, at each occurrence, is independently hydrogen, halogen, alkyl, alkenyl, haloalkyl, —C(O)OR⁷ᵇ, —C(O)—R⁷ᵇ, —C(O)—N(R⁸)(R⁹), —(CRᶜRᵈ)ₚ—OR⁷ᵃ, —(CRᶜRᵈ)ₚ—N(R⁸)(R⁹), —(CRᶜRᵈ)ₚ—C(O)OR⁷ᵇ, —(CRᶜRᵈ)ₚ—C(O)—R⁷ᵇ, —(CRᶜRᵈ)ₚ—C(O)—N(R⁸)(R⁹), aryl, heteroaryl, cycloalkyl, or heterocycle;

optionally, Rᵃ and Rᵇ together is =CH₂;

Rᶜ and Rᵈ, at each occurrence, are each independently hydrogen halogen, alkyl, or haloalkyl;

Rʸ is hydrogen, alkyl, haloalkyl, cycloalkyl, aryl, heteroaryl, heterocycle, cycloalkylalkyl, arylalkyl, heteroarylalkyl, or heterocyclealkyl;

R⁴ is hydrogen, alkyl, haloalkyl, cycloalkyl, aryl, heteroaryl, or heterocycle, provided that when R⁴ is hydrogen, alkyl or haloalkyl, then at least one Rᵃ is —OR⁷ᵃ, —N(R⁸)(R⁹), —C(O)OR⁷ᵇ, —C(O)—R⁷ᵇ, —C(O)—N (R⁸)(R⁹), —(CRᶜRᵈ)ₚ—OR⁷ᵃ, —(CRᶜRᵈ)ₚ—N(R⁸)(R⁹), —(CRᶜRᵈ)ₚ—C(O)OR⁷ᵇ, —(CRᶜRᵈ)ₚ—C(O)—R⁷ᵇ, or —(CRᶜRᵈ)ₚ—C(O)—N(R⁸)(R⁹); or Rᵃ and Rᵇ together is =CH₂;

R⁵, at each occurrence, is independently alkyl, haloalkyl cycloalkyl, aryl, heteroaryl, heterocycle, cycloalkylalkyl, arylalkyl, heteroarylalkyl, or heterocyclealkyl;

wherein each of the cycloalkyl, aryl, heteroaryl, heterocycle, cycloalkyl moiety of the cycloalkylalkyl, aryl moiety of the arylalkyl, heteroaryl moiety of the heteroarylalkyl, and heterocycle moiety of the heterocyclealkyl, as represented by R³, Rᵃ, Rᵇ, R⁴, R⁵, and Rʸ, is independently unsubstituted or further substituted with 1, 2, 3, 4 or 5 substituents selected from the group consisting of alkyl, halogen, haloalkyl, oxo, —OR¹⁰, —S(R¹⁴), —S(O)₂R¹⁵, —S(O)₂N(R¹¹)(R¹²), —N(R¹¹)(R¹²), —C(O)OR¹⁰, —C(O)O(trialkylsilylalkyl), —C(O)N(R¹¹)(R¹²), —(CRᵉRᶠ)_q—OR¹⁰, —(CRᵉRᶠ)_q—N(R¹¹)(R¹²), —(CRᵉRᶠ)_q—C(O)OR¹⁰, —(CRᵉRᶠ)_q—C(O)N(R¹¹)(R¹²), G¹, and =N—O(R¹⁰);

R⁶, R⁹ and R¹², at each occurrence, are each independently hydrogen, alkyl or haloalkyl;

R⁷ᵃ, at each occurrence, is each independently hydrogen, alkyl, haloalkyl, —N=C(H)R¹³ᵃ, —(CRᵍRʰ)ᵣ—C(O)OR¹³, or G¹;

R⁷ᵇ and R¹⁰, at each occurrence, are each independently hydrogen, alkyl, haloalkyl, (CRᵍRʰ)ᵣ—C(O)OR¹³, or G¹;

R⁸ and R¹¹, at each occurrence, are each independently hydrogen, alkyl, haloalkyl, —S(O)₂—R¹³ᵃ, —S(O)₂—N(R¹³)(R¹⁴), —C(O)OR¹³, —C(O)N(R¹³)(R¹⁴), or G¹;

p, q, and r, at each occurrence, are each independently 1, 2, 3, or 4;

Rᵉ, Rᶠ, Rᵍ, and Rʰ, at each occurrence, are each independently hydrogen, halogen, alkyl, or haloalkyl;

R¹⁴, at each occurrence, is independently hydrogen, alkyl or haloalkyl;

R¹⁵, at each occurrence, is independently alkyl, haloalkyl, or G¹;

$R^{13}$, at each occurrence, is independently hydrogen, alkyl, haloalkyl, or $G^1$;

$R^{13a}$, at each occurrence, is independently alkyl, haloalkyl, or $G^1$; and $G^1$, at each occurrence, is independently aryl, heteroaryl, cycloalkyl, heterocycle, arylalkyl, heteroarylalkyl, cycloalkylalkyl, or heterocyclealkyl, wherein the aryl, heteroaryl, cycloalkyl, heterocycle, aryl moiety of the arylalkyl, heteroaryl moiety of the heteroarylalkyl, cycloalkyl moiety of the cycloalkylalkyl, and heterocycle moiety of the heterocyclealkyl, are each independently unsubstituted or further substituted with 1, 2, 3, 4, or 5 substituents selected from the group consisting of alkyl, halogen, —CN, —NO$_2$, —OH, —O(alkyl), —NH$_2$, —N(H)(alkyl), —N(alkyl)$_2$, —C(O)OH, —C(O)O(alkyl), —C(O)NH$_2$, —C(O)N(H)(alkyl), —C(O)N(alkyl)$_2$, haloalkyl, and alkyl substituted with one substituent selected from the group consisting of —CN, —NO$_2$, —OH, —O(alkyl), —NH$_2$, —N(H)(alkyl), —N(alkyl)$_2$, —C(O)OH, —C(O)O(alkyl), —C(O)NH$_2$, —C(O)N(H)(alkyl), and —C(O)N(alkyl)$_2$, in combination with a pharmaceutically acceptable carrier.

4. The method of claim 1, wherein $R^3$ is cycloalkyl or heterocycle.

5. The method of claim 1, wherein $R^3$ is formula (a)

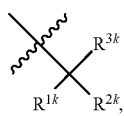

(a)

wherein $R^{1k}$ and $R^{2k}$ together with the carbon atom to which they are attached form a cycloalkyl or a heterocycle ring, each of which is optionally further substituted with 1, 2, 3, 4 or 5 substituents selected from the group consisting of alkyl, halogen, haloalkyl, oxo, —OR$^{10}$, —S(R$^{14}$), —S(O)$_2$R$^{15}$, —S(O)$_2$N(R$^{11}$)(R$^{12}$), —N(R$^{11}$)(R$^{12}$), —C(O)OR$^{10}$, —C(O)O(trialkylsilylalkyl), —C(O)N(R$^{11}$)(R$^{12}$), —(CR$^e$R$^f$)$_q$—OR$^{10}$, —(CR$^e$R$^f$)$_q$—N(R$^{11}$)(R$^{12}$), —(CR$^e$R$^f$)$_q$—C(O)OR$^{10}$, —(CR$^e$R$^f$)$_q$—C(O)N(R$^{11}$)(R$^{12}$), and =N—O(R$^{10}$);

$R^{3k}$ is —OR$^{10}$, —N(R$^{11}$)(R$^{12}$), —C(O)OR$^{10}$, or —C(O)O(trialkylsilylalkyl); and $R^e$, $R^f$, q, $R^{10}$, $R^{11}$, $R^{12}$, $R^{14}$, and $R^{15}$ are as defined in claim 1.

6. The method of claim 1, wherein $R^3$ is aryl, unsubstituted or substituted, with 1, 2, 3, 4 or 5 substituents selected from the group consisting of alkyl, haloalkyl, halogen, —OR$^{10}$, —S(R$^{14}$), —S(O)$_2$R$^{15}$, —S(O)$_2$N(R$^{11}$)(R$^{12}$), —N(R$^{11}$)(R$^{12}$), —C(O)OR$^{10}$, —C(O)O(trialkylsilylalkyl), —C(O)N(R$^{11}$)(R$^{12}$), —(CR$^e$R$^f$)$_q$—OR$^{10}$, —(CR$^e$R$^f$)$_q$—N(R$^{11}$)(R$^{12}$), —(CR$^e$R$^f$)$_q$—C(O)OR$^{10}$, —(CR$^e$R$^f$)$_q$—C(O)N(R$^{11}$)(R$^{12}$), and $G^1$, and $R^e$, $R^f$, q, $R^{10}$, $R^{11}$, $R^{12}$, $R^{14}$, $R^{15}$, and $G^1$ are as defined in claim 1.

7. The method of claim 1, wherein $R^3$ is —(CR$^a$R$^b$)$_m$—R$^4$, wherein $R^a$, at each occurrence, is independently hydrogen, halogen, alkyl, alkenyl, haloalkyl, —OR$^{7a}$, —N(R$^8$)(R$^9$), —C(O)OR$^{7b}$, —C(O)—R$^{7b}$, —C(O)—N(R$^8$)(R$^9$), —(CR$^c$R$^d$)$_p$—OR$^{7a}$, —(CR$^c$R$^d$)$_p$—N(R$^8$)(R$^9$), —(CR$^c$R$^d$)$_p$—C(O)OR$^{7b}$, —(CR$^c$R$^d$)$_p$—C(O)—R$^{7b}$, —(CR$^c$R$^d$)$_p$—C(O)—N(R$^8$)(R$^9$), aryl, heteroaryl, cycloalkyl, or heterocycle;

$R^b$, at each occurrence, is independently hydrogen, halogen, alkyl, alkenyl, haloalkyl, —C(O)OR$^{7b}$, —C(O)—R$^{7b}$, —C(O)—N(R$^8$)(R$^9$), —(CR$^c$R$^d$)$_p$—OR$^{7a}$, —(CR$^c$R$^d$)$_p$—N(R$^8$)(R$^9$), —(CR$^c$R$^d$)$_p$—C(O)OR$^{7b}$, —(CR$^c$R$^d$)$_p$—C(O)—R$^{7b}$, —(CR$^c$R$^d$)$_p$—C(O)—N(R$^8$)(R$^9$), aryl, heteroaryl, cycloalkyl, or heterocycle;

or $R^a$ and $R^b$ together is =CH$_2$; and m, p, $R^c$, $R^d$, $R^4$, $R^{7a}$, $R^8$, and $R^9$ are as defined claim 1.

8. The method of claim 7, wherein $R^a$ and $R^b$, at each occurrence, are each independently hydrogen, alkyl, alkenyl, halogen or haloalkyl, and $R^4$ is cycloalkyl, aryl, heteroaryl, or heterocycle.

9. The method of claim 1, wherein $R^3$ is formula (b)

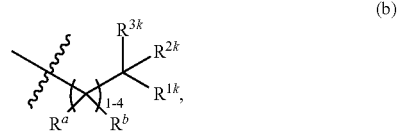

(b)

wherein $R^a$ and $R^b$, at each occurrence, are each independently hydrogen, halogen, alkyl, alkenyl, or haloalkyl;

$R^{1k}$ and $R^{2k}$ together with the carbon atom to which they are attached form a cycloalkyl or heterocycle ring, wherein each of the ring is independently unsubstituted or substituted with 1, 2, 3, 4, or 5 substituents selected from the group consisting of alkyl, halogen, haloalkyl, oxo, —OR$^{10}$, —S(R$^{14}$), —S(O)$_2$R$^{15}$, —S(O)$_2$N(R$^{11}$)(R$^{12}$), —N(R$^{11}$)(R$^{12}$), —C(O)OR$^{10}$, —C(O)O(trialkylsilylalkyl), —C(O)N(R$^{11}$)(R$^{12}$), —(CR$^e$R$^f$)$_q$—OR$^{10}$, —(CR$^e$R$^f$)$_q$—N(R$^{11}$)(R$^{12}$), —(CR$^e$R$^f$)$_q$—C(O)OR$^{10}$, —(CR$^e$R$^f$)$_q$—C(O)N(R$^{11}$)(R$^{12}$), and =N—O(R$^{10}$);

$R^{3k}$ is —OR$^{10}$, —N(R$^{11}$)(R$^{12}$), or —C(O)OR$^{10}$; and $R^e$, $R^f$, q, $R^{10}$, $R^{11}$, $R^{12}$, $R^{14}$, and $R^{15}$ are as defined in claim 1.

10. The method of claim 1, wherein $R^3$ is formula (c)

(c)

wherein $R^b$ is hydrogen, halogen, alkyl, alkenyl, —C(O)OR$^{7b}$, haloalkyl, aryl, heteroaryl, cycloalkyl, or heterocycle;

$R^a$ is OR$^{7a}$, N(R$^8$)(R$^9$), or —C(O)OR$^{7b}$;

or $R^a$ and $R^b$ together is =CH$_2$;

$R^4$ is hydrogen, alkyl, haloalkyl, cycloalkyl, aryl, heteroaryl, or heterocycle; and $R^{7a}$, $R^{7b}$, $R^8$, and $R^9$ are as defined in claim 1.

11. The method of claim 1, wherein $R^{7a}$ is hydrogen, $C_{1-6}$ alkyl, haloalkyl, —(CR$^g$R$^h$)$_r$—C(O)OR$^{13}$, unsubstituted or substituted phenyl; and $R^{13}$, $R^g$, $R^h$, $R^{7b}$, and $R^9$ are each independently hydrogen, $C_{1-6}$ alkyl, or haloalkyl.

12. The method of claim 1, wherein $R^3$ is formula (d)

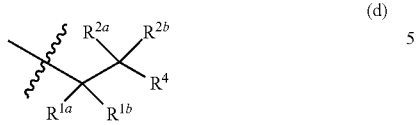

wherein
- $R^{1b}$ is hydrogen, alkyl, alkenyl, halogen, —C(O)OR$^{7b}$, haloalkyl, aryl, heteroaryl, cycloalkyl, or heterocycle, $R^{1a}$ is OR$^{7a}$, N(R$^8$)(R$^9$) or —C(O)OR$^{7b}$, and $R^{2a}$ and $R^{2b}$, at each occurrence, are independently hydrogen, halogen, alkyl, alkenyl, or haloalkyl; or
- $R^{2b}$ is hydrogen, alkyl, alkenyl, halogen, —C(O)OR$^{7b}$, haloalkyl, aryl, heteroaryl, cycloalkyl, or heterocycle, $R^{2a}$ is OR$^{7a}$, N(R$^8$)(R$^9$) or —C(O)OR$^{7b}$, and $R^{1a}$ and $R^{1b}$, at each occurrence, are independently hydrogen, halogen, alkyl, alkenyl, or haloalkyl;
- each of the aryl, heteroaryl, cycloalkyl, or heterocycle as represented by $R^{1b}$ and $R^{2b}$ is independently unsubstituted or further substituted with 1, 2, 3, 4 or 5 substituents selected from the group consisting of 1, 2, 3, 4 or 5 substituents selected from the group consisting of alkyl, halogen, haloalkyl, oxo, —OR$^{10}$, —S(R$^{14}$), —S(O)$_2$R$^{15}$, —S(O)N(R$^{11}$)(R$^{12}$), —N(R$^{11}$)(R$^{12}$), —C(O)OR$^{10}$, —C(O)O(trialkylsilylalkyl), —C(O)N(R$^{11}$)(R$^{12}$), —(CR$^e$R$^f$)$_q$—OR$^{10}$, —(CR$^e$R$^f$)$_q$—N(R$^{11}$)(R$^{12}$), —(CR$^e$R$^f$)$_q$—C(O)OR$^{10}$, —(CR$^e$R$^f$)$_q$—C(O)N(R$^{11}$)(R$^{12}$), G$^1$, and =N—O(R$^{10}$);
- $R^4$ is hydrogen, alkyl, haloalkyl, cycloalkyl, aryl, heteroaryl, or heterocycle; and
- $R^{7a}$, $R^{7b}$, $R^8$, $R^e$, $R^f$, $R^9$, $R^{10}$, $R^{11}$, $R^{12}$, $R^{14}$, $R^{15}$, and q, are as defined in claim 1.

13. The method of claim 1, wherein $R^3$ is —C(O)—R$^5$.

14. The method of claim 1, wherein the compound of formula (I) is selected from the group consisting of
- 6-[(4-aminophenyl)ethynyl]-5-methyl[1,2,4]triazolo[1,5-a]pyrimidin-7-amine;
- 6-(cyclohexylethynyl)-5-methyl[1,2,4]triazolo[1,5-a]pyrimidin-7-amine;
- 5-methyl-6-(4-phenylbut-1-ynyl)[1,2,4]triazolo[1,5-a]pyrimidin-7-amine;
- 1-[(7-amino-5-methyl[1,2,4]triazolo[1,5-a]pyrimidin-6-yl)ethynyl]cyclopentanol;
- 1-[(7-amino-5-methyl[1,2,4]triazolo[1,5-a]pyrimidin-6-yl)ethynyl]cyclohexanol;
- 4-[(7-amino-5-methyl[1,2,4]triazolo[1,5-a]pyrimidin-6-yl)ethynyl]tetrahydro-2H-pyran-4-ol;
- 4-(7-amino-5-methyl[1,2,4]triazolo[1,5a]pyrimidin-6-yl)-2-cyclopentylbut-3-yn-2-ol;
- 4-(7-amino-5-methyl[1,2,4]triazolo[1,5-a]pyrimidin-6-yl)-2-phenylbut-3-yn-2-ol;
- 4-(7-amino-5-methyl[1,2,4]triazolo[1,5-a]pyrimidin-6-yl)-1,1,1-trifluoro-2-phenylbut-3-yn-2-ol;
- 3-(7-amino-5-methyl[1,2,4]triazolo[1,5-a]pyrimidin-6-yl)-1,1-diphenylprop-2-yn-1-ol;
- 3-(7-amino-5-methyl[1,2,4]triazolo[1,5-a]pyrimidin-6-yl)-1-phenylprop-2-yn-1-ol;
- 6-(3-cyclohexylprop-1-ynyl)-5-methyl[1,2,4]triazolo[1,5-a]pyrimidin-7-amine;
- 3-(7-amino-5-methyl[1,2,4]triazolo[1,5-a]pyrimidin-6-yl)-1-cyclopropyl-1-phenylprop-2-yn-1-ol;
- 6-[(4-methoxyphenyl)ethynyl]-5-methyl[1,2,4]triazolo[1,5-a]pyrimidin-7-amine;
- 3-(7-amino-5-methyl[1,2,4]triazolo[1,5-a]pyrimidin-6-yl)-1,1-bis(4-chlorophenyl)prop-2-yn-1-ol;
- 5-methyl-6-(3-morpholin-4-yl-3-phenylprop-1-ynyl)[1,2,4]triazolo[1,5-a]pyrimidin-7-amine;
- 3-(7-amino-5-methyl[1,2,4]triazolo[1,5-a]pyrimidin-6-yl)-1-(1-methylcyclohexyl)-1-phenylprop-2-yn-1-ol;
- 3-(7-amino-5-methyl[1,2,4]triazolo[1,5-a]pyrimidin-6-yl)-1-(3,4'-dichloro-1,1'-biphenyl-4-yl)prop-2-yn-1-ol;
- 1-(7 amino-5-methyl[1,2,4]triazolo[1,5-a]pyrimidin-6-yl)-3-(1,1'-biphenyl-4-yl)-4,4-dimethylpent-1-yn-3-ol;
- methyl 4-(7-amino-5-methyl[1,2,4]triazolo[1,5-a]pyrimidin-6-yl)-2-hydroxy-2-phenylbut-3-ynoate;
- N-{1-[(7-amino-5-methyl[1,2,4]triazolo[1,5-a]pyrimidin-6-yl)ethynyl]cyclohexyl}-3-chlorobenzenesulfonamide;
- N-{4-[(7-amino-5-methyl[1,2,4]triazolo[1,5-a]pyrimidin-6-yl)ethynyl]phenyl}-N'-(3-chlorophenyl)urea;
- (1R,4R)-2-[(7-amino-5-methyl[1,2,4]triazolo[1,5-a]pyrimidin-6-yl)ethynyl]-1,7,7-trimethylbicyclo[2.2.1]heptan-2-ol;
- (1Z)-2-[3-(7-amino-5-methyl[1,2,4]triazolo[1,5-a]pyrimidin-6-yl)prop-2-ynyl]-4-tert-butylcyclohexanone oxime;
- 4-(7-amino-5-methyl[1,2,4]triazolo[1,5-a]pyrimidin-6-yl)-2-(4-isopropyl-2-methylcyclopentyl)but-3-yn-2-ol;
- methyl {[3-(7-amino-5-methyl[1,2,4]triazolo[1,5-a]pyrimidin-6-yl)-1-phenylprop-2-ynyl]oxy}acetate;
- {[3-(7-amino-5-methyl[1,2,4]triazolo[1,5-a]pyrimidin-6-yl)-1-phenylprop-2-ynyl]oxy}acetic acid;
- {2-[(7-amino-5-methyl[1,2,4]triazolo[1,5-a]pyrimidin-6-yl)ethynyl]phenyl}methanol;
- {3-[3-(7-amino-5-methyl[1,2,4]triazolo[1,5-a]pyrimidin-6-yl)-1-hydroxy-1-methylprop-2-ynyl]-2,2-dimethylcyclobutyl}acetic acid;
- 4-(7-amino-5-methyl[1,2,4]triazolo[1,5-a]pyrimidin-6-yl)-2-cyclobutylbut-3-yn-2-ol;
- 4-(7-amino-5-methyl[1,2,4]triazolo[1,5-a]pyrimidin-6-yl)-2-(3-methylcyclobutyl)but-3-yn-2-ol;
- 5-methyl-6-(3-phenylprop-1-ynyl) [1,2,4]triazolo[1,5-a]pyrimidin-7-amine;
- 6-(3-cyclopentylprop-1-ynyl)-5-methyl[1,2,4]triazolo[1,5-a]pyrimidin-7-amine;
- 6-[(1-aminocyclohexyl)ethynyl]-5-methyl[1,2,4]triazolo[1,5-a]pyrimidin-7-amine;
- 3-(7-amino-5-methyl[1,2,4]triazolo[1,5-a]pyrimidin-6-yl)-1-cyclopentylprop-2-yn-1-ol;
- 3-(7-amino-5-methyl[1,2,4]triazolo[1,5-a]pyrimidin-6-yl)-1-(2,4-dichlorophenyl)prop-2-yn-1-ol;
- 4-(7-amino-5-methyl[1,2,4]triazolo[1,5-a]pyrimidin-6-yl)-1-cyclopentyl-2-methylbut-3-yn-2-ol;
- {4-[(7-amino-5-methyl[1,2,4]triazolo[1,5-a]pyrimidin-6-yl)ethynyl]-4-hydroxycyclohexyl}acetic acid;
- methyl {4-[(7-amino-5-methyl[1,2,4]triazolo[1,5-a]pyrimidin-6-yl)ethynyl]-4-hydroxycyclohexyl}acetate;
- (1R,4S)-2-[(7-amino-5-methyl[1,2,4]triazolo[1,5-a]pyrimidin-6-yl)ethynyl]bicyclo[2.2.1]heptan-2-ol;
- (1R,2S,4R)-2-[(7-amino-5-methyl[1,2,4]triazolo[1,5-a]pyrimidin-6-yl)ethynyl]-1,7,7-trimethylbicyclo[2.2.1]heptan-2-ol;
- (1R,2R,4S)-2-[(7-amino-5-methyl[1,2,4]triazolo[1,5-a]pyrimidin-6-yl)ethynyl]-1,3,3-trimethylbicyclo[2.2.1]heptan-2-ol;
- tert-butyl {4-[(7-amino-5-methyl[1,2,4]triazolo[1,5-a]pyrimidin-6-yl)ethynyl]-4-hydroxycyclohexyl}acetate;
- (1S,2S,4R)-2-[(7-amino-5-methyl[1,2,4]triazolo[1,5-a]pyrimidin-6-yl)ethynyl]-1,3,3-trimethylbicyclo[2.2.1]heptan-2-ol;

(1S,2R,4S)-2-[(7-amino-5-methyl[1,2,4]triazolo[1,5-a]pyrimidin-6-yl)ethynyl]-1,7,7-trimethylbicyclo[2.2.1]heptan-2-ol;

1-[3-(7-amino-5-methyl[1,2,4]triazolo[1,5-a]pyrimidin-6-yl)prop-2-ynyl]cyclopentanol;

1-[(7-amino[1,2,4]triazolo[1,5-a]pyrimidin-6-yl)ethynyl]cyclopentanol;

1-[3-(7-amino[1,2,4]triazolo[1,5-a]pyrimidin-6-yl)prop-2-ynyl]cyclopentanol;

(1R,2S,4R)-2-[3-(7-amino-5-methyl[1,2,4]triazolo[1,5-a]pyrimidin-6-yl)prop-2-ynyl]-1,7,7-trimethylbicyclo[2.2.1]heptan-2-ol;

methyl 1-[3-(7-amino-5-methyl[1,2,4]triazolo[1,5-a]pyrimidin-6-yl)prop-2-ynyl]cyclohexanecarboxylate;

6-[3-(4-methoxyphenoxy)but-1-ynyl]-5-methyl[1,2,4]triazolo[1,5-a]pyrimidin-7-amine;

(1R)-3-(7-amino-5-methyl[1,2,4]triazolo[1,5-a]pyrimidin-6-yl)-1-phenylprop-2-yn-1-ol;

(1S)-3-(7-amino-5-methyl[1,2,4]triazolo[1,5-a]pyrimidin-6-yl)-1-phenylprop-2-yn-1-ol;

4-(7-amino-5-methyl[1,2,4]triazolo[1,5-a]pyrimidin-6-yl)-1-phenylbut-3-yn-1-ol;

(trans)-ethyl 2-[3-(7-amino-5-methyl[1,2,4]triazolo[1,5-a]pyrimidin-6-yl)-1-hydroxyprop-2-ynyl]cyclopropanecarboxylate;

1-[3-(7-amino-5-methyl[1,2,4]triazolo[1,5-a]pyrimidin-6-yl)prop-2-ynyl]cyclohexanecarboxylic acid;

1-[(7-amino-5-ethyl[1,2,4]triazolo[1,5-a]pyrimidin-6-yl)ethynyl]cyclopentanol;

3-(7-amino-5-methyl[1,2,4]triazolo[1,5-a]pyrimidin-6-yl)-1-phenylprop-2-yn-1-one;

2-{3-[3-(7-amino-5-methyl[1,2,4]triazolo[1,5-a]pyrimidin-6-yl)-1-hydroxy-1-methylprop-2-ynyl]-2,2-dimethylcyclobutyl}acetamide;

(1R,2S,4R)-2-[(7-amino-5-ethyl[1,2,4]triazolo[1,5-a]pyrimidin-6-yl)ethynyl]-1,7,7-trimethylbicyclo[2.2.1]heptan-2-ol;

1-[(7-amino-5-methyl[1,2,4]triazolo[1,5-a]pyrimidin-6-yl)ethynyl]cycloheptanol;

{[3-(7-amino-5-methyl[1,2,4]triazolo[1,5-a]pyrimidin-6-yl)-1-cyclopentylprop-2-ynyl]oxy}acetic acid;

({1-[(7-amino-5-methyl[1,2,4]triazolo[1,5-a]pyrimidin-6-yl)ethynyl]cyclopentyl}oxy)acetic acid;

3-(7-amino-5-methyl[1,2,4]triazolo[1,5-a]pyrimidin-6-yl)-1-cyclohexylprop-2-yn-1-ol;

methyl 4-[3-(7-amino-5-methyl[1,2,4]triazolo[1,5-a]pyrimidin-6-yl)-1-hydroxyprop-2-ynyl]cyclohexanecarboxylate;

4-[3-(7-amino-5-methyl[1,2,4]triazolo[1,5-a]pyrimidin-6-yl)-1-hydroxyprop-2-ynyl]cyclohexanecarboxylic acid;

{3-[3-(7-amino-5-methyl[1,2,4]triazolo[1,5-a]pyrimidin-6-yl)-1-methyleneprop-2-ynyl]-2,2-dimethylcyclobutyl}acetic acid;

methyl 1-[3-(7-amino-5-methyl[1,2,4]triazolo[1,5-a]pyrimidin-6-yl) prop-2-ynyl]cyclopentanecarboxylate;

2-(trimethylsilyl)ethyl 1-[3-(7-amino-5-methyl[1,2,4]triazolo[1,5-a]pyrimidin-6-yl) prop-2-ynyl]cyclohexanecarboxylate;

6-[(4-bromophenyl)ethynyl]-5-methyl[1,2,4]triazolo[1,5-a]pyrimidin-7-amine;

6-[(4-chlorophenyl)ethynyl]-5-methyl[1,2,4]triazolo[1,5-a]pyrimidin-7-amine;

methyl 2-{-4-[(7-amino-5-methyl[1,2,4]triazolo[1,5-a]pyrimidin-6-yl)ethynyl]phenyl}-2-methylpropanoate; and ethyl 1-[4-(7-amino-5-methyl[1,2,4]triazolo[1,5-a]pyrimidin-6-yl)but-3-ynyl]-2-oxocyclopentanecarboxylate;

or a pharmaceutically acceptable salt thereof.

\* \* \* \* \*